US012590132B2

(12) United States Patent
Chen et al.

(10) Patent No.: US 12,590,132 B2
(45) Date of Patent: Mar. 31, 2026

(54) FGF21 VARIANT POLYPEPTIDE MOLECULES AND APPLICATION THEREOF

(71) Applicant: SUNSHINE LAKE PHARMA CO., LTD., Dongguan (CN)

(72) Inventors: Chao Chen, Dongguan (CN); Shushan Lin, Dongguan (CN); Yu Li, Dongguan (CN); Xiaoping Li, Dongguan (CN); Xiaofeng Chen, Dongguan (CN); Wenjia Li, Dongguan (CN); Liang Liu, Dongguan (CN); Zheng Fu, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 1090 days.

(21) Appl. No.: 17/418,624

(22) PCT Filed: Mar. 4, 2020

(86) PCT No.: PCT/CN2020/077750
§ 371 (c)(1),
(2) Date: Jun. 25, 2021

(87) PCT Pub. No.: WO2020/177712
PCT Pub. Date: Sep. 10, 2020

(65) Prior Publication Data
US 2022/0064244 A1 Mar. 3, 2022

(30) Foreign Application Priority Data

Mar. 5, 2019 (CN) .......................... 201910162060.6
Aug. 16, 2019 (CN) .......................... 201910758104.1

(51) Int. Cl.
| | |
|---|---|
| *C07K 14/50* | (2006.01) |
| *A61K 38/00* | (2006.01) |
| *A61P 1/16* | (2006.01) |
| *A61P 1/18* | (2006.01) |
| *A61P 3/04* | (2006.01) |
| *A61P 3/08* | (2006.01) |
| *A61P 3/10* | (2006.01) |
| *C07K 14/605* | (2006.01) |

(52) U.S. Cl.
CPC ................ *C07K 14/50* (2013.01); *A61P 3/04* (2018.01); *A61P 3/08* (2018.01); *A61P 3/10* (2018.01); *C07K 14/605* (2013.01); *A61K 38/00* (2013.01); *C07K 2319/00* (2013.01); *C07K 2319/30* (2013.01)

(58) Field of Classification Search
CPC ..................................................... C07K 14/50
See application file for complete search history.

(56) References Cited

U.S. PATENT DOCUMENTS

| | | | |
|---|---|---|---|
| 7,576,190 | B2 | 8/2009 | Glaesner et al. |
| 7,582,607 | B2 | 9/2009 | Frye et al. |
| 7,622,445 | B2 | 11/2009 | Frye et al. |
| 7,655,627 | B2 | 2/2010 | Frye et al. |
| 8,361,963 | B2 | 1/2013 | Belouski et al. |
| 8,557,769 | B2 | 10/2013 | Coskun et al. |
| 8,795,985 | B2 | 8/2014 | Belouski et al. |
| 8,835,385 | B2 | 9/2014 | Belouski et al. |
| 8,883,726 | B2 | 11/2014 | Dickinson et al. |
| 8,927,492 | B2 | 1/2015 | Darling et al. |
| 9,279,013 | B2 | 3/2016 | Walker et al. |
| 9,422,353 | B2 | 8/2016 | Darling et al. |
| 11,679,143 | B2 * | 6/2023 | Chen ......................... A61P 3/04 424/134.1 |
| 2009/0305986 | A1 | 12/2009 | Belouski et al. |
| 2012/0052069 | A1 * | 3/2012 | Belouski ................... A61P 3/00 514/6.9 |
| 2013/0085098 | A1 * | 4/2013 | Dickinson ................. A61P 3/10 514/6.9 |
| 2013/0330336 | A1 | 12/2013 | Darling et al. |
| 2014/0056893 | A1 | 2/2014 | Coskun et al. |
| 2014/0213512 | A1 | 7/2014 | Ellison et al. |
| 2015/0141335 | A1 | 5/2015 | Ma et al. |
| 2016/0237133 | A1 | 8/2016 | Suh et al. |
| 2017/0166621 | A1 * | 6/2017 | Boettcher .............. C07K 14/50 |
| 2018/0280474 | A1 | 10/2018 | Xu et al. |
| 2018/0305428 | A1 | 10/2018 | Kim et al. |
| 2019/0142963 | A1 | 5/2019 | Dimarchi et al. |
| 2019/0314452 | A1 | 10/2019 | Hong et al. |

(Continued)

FOREIGN PATENT DOCUMENTS

| | | |
|---|---|---|
| CN | 1802386 A | 7/2006 |
| CN | 101993496 A | 3/2011 |
| CN | 104364261 A | 2/2015 |
| CN | 108350054 A | 7/2018 |
| CN | 108440668 A | 8/2018 |
| CN | 108570109 A | 9/2018 |
| WO | 2010/129600 A2 | 11/2010 |
| WO | 2013/049234 A2 | 4/2013 |

(Continued)

OTHER PUBLICATIONS

Rispens et al. Fc-Fc interactions of human IgG4 require dissociation of heavy chains and are formed predominantly by the intra-chain hinge isomer. Molecular Immunology. 2 (1-2): 35-42; Published: Jul. 9, 2012 (Year: 2012).*

(Continued)

*Primary Examiner* — Juliet C Switzer
*Assistant Examiner* — Katherine Ann Holtzman
(74) *Attorney, Agent, or Firm* — OLIFF PLC.

(57) ABSTRACT

An FGF21 polypeptide has one or more of the following properties: stable structure, long half-life, low immunogenicity, high biological activity, and enhanced glucose-lowering and lipid-lowering activities. A fusion protein or immunoconjugate includes the FGF21 polypeptide.

14 Claims, 19 Drawing Sheets

Specification includes a Sequence Listing.

(56) References Cited

U.S. PATENT DOCUMENTS

| | | |
|---|---|---|
| 2020/0024318 A1 | 1/2020 | Kim et al. |
| 2020/0360530 A1 | 11/2020 | DiMarchi et al. |

FOREIGN PATENT DOCUMENTS

| | | | |
|---|---|---|---|
| WO | 2013/052311 A1 | 4/2013 | |
| WO | 2013/188182 A1 | 12/2013 | |
| WO | WO-2016048999 A2 * | 3/2016 | |
| WO | 2016/114633 A1 | 7/2016 | |
| WO | 2017/180988 A2 | 10/2017 | |
| WO | WO-2018166461 A1 * | 9/2018 | ......... A61K 47/6811 |
| WO | 2019/154189 A1 | 8/2019 | |

OTHER PUBLICATIONS

Jun. 12, 2020 International Search Report issued in International Patent Application No. PCT/CN2020/077750.

Jun. 12, 2020 Written Opinion issued in International Patent Application No. PCT/CN2020/077750.

Yao Wen-bing-Expression and pharmacological evaluation of fusion protein FGF21-L-Fc-Acta Parmaceutica Sinica—2011, 46(7): 787-792.

Li Deshan-Enhancement of FGF21 expression by site-directed mutagenesis—Journal of Northeast Agricultural University—44(3),2013: 83-88.

Alexei Kharitonenkov-FGF-21 as a novel metabolic regulator—The Journal of Clinical Investigation-115(6), 2005: 1627-1635.

Jun Yin-Genetic fusion of human FGF21 to a synthetic polypeptide improves pharmacokinetics and pharmacodynamics in a mouse model of obesity—British Journal of Pharmacology—(2016) 173: 2208-2223.

Yan Weng—Glyco-engineered Long Acting FGF21 Variant with Optimal Pharmaceutical and Pharmacokinetic Properties to Enable Weekly to Twice Monthly—Subcutaneous Dosing—Scientific Reports—(2018) 8:4241.

Shanaka Stanislaus—A novel Fc FGF21 with improved resistance to proteolysis, increased affinity towards β-Klotho and enhanced efficacy in mice and cynomolgus monkeys—ndocrinology, May 2017, 158(5):1314-1327.

Oct. 8, 2023 Office Action issued in Chinese Patent Application No. 202010143690.1.

Feb. 7, 2024 Office Action issued in Chinese Patent Application No. 202010143690.1.

Feb. 19, 2024 Office Action issued in Japanese Patent Application No. 2021-551806.

Aug. 13, 2024 Office Action issued in Japanese Patent Application No. 2021-551806.

Apr. 14, 2025 Office Action issued in Korean Patent Application No. 10-2021-7031717.

Dec. 20, 2022 European Extended Search Report issued in 20 767 280.9.

Sep. 24, 2024 Office Action issued in Australian Patent Application No. 2020230668.

* cited by examiner

1. FGF21-RAHL    2. FGF21-1

3. FGF21-7      M. maker

Fasting blood glucose

FGF21 VARIANT POLYPEPTIDE MOLECULES AND APPLICATION THEREOF

CROSS REFERENCE TO RELATED APPLICATION

This application claims priority and benefits of Chinese Patent Application No. 201910162060.6 and 201910758104.1, filed with the State Intellectual Property Office on 5 Mar. 2019 and 16 Augest 2019 respectively; the entire content of which is incorporated herein by reference.

FIELD OF THE INVENTION

The present application relates to the field of biomedicine, and in particular to a polypeptide molecule and application thereof.

BACKGROUND OF THE INVENTION

Glucagon-like peptide-1 (GLP-1) is a type of incretin secreted by intestinal L cells. It stimulates islet β-cells to secrete insulin, maintaining insulin balance in patients. GLP-1 works indirectly through insulin, and it only affects type 2 diabetes, which limits its scope of application and effect. At the same time, GLP-1 has been reported to have a potential risk for thyroid cancer.

FGF21 belongs to one of the members of FGF (fibroblast growth factors, FGFs) family. FGF21 can promote the absorption of glucose by fat cells and enhance insulin sensitivity. At the same time, compared with insulin, FGF21 does not cause side effects such as hypoglycemia, and can effectively protect β islet cells and promote regeneration and repair of islet β cells. Moreover, it does not lead to potential tumor risk because of its lack of mitotic activity. FGF21 has a great potential to be a drug for the treatment of type II diabetes. In addition, FGF21 also has a good lipid-lowering effect and is a promising lipid-lowering drug.

However, FGF21 also faces enormous challenges in drug-gability. In one aspect, FGF21 has a short half-life. Its half-life is only about one hour in a mouse model (Xu et al., 2009). In another aspect, the biological activity of FGF21 in vivo is also limited. Therefore, there is an urgent need to transform FGF21.

SUMMARY OF THE INVENTION

The present application provides an FGF21 polypeptide, which has one or more of the following properties: (1) stable structure, long half-life; (2) low immunogenicity; (3) high biological activity; and (4) enhanced glucose-lowering and lipid-lowering activities.

In one aspect, the present application provides an FGF21 polypeptide, which comprises amino acid substitutions at the following positions: L98, S167, P171, R175, and R19, as compared to the amino acid sequence shown in SEQ ID NO: 1.

In some embodiments, the FGF21 polypeptide further comprises amino acid substitutions at one or more positions selected from the following group consisting of: R135, A180, A31, and G43.

In some embodiments, the FGF21 polypeptide comprises amino acid substitutions at amino acid residues selected from the group consisting of: (1) L98, S167, P171, R175 and R19; (2) L98, S167, P171, R175, R19, and R135; (3) L98, S167, P171, R175, R19, and A180; (4) L98, S167, P171, R175, R19, A31, and G43; and (5) L98, S167, P171, R175, R19, R135, A31 and G43, as compared to the amino acid sequence shown in SEQ ID NO: 1.

In some embodiments, the amino acid substitution at L98 is L98R.

In some embodiments, the amino acid substitution at S167 is S167H.

In some embodiments, the amino acid substitution at P171 is selected from the group consisting of P171A, P171G, and P171N.

In some embodiments, the amino acid substitution at R175 is R175L.

In some embodiments, the amino acid substitution at R19 is R19V.

In some embodiments, the FGF21 polypeptide further comprises an amino acid substitution at one or more positions selected from the following group consisting of: R135V, A180E, A31C, and G43C.

In some embodiments, compared to the amino acid sequence shown in SEQ ID NO: 1, the FGF21 polypeptide comprises amino acid substitutions selected from the group consisting of: (1) L98R, S167H, P171A, R175L and R19V; (2) L98R, S167H, P171G, R175L and R19V; (3) L98R, S167H, P171G, R175L, R19V and R135V; (4) L98R, S167H, P171G, R175L, R19V, and A180E; (5) L98R, S167H, P171A, R175L, R19V, and R135V; (6) L98R, S167H, P171A, R175L, R19V, A31C, and G43C; (7) L98R, S167H, P171G, R175L, R19V, A31C and G43C; (8) L98R, S167H, P171G, R175L, R19V, R135V, A31C and G43C; (9) L98R, S167H, P171A, R175L, R19V, R135V, A31C and G43C; and, (10) L98R, S167H, P171A, R175L, R19V and A180E.

In some embodiments, the polypeptide comprises the amino acid sequence shown in any one of the following groups: SEQ ID NOs: 2 to 11.

In another aspect, the present application provides a fusion protein or immunoconjugate comprising the FGF21 polypeptide described herein.

In some embodiments, the fusion protein or immunoconjugate further comprises an immunoglobulin Fc domain. In some embodiments, the immunoglobulin Fc domain is located at the C-terminus of the FGF21 polypeptide. In some embodiments, the immunoglobulin Fc domain is an Fc of human IgG or a functional variant thereof. In some embodiments, the immunoglobulin Fc domain comprises the amino acid sequence shown in any one of the following groups: SEQ ID NOs: 12 to 13.

In some embodiments, the fusion protein further comprises a linker. In certain embodiments, the linker is a peptide linker.

In some embodiments, wherein the N-terminus of the linker is connected to the C-terminus of the immunoglobulin Fc domain, and the C-terminus of the linker is connected to the N-terminus of the FGF21 polypeptide.

In some embodiments, the linker comprises the amino acid sequence shown in SEQ ID NO: 16.

In some embodiments, the fusion protein or immunoconjugate comprises the amino acid sequence shown in any one of the following groups: SEQ ID NOs: 17 to 26.

In some embodiments, the fusion protein or immunoconjugate further comprises GLP-1 or a functional variant thereof. In some embodiments, the GLP-1 or the functional variant thereof comprises the amino acid sequence shown in any one of the following groups: SEQ ID NOs: 14 to 15.

In some embodiments, the fusion protein or immunoconjugate further comprises an immunoglobulin Fc domain. In some embodiments, the immunoglobulin Fc domain is located at the C-terminus of the FGF21 polypeptide.

In some embodiments, the immunoglobulin Fc domain is an Fc of human IgG or a functional variant thereof. The immunoglobulin Fc domain comprises the amino acid sequence shown in any one of the following groups: SEQ ID NOs: 12 to 13.

In some embodiments, the fusion protein or immunoconjugate further comprises a linker. In some embodiments, the linker is a peptide linker.

In some embodiments, the linker comprises a first linker. The N-terminus of the first linker is connected to the C-terminus of the Fc domain, and the C-terminus of the first linker is connected to the N-terminus of the FGF21 polypeptide. In some embodiments, the linker comprises a second linker. The N-terminus of the second linker is connected to the C-terminus of the GLP-1 or the variant thereof, and the C-terminus of the second linker is connected to the N-terminus of the Fc domain.

In some embodiments, each of the first linker and the second linker independently comprises an amino acid sequence shown in any one of the following group: SEQ ID NO: 16.

In some embodiments, the fusion protein or immunoconjugate comprises the amino acid sequence shown in any one of the following groups: SEQ ID NOs: 27 to 36.

In another aspect, the application provides an isolated nucleic acid molecule encoding the FGF21 variant described herein or the fusion protein or immunoconjugate described herein.

In another aspect, provided herein is a vector comprising the isolated nucleic acid molecule described herein.

In another aspect, provided herein is a cell comprising or expressing the FGF21 polypeptide described herein, the fusion protein or immunoconjugate described herein, the isolated nucleic acid molecule described herein or the vector described herein.

In another aspect, provided herein is a pharmaceutical composition comprising the FGF21 polypeptide described herein, the fusion protein or immunoconjugate described herein, the isolated nucleic acid molecule described herein, the vector described herein, or the cell described herein, and optionally a pharmaceutically acceptable adjuvant.

In some embodiments, the FGF21 polypeptide described herein, the fusion protein or the immunoconjugate described herein is used in the manufacture of therapeutic medicines for the treatment of diseases caused by FGF21 metabolic disorders. In some embodiments, according to the use described in the present application, wherein the diseases caused by FGF21 metabolic disorders include diabetes, fatty liver, obesity, and/or pancreatitis. In some embodiments, provided herein is a method of treating diseases caused by FGF21 metabolic disorders comprising administrating a therapeutically effective amount of the FGF21 polypeptide described herein, the fusion protein or the immunoconjugate described herein to the patient. In some embodiments, provided herein is the FGF21 polypeptide described herein, the fusion protein or the immunoconjugate described herein for use in treating diseases caused by FGF21 metabolic disorders.

Other aspects and advantages of the present disclosure will be readily apparent to those skilled in the art from the following detailed description. Only the exemplary embodiments of the present disclosure are shown and described in the following detailed description. As recognized by those skilled in the art, the present disclosure will enable those skilled in the art to make modifications to the disclosed specific embodiments without departing from the spirit and scope of the invention. Accordingly, the drawings and the description of specification in the present application is merely illustrative, not restrictive.

DESCRIPTION OF THE DRAWINGS

Specific features of the invention in the present application are shown in the appended claims. The features and advantages of the invention in the application can be better understood by referring to the exemplary embodiments and drawings described in detail below. A brief description of the drawings is as follows:

EXAMPLES

Figure 1:
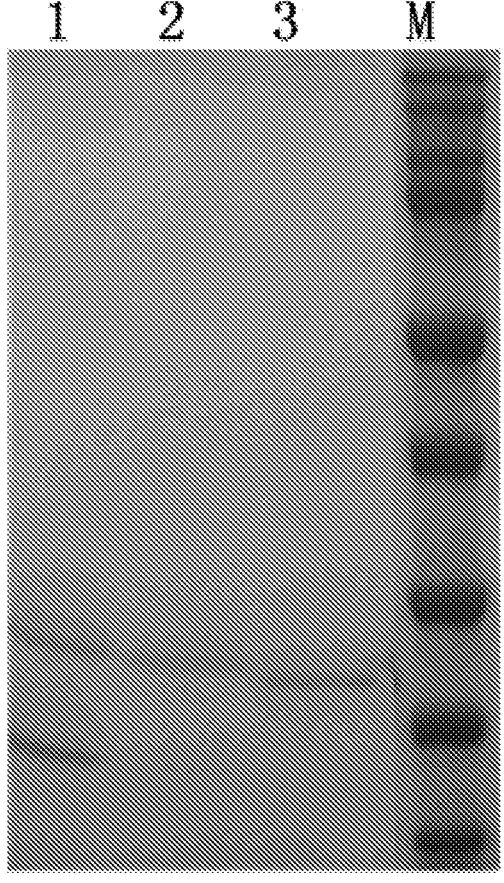
FIG. 1 shows the results of SDS-PAGE electrophoresis detection of the FGF21 peptides described herein.

The following examples describe the implementation of the present invention with specific examples. Those skilled in the art can easily understand other advantages and effects of the present invention from the content disclosed in this specification. The present application provides an FGF21 polypeptide, which has one or more of the following properties: stable structure, long half-life, low immunogenicity, high biological activity, and enhanced glucose-lowering and lipid-lowering activities.

The following examples describe the implementation of the present invention of with specific examples. Those skilled in the art can easily understand other advantages and effects of the invention of the present application from the content disclosed in this specification.

In the present application, the term "FGF21 polypeptide" generally refers to a protein encoded by fibroblast growth factor 21 (FGF21 gene, Fibroblast growth factor 21). In the present application, the FGF21 polypeptide may be human (Homo sapiens) FGF21, and the NCBI reference sequence number of its amino acid sequence is NP_061986.1. The protein encoded by the FGF21 gene is a member of the fibroblast growth factor (FGF) family and one of the endocrine subfamilies. FGF21 is the main endogenous agonist of the FGF21 receptor, which consists of the co-receptors FGF receptor 1 and β-Klotho.

In the present application, an expression of "XnY" indicates that residue X at position n in a sequence is substituted with residue Y when describing substitution of amino acid residues in the sequence. For example, amino acid substitution of "R175L" indicates that residue R at position 175 in a sequence is substituted with residue L. In the present application, the term "R19" generally refers to amino acid residue R at position 19 of the amino acid sequence of natural FGF21. In the present application, the natural FGF21 is human wild-type FGF21, and the NCBI reference sequence number of its amino acid sequence is NP_061986.1; the mature FGF21 sequence lacks a leader sequence compared to the wild-type FGF21 and contains 181 amino acids. In the present application, the term "native FGF21 sequence" generally refers to the mature human FGF21 sequence having the amino acid sequence of SEQ ID NO: 1.

In the present application, the term "immunoglobulin Fc domain" generally refers to a domain comprising the CH2 and CH3 constant region portions of an immunoglobulin (e.g., an antibody). For example, the immunoglobulin Fc domain may be a domain consisting of a hinge region, a CH2, and a CH3 constant region portion of an immunoglobulin (e.g., an antibody). For example, the immunoglobulin may be a human immunoglobulin. For example, the immunoglobulin may be a human IgG1.

In the present application, the term "functional variant" generally refers to a protein or polypeptide which is substituted, deleted, or added with one or more amino acids based on the amino acid sequence of the target protein (e.g., the FGF21 polypeptide, the fusion protein or immunoconjugate, the immunoglobulin Fc domain, or the GLP-1), but still retains at least one of the biological characteristics of the target protein. In the present application, "more" of the "one or more" amino acid substitutions generally refers to a substitution of more than one amino acid. For example, 1 to 30, 1 to 20, 1 to 10, 1 to 5, or such as 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 substitutions of amino acids. For example, the functional variant may comprise a protein or polypeptide that has been amino acid altered by at least one, for example, 1-30, 1-20, or 1-10, or for example, one, two, three, four, or five amino acid substitutions, deletions, and/or insertions. The functional variant may substantially retain the biological properties of the protein or the polypeptide prior to the change (e.g., substitution, deletion, or addition). For example, the functional variant may retain at least 60%, 70%, 80%, 90%, or 100% of the biological activity of the protein or the polypeptide prior to the change. For example, the substitution may be a conservative substitution.

In the present application, the functional variant may also be a homolog of the target protein (e.g., the FGF21 polypeptide, the fusion protein or immunoconjugate, the immunoglobulin Fc domain, or the GLP-1). In the present application, the homolog may be, for example, a protein or polypeptide having at least about 85% (for example, having at least about 85%, about 90%, about 91%, about 92%, about 93%, about 94%, about 95%, about 96%, about 97%, about 98%, about 99% or higher) sequence homology with the amino acid sequence of the target protein.

In the present application, the homology generally refers to the similarity, or association between two or more sequences. The "sequence homology percentage" can be calculated by comparing two sequences to be aligned in a comparison window to determine the number of of positions where the same nucleic acid base (for example, A, T, C, G, I) or the same amino acid residue (for example, Ala, Pro, Ser, Thr, Gly, Val, Leu, Ile, Phe, Tyr, Trp, Lys, Arg, His, Asp, Glu, Asn, Gln, Cys, and Met) are present in the two sequences to get the number of matching positions, dividing the number of matching positions by the total number of positions in the comparison window (ie, the window size), and multiplying the result by 100 to generate a sequence homology percentage. In order to determine the sequence homology percentage, the comparison can be implemented in various ways known in the art, for example, using publicly available computer software such as BLAST, BLAST-2, ALIGN or Megalign (DNASTAR) software. Those skilled in the art can determine appropriate parameters for the alignment sequences, including any algorithms needed to achieve maximum alignment within the full-length sequence range being compared or within the region of the target sequence. The homology can also be determined by the following methods: FASTA and BLAST. A description of the FASTA algorithm can be seen in W. R. Pearson and D. J. Lipman, "Improved Tools for Biological Sequence Comparison," Proceedings of the National Academy of Sciences (Proc. Natl. Acad. Sci.) 85:2444-2448, 1988; and D. J. Lipman and W. R. "Fast and Sensitive Protein Similarity Search" by Pearson, Science, 227:1435-1441, 1989. A description of the BLAST algorithm can be seen in W. Altschul, W. Gish, W. Miller, E. W. Myers and D. Lipman, "A Basic Local Alignment Search Tool", Journal of Molecular Biology, 215:403-410, 1990.

In the present application, the term "fusion protein" generally refers to a protein obtained by fusion of two or more proteins or polypeptides. In the present application, the fusion protein may include the FGF21 polypeptide. A gene or nucleic acid molecule encoding two or more proteins or polypeptides can be joined to form a fusion gene or fusion nucleic acid molecule. The fusion gene or fusion nucleic acid molecule can encode the fusion protein. The fusion protein can be artificially created by recombinant DNA techniques for biological research or therapy. In the present application, the fusion protein may further include a domain other than the FGF21 polypeptide. In the present application, the fusion protein may further include a linker connecting the FGF21 polypeptide and the domain other than the FGF21 polypeptide, and/or other domains.

In the present application, the term "linker" generally refers to a functional structure that can link two or more polypeptides by peptide bonds. In the present application, the terms "connector", "linker" and "joint" are used interchangeably. When forming the fusion protein of the invention, a linker or a connector may be used. Linkers may be composed of amino acids linked together by peptide bonds. The linker described herein can be a linker of any length or composition. In some embodiments, the linker consists of 1 to 20 amino acids linked by peptide bonds. For example, the 1 to 20 amino acids are selected from the 20 natural amino acids. In some embodiments, the 1 to 20 amino acids are selected from glycine, serine, alanine, proline, asparagine, glutamine and lysine. In some embodiments, the linker consists of multiple amino acids that are spatially unhindered. For example, the spatially unhindered amino acids can be glycine and alanine. The linker may be a G-rich polypeptide, for example, which may be selected from (G) 3-S, i.e. "GGGS", (G) 4-S, i.e. "GGGGS" and (G) 5-S, i.e. "GGGGGS". In some embodiments, the linker comprises GGGGSGGGGS, GGGGSGGGGSGGGGS or GGGGSGGGGSGGGGSA. Other suitable linkers comprise GGGGGSGGGGSGGGGS, GGGKGGGG, GGGNGSGG, GGGGGGGG, and GPNGG, etc. The linker described herein may also be non-peptide linkers. For example, an alkyl linker can be used, such as —NH—$(CH_2)S$—$C(O)$—, wherein s=2 to 20. These alkyl linkers may be further substituted with any non-sterically hindered group including, but not limited to, lower alkyl (e.g., $C_1$-$C_6$), lower acyl, halogen (e.g., Cl, Br), CN, $NH_2$ or phenyl. An exemplary non-peptidic linker can also be a polyethylene glycol linker, wherein the linker has a molecular weight of 100-5000 kD, such as 100-500 kD.

In the present application, the term "immunoconjugate" generally refers to a conjugate comprising the FGF21 polypeptide, and other components conjugated to the FGF21 polypeptide. The immunoconjugate may be a recombinant polypeptide. In the present application, the component conjugated to the FGF21 polypeptide may include a cytotoxin, a chemotherapeutic drug, an immunosuppressive agent and/ or a radioisotope, and the like. For example, examples of suitable cytotoxic and chemotherapeutic agents for forming the conjugate can be found in WO 05/103081. In the present application, the immunoconjugate may further include a linker connecting the FGF21 polypeptide and the component conjugated to the FGF21 polypeptide, and/or other domains.

In the present application, the term "GLP-1" generally refers to a peptide secreted by ileal endocrine cells. In the present application, the GLP-1 may be human GLP-1. The UniProtKB/Swiss-Prot accession number of the amino acid sequence of human GLP-1 is POC6A0.1. The GLP-1 can be used as a target for the action of type 2 diabetes drugs. GLP-1 can act on islet β cells, promote the transcription of insulin genes, insulin synthesis and secretion, and stimulate the proliferation and differentiation of islet β cells, inhibit islet β cell apoptosis, and increase the number of islet β cells.

In the present application, the term "nucleic acid molecule" generally refers to nucleotide, deoxyribonucleotide or ribonucleotide or their analogues of any length in isolated forms separated or artificially synthesized from its natural environment. The nucleic acid molecules described herein can be isolated. For example, it can be produced or synthesized by: (i) amplified in vitro, such as by polymerase chain reaction (PCR) amplification, (ii) produced by cloning and recombination, (iii) purified, such as fractionation by enzyme digestion and gel electrophoresis, or (iv) synthetic, such as by chemical synthesis. In some embodiments, the isolated nucleic acid is a nucleic acid molecule prepared by recombinant DNA technology. In the present application, nucleic acids encoding the antibodies or antigen-binding fragments thereof can be prepared by a variety of methods known in the art, including but not limited to the use of restriction fragment operation or the use of overlapping extension PCR of synthetic oligonucleotide. For specific operations, please refer to Sambrook et al., Molecular Cloning, A Laboratory Manual, Cold Spring Harbor Laboratory Press, Cold Spring Harbor, NY, 1989; and Ausube et al. Current Protocols in Molecular Biology, Greene Publishing and Wiley-Interscience, New York NY, 1993.

In the present application, the term "cell" generally refers to the individual cell, cell line or cell culture that can contain or has contained the immunoconjugate of this application, the plasmid or carrier of the nucleic acid molecule of this application, or can express the antibody or the antigen-binding fragment thereof. The cells can be prokaryotic cells (e.g. E. coli) or eukaryotic cells (e.g. yeast cells, e.g. COS cells, Chinese hamster ovary (CHO) cells, HeLa cells, HEK293 cells, COS-1 cells, NS0 cells or myeloma cells). In some embodiments, the cell is a mammalian cell. For example, the mammalian cell may be a HEK293 cell. In the present application, the term "pharmaceutical composition" usually includes the active agent in combination with an inert or active carrier, so that the composition is suitable for diagnostic or therapeutic uses, either in vivo or in vitro or ex vivo.

In the present application, the term "disease caused by metabolic disorders" generally refers to a disease caused by the accumulation or deficiency of certain metabolic substances (for example, sugar, lipid, protein, purine, etc.) due to the disturbance of a biochemical process in the body. Diseases caused by metabolic disorders described herein can be caused by congenital factors or by acquired factors. The congenital factor may include a congenital genetic defect, such as a mucoid disease. The acquired factors may include visceral pathological changes and dysfunctions, such as renal failure, nephrotic syndrome, etc.; external factors including drugs and food, such as the decrease of 25 hydroxyvitamin D in blood caused by long-term administration of antiepileptic drugs, followed by decreased calcium and phosphorus in the blood, increased alkaline phosphatase; hyperlipoproteinemia, arteriosclerosis, and gallstone disease caused by eating foods containing too much fat and/or cholesterol. In the present application, diseases caused by the metabolic disorder may include diabetes, fatty liver, obesity, and pancreatitis.

In the present application, the term "pharmaceutically acceptable adjuvant" refers to a pharmaceutically acceptable formulation carrier, solution or additive that enhances the characteristics of the formulation. Such additives are well known to those skilled in the art. Although any pharmaceutically acceptable diluent is suitable, a particularly preferred excipient for parenteral administration is a saline solution. For example, sodium chloride, mannitol, and the like. In the present application, the term "IgG constant region domain" generally refers to a polypeptide domain or a polypeptide fragment comprising an antibody heavy chain constant region, a hinge region and an antibody light chain constant region. The antibody may be an IgG antibody, for example, an antibody of the IgG1, IgG2, IgG3 or IgG4 subtype. In the present application, the term "fragment" of an IgG constant region domain generally refers to a portion of an IgG constant region domain, but still retains at least a portion of its activity. For example, the fragment may include one or more domains or fragments of CL, CHI, hinge region, CH2 and CH3.

In the present application, the "first" and "second" are only for the purpose of distinguishing the description and have no other meanings. For example, the first linker and the second linker.

In the present application, the term "comprising" generally refers to the specified features but not excluding other elements.

In the present application, the term "protein" and "polypeptide" are used interchangeably and, in their broadest sense, refer to a compound consisting of two or more amino acids, amino acid analogs or peptidomimetic subunits. The two or more subunits can be linked by peptide bonds. In some embodiments, the two or more subunits can be linked by other bonds, such as esters, ethers, amino groups, and the like. The protein or polypeptide must contain at least two amino acids and there is no limit to the maximum number of amino acids that can make up the protein or peptide sequence. In the present application, the term "amino acid"

generally refers to natural and/or unnatural or synthetic amino acids including D and L optical isomers of amino acids (such as glycine, D and L optical isomers thereof), amino acid analogs and peptide mimetics.

In the present application, the term "homology" or "identity" or "similarity" are used interchangeably and generally refer to sequence similarity between two peptides or proteins or between two nucleic acid molecules. Homology can be determined by comparing the positions in each sequence that can be aligned for comparative purposes. When the positions in the sequences of the compared molecules are occupied by the same base or amino acid, these molecules are homologous at that position. The degree of homology between sequences varies with the number of matches or homologous positions shared by the sequences. An "unrelated" or "nonhomologous" sequence indicates that there are less than 40% or 25% identities between the sequences being compared.

In the present application, when referring to the amino acid sequence identity of a polypeptide, the term "at least 80% sequence identity" generally refers to at least 80%, at least 81%, at least 82%, at least 83%, at least 84%, at least 85%, at least 86%, at least 87%, at least 88%, at least 89%, at least 90% %, at least 91%, at least 92%, at least 93%, at least 94%, at least 95%, at least 96%, at least 97%, at least 98% or at least 99% sequence identity to each reference sequence.

In the present application, when used in connection with a numerical value, the term "about" generally include numerical values in the range having a lower limit of 5% less than the indicated value and an upper limit of 5% greater than the indicated value.

In the present application, the term "composition" generally refers to a combination of two or more substances, for example, a combination of the active agent with other inert or active compounds.

In the present application, the term "therapeutically effective amount" generally refers to the minimum dose of active ingredient required to produce a therapeutic benefit in a subject. For example, for a patient exhibiting or susceptible to type II diabetes, obesity, or metabolic syndrome, or for preventing the onset of the disease, "therapeutically effective amount" refers to a dose that is capable of inducing, ameliorating, or causing a pathological condition, disease progression, or physiological condition that is associated with or counteracted by the disorder described above.

In the present application, the term "subject" or "patient" may be human, but may also be a non-human animal, more specifically may be a companion animal (such as a dog, a cat or the like), a farm animal such as (a cow, a sheep, a pig, horses or the like), or laboratory animals (such as rats, mice, guinea pigs, and the like), etc.

FGF21 Polypeptide

In one aspect, the FGF21 polypeptide, which comprises amino acid substitutions at the following positions: L98, S167, P171, R175, and R19, as compared to the amino acid sequence shown in SEQ ID NO: 1. In the present application, the L98, S167, P171 and R175 may refer to residue L at position 98, residue S at position 167, residue P at position 171, and residue R at position 175 of the amino acid sequence shown in SEQ ID NO: 1 respectively.

In the present application, the FGF21 polypeptide further comprises amino acid substitutions at one or more positions selected from the following group consisting of: R135, A180, A31, and G43. In the present application, the R135, A180, A31 and G43 may refer to residue R at position 135, residue A at position 180, residue A at position 31, and residue G at position 43 of the amino acid sequence shown in SEQ ID NO: 1 respectively.

In the present application, the FGF21 polypeptide comprises amino acid substitutions at amino acid residues selected from the group consisting of: (1) L98, S167, P171, R175 and R19; (2) L98, S167, P171, R175, R19 and R135; (3) L98, S167, P171, R175, R19 and A180; (4) L98, S167, P171, R175, R19, and Q173; (5) L98, S167, P171, R175, R19, A31, and G43; (6) L98, S167, P171, R175, R19, R135, and Q173; and, (7) L98, S167, P171, R175, R19, R135, A31, and G43, as compared to the amino acid sequence shown in SEQ ID NO: 1.

In the present application, the amino acid substitution of the FGF21 polypeptide at L98 may be L98R.

In the present application, the amino acid substitution of the FGF21 polypeptide at S167 may be S167H.

In the present application, the amino acid substitution of the FGF21 polypeptide at P171 may be P171A, P171G and P171N.

In the present application, the amino acid substitution of the FGF21 polypeptide at R175 may be R175L.

In the present application, the amino acid substitution of the FGF21 polypeptide at R19 may be R19V.

In the present application, the FGF21 polypeptide further comprises one or more amino acid substitutions selected from the following group consisting of: R135V, A180E, A31C, and G43C. In the present application, the R135V, A180E, A31C and G43C may respectively refer to that residue R at position 135 may be substituted by residue V, residue A at position 180 may be substituted by residue E, residue A at position 31 may be substituted by residue C, and residue G at position 43 may be substituted by residue C of the amino acid sequence shown in SEQ ID NO:1.

In the present application, the FGF21 polypeptide comprises amino acid substitutions selected from the group consisting of: (1) L98R, S167H, P171A, R175L and R19V; (2) L98R, S167H, P171G, R175L and R19V; (3) L98R, S167H, P171G, R175L, R19V and R135V; (4) L98R, S167H, P171G, R175L, R19V, and A180E; (5) L98R, S167H, P171A, R175L, R19V, and R135V; (6) L98R, S167H, P171A, R175L, R19V, A31C, and G43C; (7) L98R, S167H, P171G, R175L, R19V, A31C and G43C; (8) L98R, S167H, P171G, R175L, R19V, R135V, A31C and G43C; (9) L98R, S167H, P171A, R175L, R19V, R135V, A31C and G43C; and, (10) L98R, S167H, P171A, R175L, R19V and A180E, as compared to the amino acid sequence shown in SEQ ID NO: 1.

In the present application, the FGF21 polypeptide comprises the amino acid sequence shown in any one of the following groups: SEQ ID NOs: 2 to 11.

For example, the FGF21 polypeptide described herein may include amino acid substitutions of L98R, S167H, P171A, R175L, and R19V as compared to the amino acid sequence shown in SEQ ID NO: 1. For example, the polypeptide comprising amino acid substitutions of L98R, S167H, P171A, R175L, and R19V may be FGF21-1, and its sequence may be shown in SEQ ID NO:2.

As another example, the FGF21 polypeptide described herein may include amino acid substitutions of L98R, S167H, P171G, R175L, and R19V as compared to the amino acid sequence shown in SEQ ID NO: 1. For example, the polypeptide comprising amino acid substitutions of L98R, S167H, P171G, R175L, and R19V may be FGF21-2, and its sequence may be shown in SEQ ID NO: 3.

As another example, the FGF21 polypeptide described herein may include amino acid substitutions of L98R, S167H, P171G, R175L, R19V and R135V as compared to the amino acid sequence shown in SEQ ID NO: 1. For example, the polypeptide comprising amino acid substitutions of L98R, S167H, P171G, R175L, R19V and R135V may be FGF21-3, and its sequence may be shown in SEQ ID NO:4.

As another example, the FGF21 polypeptide described herein may include amino acid substitutions of L98R, S167H, P171G, R175L, R19V and A180E as compared to the amino acid sequence shown in SEQ ID NO: 1. For example, the polypeptide comprising amino acid substitutions of L98R, S167H, P171G, R175L, R19V and A180E may be FGF21-4, and its sequence may be shown in SEQ ID NO:5.

As another example, the FGF21 polypeptide described herein may include amino acid substitutions of L98R, S167H, P171N, R175L, R19V and Q173T as compared to the amino acid sequence shown in SEQ ID NO: 1. For example, the polypeptide comprising amino acid substitutions of L98R, S167H, P171N, R175L, R19V and Q173T may be FGF21-5.

As another example, the FGF21 polypeptide described herein may include amino acid substitutions of L98R, S167H, P171A, R175L, R19V and R135V as compared to the amino acid sequence shown in SEQ ID NO: 1. For example, the polypeptide comprising amino acid substitutions of L98R, S167H, P171A, R175L, R19V and R135V may be FGF21-6, and its sequence may be shown in SEQ ID NO:6.

As another example, the FGF21 polypeptide described herein may include amino acid substitutions of L98R, S167H, P171A, R175L, R19V and G43C as compared to the amino acid sequence shown in SEQ ID NO: 1. For example, the polypeptide comprising amino acid substitutions of L98R, S167H, P171A, R175L, R19V and G43C may be FGF21-7, and its sequence may be shown in SEQ ID NO:7.

As another example, the FGF21 polypeptide described herein may include amino acid substitutions of L98R, S167H, P171N, R175L, R19V, R135V and Q173T as compared to the amino acid sequence shown in SEQ ID NO: 1. For example, the polypeptide comprising amino acid substitutions of L98R, S167H, P171N, R175L, R19V, R135V and Q173T may be FGF21-8.

As another example, the FGF21 polypeptide described herein may include amino acid substitutions of L98R, S167H, P171G, R175L, R19V, A31C and G43C compared to the amino acid sequence shown in SEQ ID NO: 1. For example, the polypeptide comprising amino acid substitutions of L98R, S167H, P171G, R175L, R19V, A31C and G43C may be FGF21-9, and its sequence may be shown in SEQ ID NO:8.

As another example, the FGF21 polypeptide described herein may include amino acid substitutions of L98R, S167H, P171G, R175L, R19V, R135V, A31C and G43C as compared to the amino acid sequence shown in SEQ ID NO: 1. For example, the polypeptide comprising amino acid substitutions of L98R, S167H, P171G, R175L, R19V, R135V, A31C and G43C may be FGF21-10, and its sequence may be shown in SEQ ID NO:9.

As another example, the FGF21 polypeptide described herein may include amino acid substitutions of L98R, S167H, P171A, R175L, R19V, R135V, A31C and G43C compared to the amino acid sequence shown in SEQ ID NO: 1. For example, the polypeptide comprising amino acid substitutions of L98R, S167H, P171A, R175L, R19V, R135V, A31C and G43C may be FGF21-11, and its sequence may be shown in SEQ ID NO:10.

As another example, the FGF21 polypeptide described herein may include amino acid substitutions of L98R, S167H, P171A, R175L, R19V and A180E as compared to the amino acid sequence shown in SEQ ID NO: 1. For example, the polypeptide comprising amino acid substitutions of L98R, S167H, P171A, R175L, R19V and A180E may be FGF21-12, and its sequence may be shown in SEQ ID NO:11.

Fusion Protein or Immunoconjugate

In another aspect, the present application provides a fusion protein or immunoconjugate comprising the FGF21 polypeptide described herein.

a. Fc

In the present application, the fusion protein or immunoconjugate further comprises an immunoglobulin Fc domain. In the present application, the immunoglobulin Fc domain is located at the C-terminus of the FGF21 polypeptide.

Among the fusion protein or immunoconjugate described herein, the immunoglobulin Fc domain is an Fc of human IgG or a functional variant thereof. For example, the immunoglobulin Fc domain comprises the amino acid sequence shown in any one of the following groups: SEQ ID NOs: 12 to 13.

For example, the immunoglobulin Fc domain described herein may be the Fc of human IgG (referring to the protein with accession number P01861.1 in UniProt KB or Swiss-Prot). The Fc of the human IgG may comprise the amino acid sequence shown in SEQ ID NO: 12.

In the present application, the immunoglobulin Fc domain is an Fc of human IgG or a functional variant thereof. For example, the functional variant of the FC of human IgG may be a polypeptide or protein obtained by modifying a specific amino acid residue with a natural or unnatural amino acid based on the amino acid sequence of the FC of the human IgG1. For example, the modification may be generated based on the insertion, substitution, or deletion of one or more conserved or non conserved amino acids at a specific location, or may also include the modification of introducing a non amino acid structure at a specific location.

For example, the functional variant of the immunoglobulin Fc domain may be IgG-Fc-PAAK, which may include the amino acid sequence shown in SEQ ID NO: 13. The IgG-Fc-PAAK may include mutations of S228P, F234A, L235A, and R409K, and deletion of K447. For example, compared to the amino acid sequence shown in SEQ ID NO: 12, residue S at position 228 of the IgG-Fc-PAAK may be replaced by residue P, and residue F at position 234 may be replaced by residue A, residue L at position 235 may be replaced by residue A, residue L at position 235 may be replaced by residue A, and residue K at position 447 may be deleted.

b. Linker

In the present application, the fusion protein may further include a linker. In the present application, the linker may be a peptide linker. In the present application, wherein the N-terminus of the linker is connected to the C-terminus of the immunoglobulin Fc domain, and the C-terminus of the linker is connected to the N-terminus of the FGF21 polypeptide. In the present application, the linker comprises the amino acid sequence shown in SEQ ID NO: 16.

In the present application, the linker may comprise a first linker and a second linker. For example, the N-terminus of the first linker is connected to the C-terminus of the immunoglobulin Fc domain, and the C-terminus of the first linker is connected to the N-terminus of the FGF21 polypeptide. For another example, the N-terminus of the second linker is connected to the C-terminus of the GLP-1 or the variant thereof, and the C-terminus of the second linker is connected to the N-terminus of the immunoglobulin Fc domain. In the present application, the first linker and/or the second linker may comprise the amino acid sequence shown in SEQ ID NO: 16.

c. GLP-1

In the present application, the fusion protein may further comprise GLP-1 or a functional variant thereof. In the present application, the GLP-1 or the functional variant thereof comprises the amino acid sequence shown in any one of the following groups: SEQ ID NOs: 14 to 15.

In the present application, the GLP-1 or the functional variant thereof may be human GLP-1 (its accession number is POC6A0.1 in UniProt KB or Swiss-Prot). The GLP-1 may also be a functional variant of human GLP-1.

For example, the functional variant of human GLP-1 may be GLP-1-GEG, which may include the amino acid sequence shown in SEQ ID NO: 15. For example, the GLP-1-GEG may include mutations of A8G, G22E, and R36G. For example, the residue A at position 8 of the GLP-1-GEG may be replaced by residue G, the residue G at position 22 may be replaced by residue E, and the residue R at position 36 may be replaced by residue G, as compared to the amino acid sequence shown in SEQ ID NO: 14.

d. Fusion Protein

Single-Target Fusion Protein

In the present application, the fusion protein may be a single-target fusion protein (in this application, it may be simply referred to as "single-target"), that is, the fusion protein may include the FGF21 polypeptide.

In the present application, the single-target fusion protein or immunoconjugate further comprises an immunoglobulin Fc domain. In the present application, the immunoglobulin Fc domain is located at the C-terminus of the FGF21 polypeptide. In the present application, the immunoglobulin Fc domain is an Fc of human IgG or a functional variant thereof. In the present application, the immunoglobulin Fc domain comprises the amino acid sequence shown in any one of the following groups: SEQ ID NOs: 12 to 13.

In the present application, the single-target fusion protein or immunoconjugate may further comprise a linker. In the present application, the linker may be a peptide linker. In the present application, wherein the N-terminus of the linker is connected to the C-terminus of the immunoglobulin Fc domain, and the C-terminus of the linker is connected to the N-terminus of the FGF21 polypeptide. In the present application, the linker comprises the amino acid sequence shown in SEQ ID NO: 16.

In the present application, the single-target fusion protein or immunoconjugate comprises the amino acid sequence shown in any one of the following groups: SEQ ID NOs: 17 to 26.

In the present application, the single-target fusion protein may be an immunoglobulin Fc domain, a linker, and an FGF21 polypeptide from the N-terminus to the C-terminus, respectively.

For example, the single-target fusion protein described herein may be single-target 1 #(which may include the amino acid sequence show in SEQ ID NO:17), which may include the FGF21 polypeptide FGF21-1.

For example, the single-target fusion protein described herein may be single-target 2 #(which may include the amino acid sequence shown in SEQ ID NO:18), which may include the FGF21 polypeptide FGF21-2.

For example, the single-target fusion protein described herein may be single-target 3 #(which may include the amino acid sequence shown in SEQ ID NO:19), which may include the FGF21 polypeptide FGF21-3.

For example, the single-target fusion protein described herein may be single-target 4 #(which may include the amino acid sequence shown in SEQ ID NO:20), which may include the FGF21 polypeptide FGF21-4.

For example, the single-target fusion protein described herein may be single-target 5 #, which may include the FGF21 polypeptide FGF21-5.

For example, the single-target fusion protein described herein may be single-target 6 #(which may include the amino acid sequence shown in SEQ ID NO:21), which may include the FGF21 polypeptide FGF21-6.

For example, the single-target fusion protein described herein may be single-target 7 #(which may include the amino acid sequence shown in SEQ ID NO:22), which may include the FGF21 polypeptide FGF21-7.

For example, the single-target fusion protein described herein may be single-target 8 #, which may include the FGF21 polypeptide FGF21-8.

For example, the single-target fusion protein described herein may be single-target 9 #(which may include the amino acid sequence shown in SEQ ID NO:23), which may include the FGF21 polypeptide FGF21-9.

For example, the single-target fusion protein described herein may be single-target 10 #(which may include the amino acid sequence shown in SEQ ID NO:24), which may include the FGF21 polypeptide FGF21-10.

For example, the single-target fusion protein described herein may be single-target 11 #(which may include the amino acid sequence shown in SEQ ID NO:25), which may include the FGF21 polypeptide FGF21-11.

For example, the single-target fusion protein described herein may be single-target 12 #(which may include the amino acid sequence shown in SEQ ID NO:26), which may include the FGF21 polypeptide FGF21-12.

In the present application, the single-target fusion protein may further include other modifications. For example, the modification may include substitution, addition, or deletion of one or more amino acids, as long as the single-target fusion protein still contains FGF21 or a variant thereof of the present application.

For example, the modified single-target fusion protein may be a single-target RGHLQQ (which may include the amino acid sequence shown in SEQ ID NO: 45), a single-target RAHL (which may include the amino acid sequence shown in SEQ ID NO: 46), a single target RGHL (which may include the amino acid sequence shown in SEQ ID NO: 47), a single target RGE (which may include the amino acid sequence shown in SEQ ID NO: 48).

Dual Target Fusion Protein

In the present application, the fusion protein may also be a dual-target fusion protein (in this application, it may be simply referred to as a "dual-target"), that is, the fusion protein may contain at least two or more domains. For example, it contains the FGF21 polypeptide, and it can also contain GLP-1 or functional variants thereof. In the present application, the dual-target fusion protein may further contain an immunoglobulin Fc domain or a functional variant thereof.

In the present application, the dual-target fusion protein may further include a linker. In the present application, the linker may be a peptide linker. In the present application, the linker may include a first linker and a second linker. For example, the N-terminus of the first linker is connected to the C-terminus of the immunoglobulin Fc domain, and the C-terminus of the first linker is connected to the N-terminus of the FGF21 polypeptide. For another example, the N-terminus of the second linker is connected to the C-terminus of the GLP-1 or the variant thereof, and the C-terminus of the second linker is connected to the N-terminus of the immunoglobulin Fc domain. In the present application, the first linker and/or the second linker may comprise the amino acid sequence shown in SEQ ID NO: 16.

In the present application, the dual-target fusion protein may be the FGF21 polypeptide, the first linker, the immunoglobulin Fc domain, the second linker, and the GLP-1 or the functional variant thereof from the N-terminus to the C-terminus, respectively. Wherein, the FGF21 polypeptide may include the amino acid sequence selected from any one of the following groups: SEQ ID NO: 2 to 11 or FGF21-1 to FGF21-12; the immunoglobulin Fc domain may include the amino acid sequence selected from any one of the following groups: SEQ ID NO: 12 to 13; the GLP-1 or the functional variant thereof may include the amino acid sequence selected from any one of the following groups: SEQ ID NO: 14 to 15; the first linker and/or the second linker may include the amino acid sequence shown in SEQ ID NO: 16.

For example, the dual-target fusion protein described in this application may be dual-target 1 #, which may include the amino acid sequence shown in SEQ ID NO: 27, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-1 (which may include the amino acid sequence shown in SEQ ID NO: 2) from the N-terminus to the C-terminus respectively.

For another example, the dual-target fusion protein described in this application may be dual-target 2 #, which may include the amino acid sequence shown in SEQ ID NO: 28, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-2 (which may include the amino acid sequence shown in SEQ ID NO: 3) from the N-terminus to the C-terminus respectively.

For another example, the dual-target fusion protein described in this application may be dual-target 3 #, which may include the amino acid sequence shown in SEQ ID NO: 29, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-3 (which may include the amino acid sequence shown in SEQ ID NO: 4) from the N-terminus to the C-terminus respectively.

For another example, the dual-target fusion protein described in this application may be dual-target 4 #, which may include the amino acid sequence shown in SEQ ID NO: 30, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-4 (which may include the amino acid sequence shown in SEQ ID NO: 5) from the N-terminus to the C-terminus respectively.

For another example, the dual-target fusion protein described in this application may be dual-target 5 #, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-5 from the N-terminus to the C-terminus respectively.

For another example, the dual-target fusion protein described in this application may be dual-target 6 #, which may include the amino acid sequence shown in SEQ ID NO: 31, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-6 (which may include the amino acid sequence shown in SEQ ID NO: 6) from the N-terminus to the C-terminus respectively.

For another example, the dual-target fusion protein described in this application may be dual-target 7 #, which may include the amino acid sequence shown in SEQ ID NO: 32, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-7 (which may include the amino acid sequence shown in SEQ ID NO: 7) from the N-terminus to the C-terminus respectively.

For another example, the dual-target fusion protein described in this application may be dual-target 8 #, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-8 from the N-terminus to the C-terminus respectively.

For another example, the dual-target fusion protein described in this application may be dual-target 9 #, which may include the amino acid sequence shown in SEQ ID NO: 33, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-9 (which may include the amino acid sequence shown in SEQ ID NO: 8) from the N-terminus to the C-terminus respectively.

For another example, the dual-target fusion protein described in this application may be dual-target 10 #, which may include the amino acid sequence shown in SEQ ID NO: 34, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-10 (which may include the amino acid sequence shown in SEQ ID NO: 9) from the N-terminus to the C-terminus respectively.

For another example, the dual-target fusion protein described in this application may be dual-target 11 #, which may include the amino acid sequence shown in SEQ ID NO: 35, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-11 (which may include the amino acid sequence shown in SEQ ID NO: 10) from the N-terminus to the C-terminus respectively.

For another example, the dual-target fusion protein described in this application may be dual-target 12 #, which may include the amino acid sequence shown in SEQ ID NO: 36, which may be GLP-1-GEG (which may include the amino acid sequence shown in SEQ ID NO: 15), the first linker (which may include the amino acid sequence shown in SEQ ID NO: 16), IgG-Fc-PAAK (which may include the amino acid shown in SEQ ID NO: 13), the second linker (which may include the amino acid sequence shown in SEQ ID NO: 16) and FGF21-12 (which may include the amino acid sequence shown in SEQ ID NO: 11) from the N-terminus to the C-terminus respectively.

In the present application, the dual-target fusion protein may also be a dual-target RAHL, which may include the amino acid sequence shown in SEQ ID NO: 41; the dual-target fusion protein described herein may also be a dual-target RGHL, which may include the amino acid sequence shown in SEQ ID NO: 42; the dual-target fusion protein described herein may also be a dual-target RGHLQQ, which may include the amino acid sequence shown in SEQ ID NO: 43; the dual-target fusion protein described herein may also be a dual target RAHLQQ, which may include the amino acid sequence shown in SEQ ID NO: 44.

In the present application, the target protein (for example, the FGF21 polypeptide, the fusion protein or immunoconjugate, the immunoglobulin Fc domain, or the GLP-1) may include a functional variant and/or a homologue thereof.
Nucleic Acid Molecules, Vectors, Cells, Pharmaceutical Compositions In another aspect, the application provides an isolated nucleic acid molecule encoding the FGF21 polypeptide described herein or the fusion protein or immunoconjugate described herein. For example, it can be produced or synthesized by: (i) amplified in vitro, such as by polymerase chain reaction (PCR) amplification, (ii) produced by cloning and recombination, (iii) purified, such as fractionation by enzyme digestion and gel electrophoresis, or (iv) synthetic, such as by chemical synthesis. In the present application, the isolated nucleic acid is a nucleic acid molecule prepared by recombinant DNA technology.

In another aspect, provided herein is a vector comprising the isolated nucleic acid molecule described herein. In addition, the vector may contain other genes, such as a marker gene that allows selection of the vector in an appropriate host cell and under appropriate conditions. In addition, the vector may also contain expression control elements that allow the coding region to be properly expressed in an appropriate host. Such control elements are well known to those skilled in the art, and may include, for example, promoters, ribosome binding sites, enhancers, and other control elements that regulate gene transcription or mRNA translation. In the present application, the expression control sequence is an adjustable element. The specific structure of the expression control sequence may vary according to the function of the species or cell type, but usually includes 5' non-transcribed sequences and 5' and 3' non-translated sequences respectively involved in transcription and translation initiation, such as TATA box, Cap sequences, CAAT sequences, etc. For example, the 5' non-transcribed expression control sequence may comprise a promoter region, and the promoter region may comprise a promoter sequence for transcriptionally controlling a functionally linked nucleic acid. One or more nucleic acid molecules described herein may be operably linked to the expression control element. The vectors may include, for example, plasmids, cosmids, viruses, phages, or other vectors commonly used in, for example, genetic engineering. For example, the vector is an expression vector.

In another aspect, provided herein is a cell comprising or expressing the FGF21 polypeptide described herein, the fusion protein or immunoconjugate described herein, the isolated nucleic acid molecule described herein or the vector described herein. It contains the fusion protein, the immunoconjugate, the nucleic acid molecule, or the carrier. In the present application, each kind or each cell may comprise one or one of the vectors described herein. In the present application, each kind or each cell may include a plurality (for example, 2 or more) or a plurality kind (for example, 2 or more) of the vectors described herein. For example, the vectors described herein can be introduced into the cells, such as eukaryotic cells (e.g., mammalian cells). For example, the mammalian cell may be a HEK293 cell. The vectors described herein can be introduced into the cells by methods known in the art, such as electroporation, lipofectine transfection, lipofectamin transfection, and the like.

Pharmaceutical Composition and Use Thereof

In another aspect, provided herein is a pharmaceutical composition comprising the FGF21 polypeptide described herein, the fusion protein or immunoconjugate described herein, the isolated nucleic acid molecule described herein, the vector described herein, or the cell described herein, and optionally a pharmaceutically acceptable adjuvant.

The pharmaceutically acceptable adjuvant may include a buffer, an antioxidant, a preservative, a low molecular weight polypeptide, a protein, a hydrophilic polymer, an amino acid, a sugar, a chelator, a counter ion, a metal complex, and/or a non-ionic surfactant, etc.

In the present application, the pharmaceutical composition can be prepared for oral administration, intravenous administration, intramuscular administration, in situ administration at tumor site, inhalation, rectal administration, vaginal administration, percutaneous administration or administration via subcutaneous depots.

In another aspect, provided herein is the use of the FGF21 polypeptide described herein, the fusion protein or the immunoconjugate described herein in the manufacture of medicines for the treatment of diseases caused by FGF21 metabolic disorders.

For example, the pharmaceutical composition of the present application can inhibit or delay the development or progression of a disease, and/or can reduce and/or stabilize the disease state.

The pharmaceutical composition described herein may include a therapeutically effective amount of the FGF21 polypeptide, fusion protein, or immunoconjugate. The therapeutically effective amount is the dose capable of preventing and/or treating (at least partially treating) diseases or disorders (such as those caused by metabolic disorders of FGF21) and/or any complications thereof in subjects with or at risk of development.

In another aspect, the present application provides a method for treating diseases caused by metabolic disorders of FGF21, which comprises administering the FGF21 polypeptide, fusion protein or immunoconjugate of the present application to the subject.

In another aspect, provided is the FGF21 polypeptide, the fusion protein or the immunoconjugate described herein in the manufacture of medicines for the treatment of diseases caused by FGF21 metabolic disorders.

In the present application, diseases caused by the metabolic disorder of FGF21 may include diabetes, fatty liver, obesity, and pancreatitis.

Without intending to be bound by any theory, the following examples are merely for explaining the working method of the chimeric antigen receptor, vector, cell, and composition of the present application, and are not intended to limit the scope of the invention of the present application.

EXAMPLE

Example 1 Preparation of FGF21 Polypeptide 1.1 Construction of Expression Vector Plasmid-X Suzhou GENEWIZ Biotechnology Co., Ltd. was entrusted to synthesize the target gene, including FGF21-1 (its amino acid sequence is shown in SEQ ID NO:2), FGF21-7 (its amino acid sequence is shown in SEQ ID NO: 7), and FGF21-RHAL (compared with the amino acid sequence shown in SEQ ID NO: 1, the amino acid substitution at L98 is L98R, the amino acid substitution at S167 is S167H, the amino acid substitution at P171 is P171A, and the amino acid substitution at R175 is R175L). The target gene sequence and vector plasmid pXC17.4 were digested with the endonucleases HindIII and EcoR I (TAKARA, Japan) at 37° C. The digestive product was purified and recovered using Gel Extraction Kit according to the manufacturer's instructions. The purified objective gene was ligated with the vector using the DNA Ligation Kit Ver.2.1 (TAKARA, Japan) according to the manufacturer's instructions, which was then incubated at 16° C. for 1 hour to obtain a recombinant expression plasmid.

The above recombinant expression plasmid was transformed into competent cells DH5a, and bacteria was coated into an ampicillin plate. The monoclonal on the plate was picked and cultured in 1 ml of LB medium (peptone 10 g/L, yeast extract 5 g/L, sodium chloride 10 g/L and agar 2%, the content of antibiotic 100 μg/mL) to extract the plasmid. After sequencing and validation by Suzhou GENEWIZ Biotechnology Co., Ltd., a series of validated correct expression vectors were extracted with Invitrogen Plasmid Kit and digested with restriction enzyme PvuI (TAKARA, Japan). After linearization, the product was purified and recovered by ethanol precipitation method and stored at –20° C. for future use.

1.2 Transfection of the Vector and Expression in Cells

After CHO host cells were resuscitated with Cellvento CHO-200 medium (Merck), cells were collected for transfection when the cell density was approximately $4.76 \times 10^6$ cells/mL. The transfected cells were about $1 \times 10^7$ cells and plasmids were about 40 μg, which were transfected by electric shock (Bio-Rad, gene pulser Xcell). Cells were cultured in 20 mL of Cellvento CHO-200 medium after electric shock. On the second day of culture, cells were collected by centrifugation and resuspended in 20 mL of Cellvento CHO-200 medium added with L-Methionine sulfoximine (Sigma-aldrich) to a final concentration of 50 μM. When the cell density was about $0.6 \times 10^6$ cells/mL, the obtained mixed clones were passaged with Cellvento CHO-200 medium, and the density of passage cell was about $0.2 \times 10^6$ cells/mL. When the cell viability was about 90%, the cell culture fluid was collected.

1.3 Purification and Detection of Fusion Proteins

The cell culture solution was centrifuged at 200 g for 10 min. Then the supernatant was centrifuged at 8000 rpm for 30 min. The supernatant was collected. The supernatant of the cell culture solution after centrifugation was subjected to affinity purification by using Ni-charged MagBeads (L00295, Kingsray) and Am Mag MR magnetic frame (L00723, Kingsray). The equilibrium solution was 20 mM PBS, 0.5 M NaCl, pH 7.4; the eluent was 20 mM PBS, 0.5 M NaCl, 0.5 M imidazole buffer of pH 7.4. The protein eluate sample under the target absorption peak was collected. At the same time, the collected sample was detected by 10% SDS-PAGE electrophoresis after reduction treatment. The SDS test results are shown in Table 1 and FIG. 1.

TABLE 1

| Analysis of the test results of SDS-PAGE electrophoresis of FGF21 polypeptides | | |
|---|---|---|
| Mutant | Fermentation for 7 days Percentage of purity | Fermentation for 7 days Percentage of FGF21 degradation at the 19th position |
| FGF21-RAHL | Less than 80% | More than 20% |
| FGF21-1 | More than 90% | About 0% |
| FGF21-7 | More than 90% | About 0% |

Example 2: Preparation of Dual Target Fusion Protein

Figure 2:
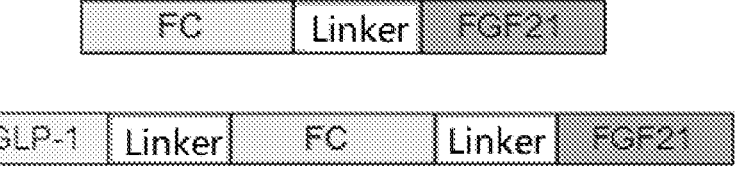
FIG. 2 shows a structure diagram of the fusion protein described herein.

The fusion protein described in this application includes a single-target fusion protein and a dual-target fusion protein, and their structures are shown in FIG. 2.

2.1 Construction of Expression Vector Plasmid-X2

Suzhou GENEWIZ Biotechnology Co., Ltd. was entrusted to synthesize the target gene, including double-target 1 #(its amino acid sequence is shown in SEQ ID NO:27), double target 2 #(its amino acid sequence is shown in SEQ ID NO: 28), double target 3 #(its amino acid sequence is shown in SEQ ID NO:29), double target 4 #(its amino acid sequence is shown in SEQ ID NO:30), double target 5 #, double target 6 #(its amino acid sequence is shown in SEQ ID NO:31), double target 7 #(its amino acid sequence is shown in SEQ ID NO:32), double target 8 #, double target 9 #(its amino acid sequence is shown in SEQ ID NO:33), double target 10 #(its amino acid sequence is shown in SEQ ID NO: 34), double target 11 #(its amino acid sequence is shown in SEQ ID NO: 35), and double target 12 #(its amino acid sequence is shown in SEQ ID NO:36).

The sequence of the objective gene and the vector plasmid pXC17.4 were digested with the endonuclease HindIII and EcoRI (TAKARA, Japan) at 37° C., and the digested product was purified and recovered by using a Gel Extraction Kit according to the manufacturer's instructions. The purified objective gene was ligated with the vector using a DNA Ligation Kit Ver.2.1 (TAKARA, Japan) according to the manufacturer's instructions and incubated at 16° C. for 1 hour to obtain a recombinant expression plasmid.

The above recombinant expression plasmid was transformed into competent cells DH5a, and bacteria was coated into an ampicillin plate. The monoclonal on the plate was picked and cultured in 1 ml of LB medium (peptone 10 g/L, yeast extract 5 g/L, sodium chloride 10 g/L and agar 2%, the content of antibiotic 100 μg/mL) to extract the plasmid. After sequencing and validation by Guangzhou IGE Biotechnology Co., Ltd., a series of validated correct expression vectors were extracted with Invitrogen Plasmid Kit and digested with restriction enzyme PvuI (TAKARA, Japan). After linearization, the product was purified and recovered by ethanol precipitation method and stored at −20° C. for future use.

2.2 Transfection of the Vector and Expression in Cells

After CHO host cells were resuscitated with Cellvento CHO-200 medium (Merck), cells were collected for transfection when the cell density was approximately $4.76 \times 10^6$ cells/mL. The transfected cells were about $1 \times 10^7$ cells and plasmids were about 40 μg, which were transfected by electric shock (Bio-Rad, gene pulser Xcell). Cells were cultured in 20 mL Cellvento CHO-200 medium after electric shock. On the second day of culture, cells were collected by centrifugation and resuspended in 20 mL of Cellvento CHO-200 medium added with L-Methionine sulfoximine (Sigma-aldrich) to a final concentration of 50 μM. When the cell density was about $0.6 \times 10^6$ cells/mL, the obtained mixed clones were passaged with Cellvento CHO-200 medium. The density of passage cell was about $0.2 \times 10^6$ cells/mL. When the cell viability was about 90%, the cell culture fluid was collected.

2.3 Purification and Detection of Fusion Proteins

Figure 3A:
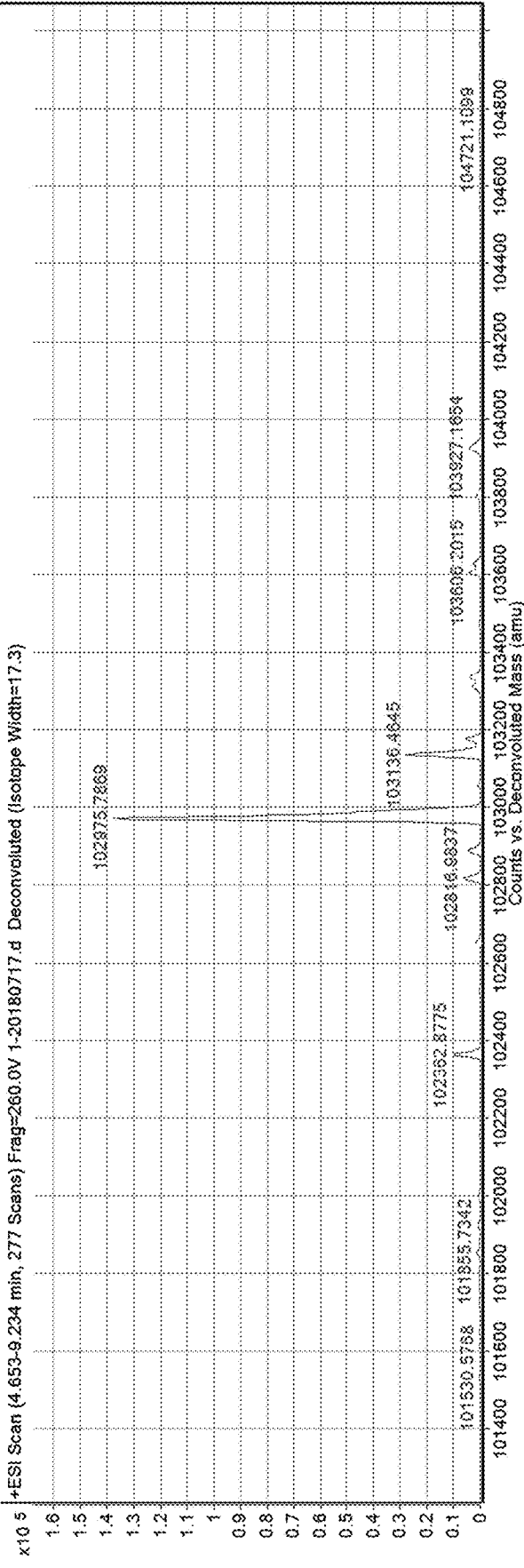
FIGS. 3A-3H show mass spectrometry detection diagrams of the fusion proteins described herein.
Figure 3B:
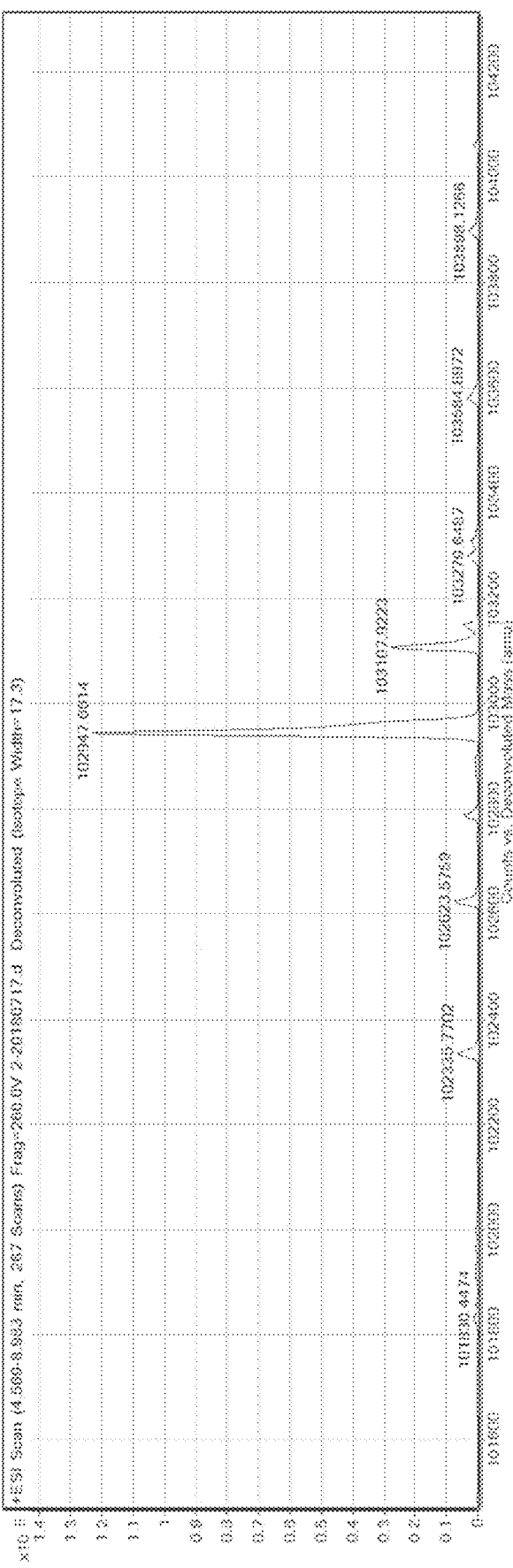
Figure 3C:
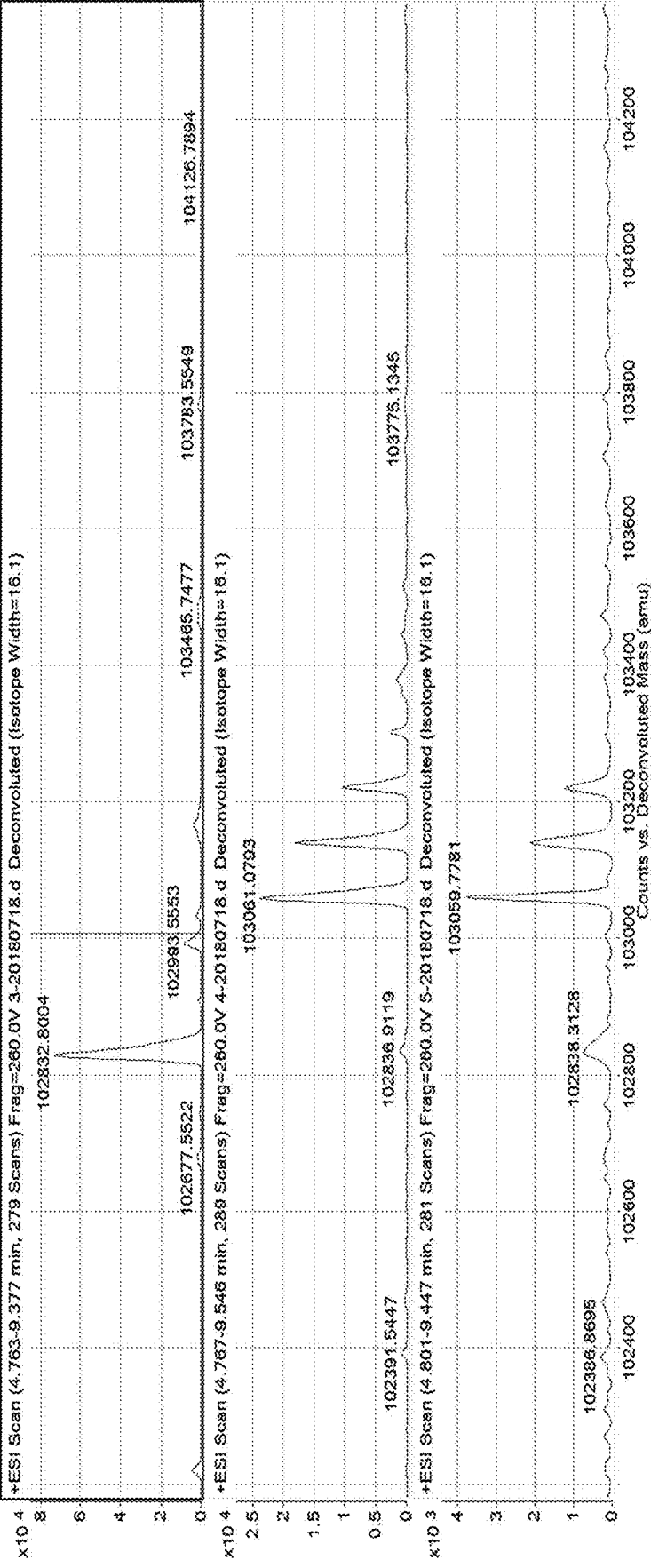
Figure 3D:
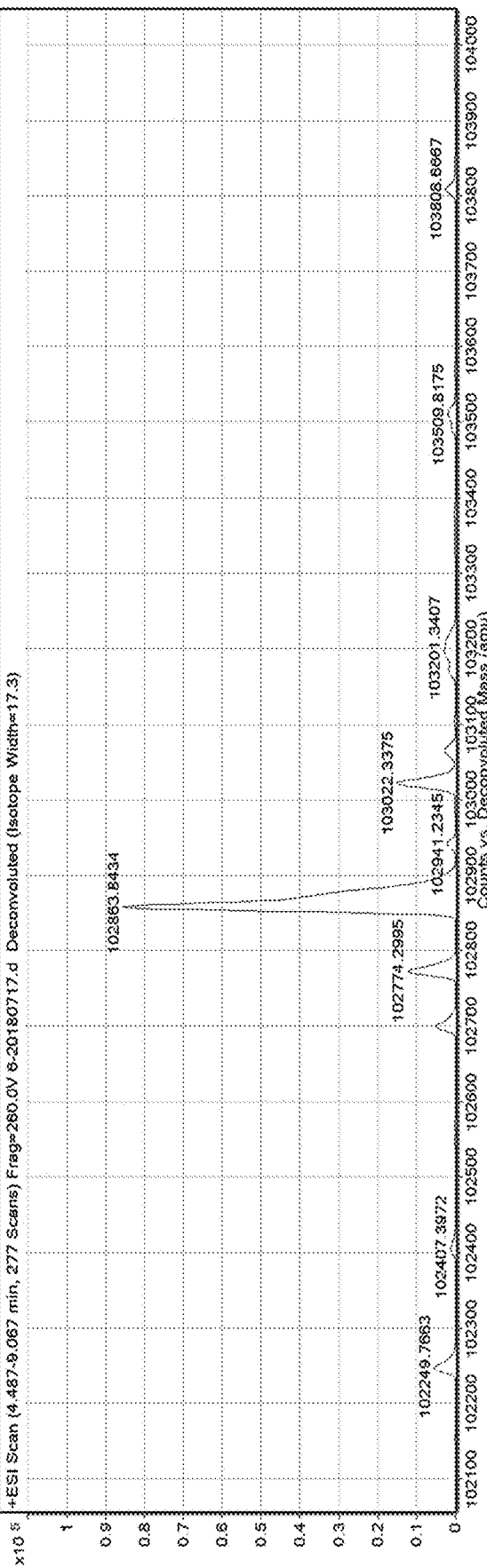
Figure 3E:
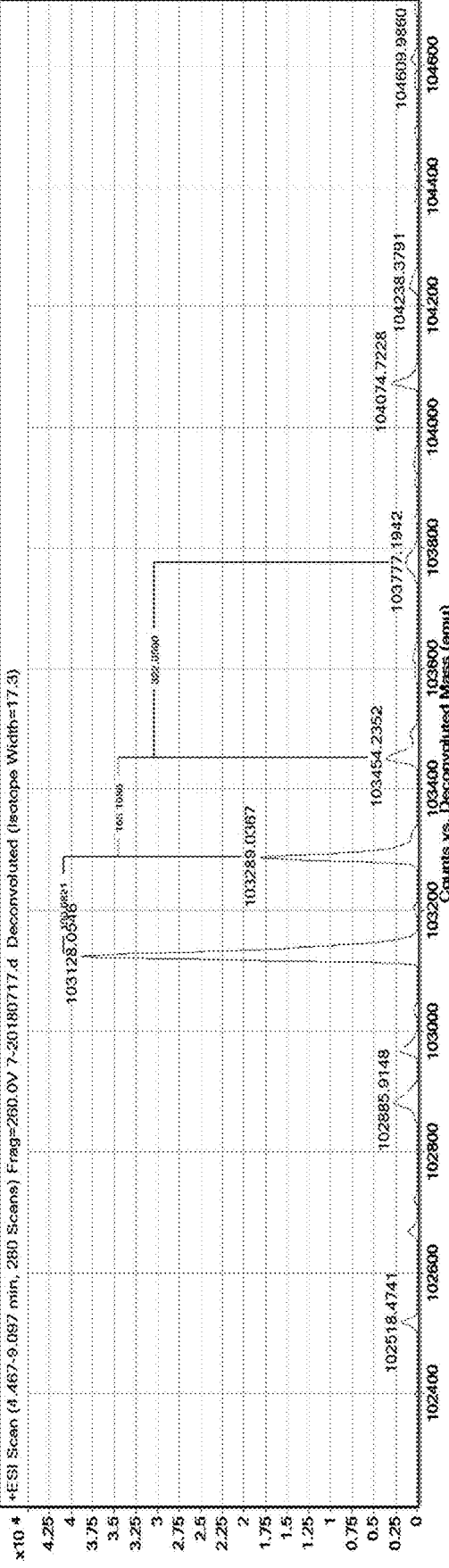
Figure 3F:
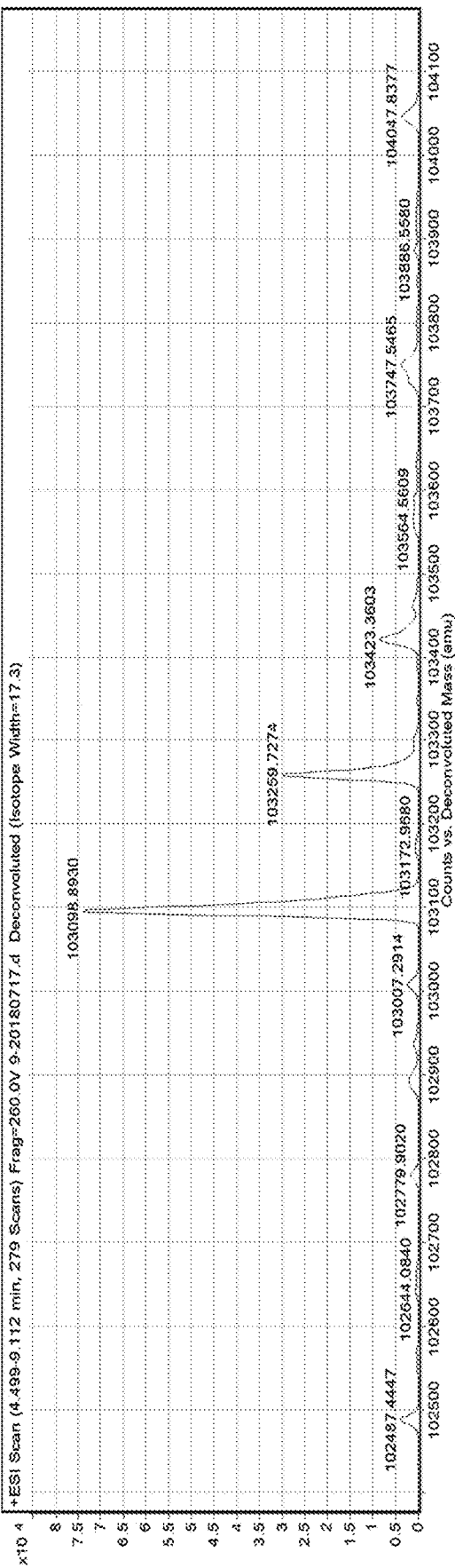
Figure 3G:
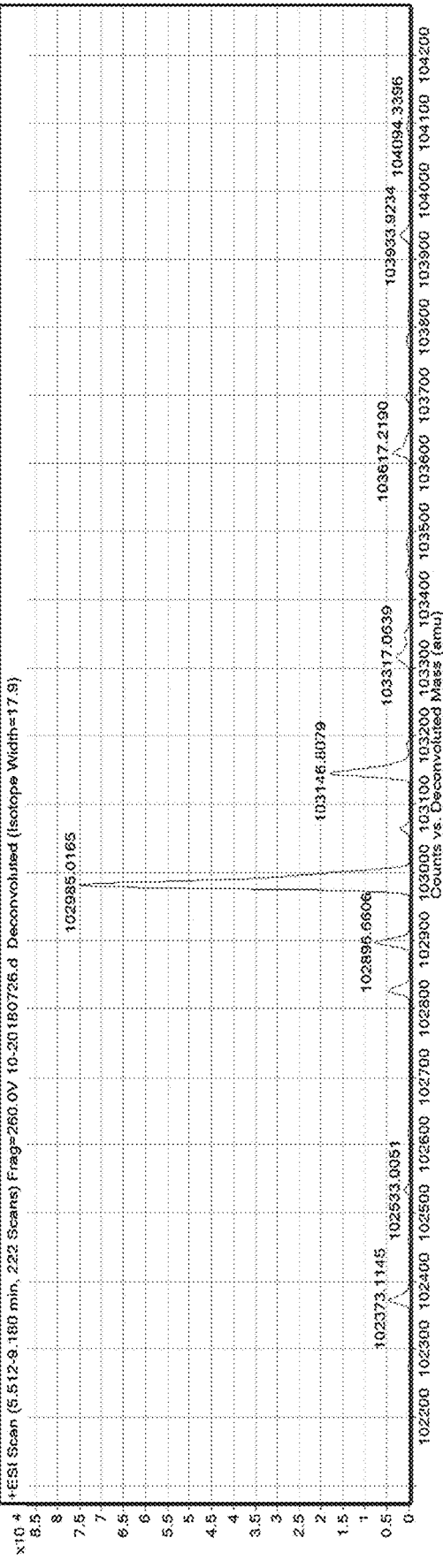
Figure 3H:
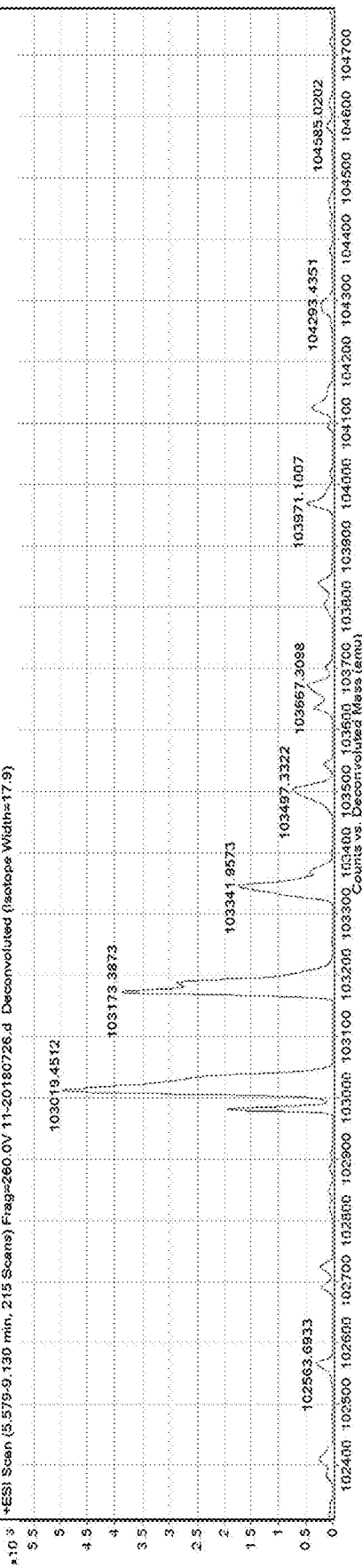
Figure 4A:
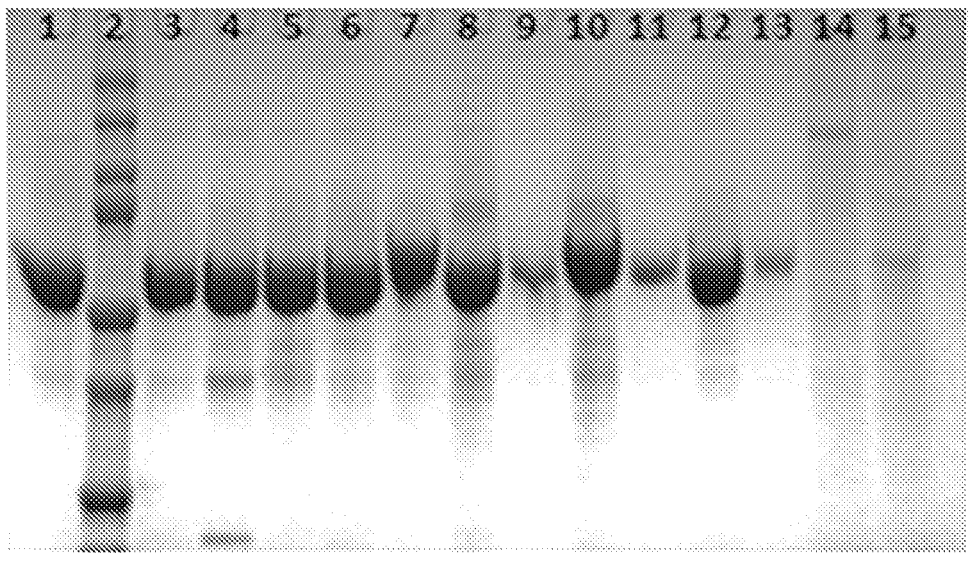
FIGS. 4A-4B show the results of SDS-PAGE electrophoresis detection of the fusion protein described herein.
Figure 4B:
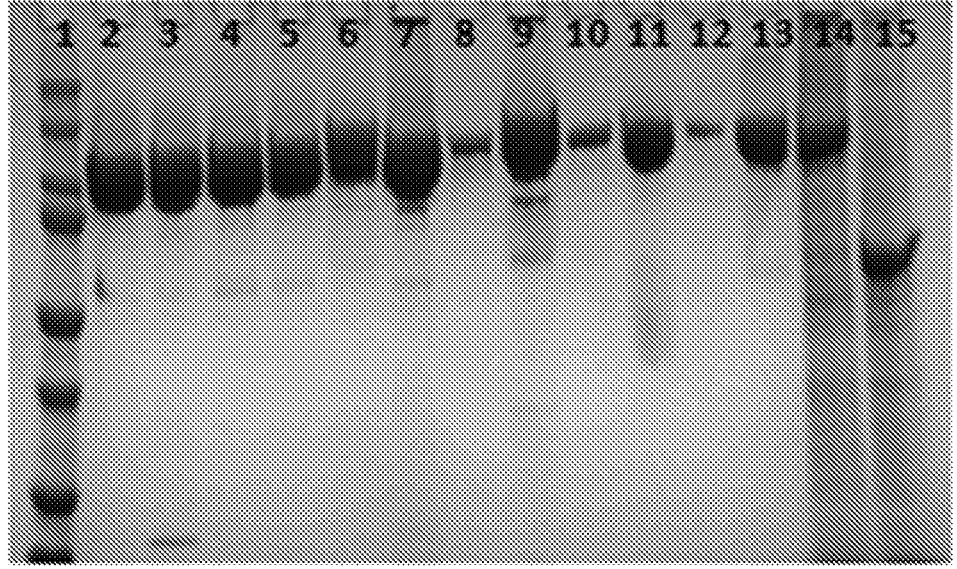

The cell culture solution was centrifuged at 200 g for 10 min. The supernatant was centrifuged at 8000 rpm for 30 min, and the supernatant was collected. The collected cell culture supernatant was subjected to affinity purification by Protein A chromatography (EzFast Protein A Diamond, Bestchrom). The equilibration solution was 20 mM PBS, 0.15 M NaCl, pH 7.4. The eluent was 0.1 M glycine buffer of pH 3.2. The protein eluate was collected at target absorption peak and dialyzed with 20 mM PBS buffer of pH 7.4 to take part of the sample for mass spectrometry. Molecular weight detected by mass spectrometry detection was consistent with theoretical molecular weight, and they were in homodimeric form. The mass spectrum results of some samples are shown in FIGS. 3A to 3H. At the same time, the collected samples were detected by 10% SDS-PAGE electrophoresis after reduction (seen in FIG. 4A) and non-reduction treatment (seen in FIG. 4B). The results are shown in FIGS. 4A, 4B, and Table 2. Wherein, the mass spectrometry results of dual target 1 # are shown in FIG. 3A. The mass spectroscopic results of dual target 2 # are shown in FIG. 3B. The mass spectrometry results of dual target 4 # and dual target 5 # are shown in FIG. 3C. The mass spectrometry results of dual target 6 # are shown in FIG. 3D. The mass spectrometry results of dual target 7 # are shown in FIG. 3E. The mass spectrometry results of dual target 9 # are shown in FIG. 3F. The mass spectrometry results of dual target 10 # are shown in FIG. 3G. The mass spectrum results of dual target 11 # are shown in FIG. 3H.

In FIG. 4A, the samples are: 1, control: dual target RAHL (its amino acid sequence is shown in SEQ ID No. 41); 2, Marker; 3, dual target 1 #; 4, dual target 2 #; 5, dual target 3 #; 6, dual target 4 #; 7, dual target 5 #; 8, dual target 6 #; 9, dual target 7 #; 10, dual target 8 #; 11, Dual target 9 #; 12, double target 10 #; 13, double target 11 #; 14, double target 11 #supernatant; 15, double target 11 #supernatant. The above samples each contained 20 mM DTT except for Sample 14.

In FIG. 4B, the samples are: 1, Marker; 2, dual target 1 #; 3, dual target 2 #; 4, dual target 3 #; 5, dual target 4 #; 6, dual target 5 #; 7, double target 6 #; 8, double target 7 #; 9, double target 8 #; 10, double target 9 #; 11, double target 10 #; 12, double target 11 #; 13, control, double target RAHL; 14, double-target 10 #supernatant; 15, double-target 10 #; wherein sample 15 contains 20 mM DTT, which is a sample treated with reduction.

Wherein, the dual target RAHL was prepared according to the following method:

Firstly, the upstream fragment (including part of GLP-1) and the downstream fragment (Fc-FGF21) were obtained by PCR amplification. The PCR amplification procedure was as follows: pre-denaturation at 98° C. for 5 min; denaturation at 98° C. for 10 s; annealing at 56° C. for 10 s; extending at 72° C. for 5 s or 10 s; repeating 30 cycles; and extending at 72° C. for 8 min. The PCR product was then detected by 1.0% agarose gel electrophoresis, and the upstream and downstream fragments were recovered by using an OMEGA gel recovery kit. The obtained upstream fragment and downstream fragment were subjected to SOE PCR to receive full-length sequence. The SOE PCR amplification procedure was as follows: pre-denaturation at 98° C. for 5 min; denaturation at 98° C. for 10 s; annealing at 56° C. for 10 s; extending at 72° C. for 15 s; repeating 30 cycles; and extending at 72° C. for 8 min. Then the full-length target gene was recovered by Gel Extraction Kit kit (OMEGA, America).

The full-length target gene sequence and the vector plasmid pcDNA3.4 were digested with the endonuclease HindIII and EcoRI (TAKARA, Japan) at 37° C., and the digested product was purified and recovered by using a Gel Extraction Kit according to the manufacturer's instructions. The purified objective gene was ligated with the vector using a DNA Ligation Kit Ver.2.1 (TAKARA, Japan) according to the manufacturer's instructions and incubated at 16° C. for 1 hour to obtain a recombinant expression plasmid.

The above recombinant expression plasmid was transformed into competent cells DH5a, and bacteria was coated into an ampicillin plate. The monoclonal on the plate was picked and cultured in 1 ml of LB medium (peptone 10 g/L, yeast extract 5 g/L, sodium chloride 10 g/L and agar 2%, the content of antibiotic 100 μg/mL) to extract the plasmid. After sequencing and validation, a series of validated correct expression vectors were extracted with Invitrogen Plasmid Kit and digested with restriction enzyme PvuI (TAKARA, Japan). After linearization, the product was purified and recovered by ethanol precipitation method and stored at −20° C. for future use.

The primers used in the experiment are as follows: the upstream fragment (including the GLP-1 part) amplification primers include: primer AUZ-F (SEQ ID No: 37), and primer lfc1-R (SEQ ID NO:38). The downstream fragment (Fc-FGF21) amplification primers include: primer lfc1-F (SEQ ID NO: 39), and primer fgf21-R (SEQ ID NO: 40). SOE PCR primers include: primer AUZ-F (SEQ ID NO: 37), primer fgf21-R (SEQ ID NO: 40).

HEK293F host cells (Invitrogen, Freestyle 293F) were resuscitated with 293 Expi Medium. The host cells were transfected when cell density was about $1 \times 10^6$ cells/mL. About $3 \times 10^7$ cells were transfected, and the linearized expression vector was about 30 μg. The cells were transfected with Expi Fectamine293 Reagent Transfection Kit.

After transfection, the cells were cultured in 30 mL of 293 Expression Medium. On the second day of culture, transformants were started to be screened with geneticinG418 (merck). The medium was replaced every 3 days depending on the growth of the cells. After about 14 days, resistant clones appeared and could be expanded. The cell passage density was about 0.5×10⁶ cells/mL. The obtained mixed clone was subcultured with 293 Expression Medium. When the cell viability was about 90%, the cell culture fluid was collected.

The cell culture solution prepared was centrifuged at 200 g for 10 min, and the supernatant was centrifuged at 8000 rpm for 30 min, and the supernatant was collected. The collected cell culture supernatant was subjected to affinity purification by Protein A chromatography (EzFast Protein A Diamond, Bestchrom). The equilibration solution was 20 mM PBS, 0.15 M NaCl, pH 7.4. The eluent was 0.1 M glycine of pH 3.2. The protein eluate was collected at target absorption peak and dialyzed with PBS buffer to take part of the sample for mass spectrometry. Molecular weight detected by mass spectrometry (Accurate-Mass Q-TOF LC/MS, Type G6530, Agilent Technologies) detection was consistent with theoretical molecular weight, and they were in homodimeric form. Results were as shown in table 3.

At the same time, the collected samples were detected by 10% SDS-PAGE electrophoresis.

TABLE 2

Analysis of mass spectrometry results of fusion proteins (7 days of fermentation)

| Mutant | Percentage of intact protein | Percentage of FGF21 degradation at the 180th position | Percentage of FGF21 degradation at the 181th position |
|---|---|---|---|
| Dual target 1 # | 93.99% | 1.75% | 1.49% |
| Dual target 2# | 93.78% | 2.01% | 1.16% |
| Dual target 3# | 94.54% | 1.85% | 0.94% |
| Dual target 4# | 99.99% | 0 | 0 |
| Dual target 5# | 55.6% | — | — |
| Dual target 6# | 83.62% | — | — |
| Dual target 7# | 94.74% | 1.14% | 0 |
| Dual target 8# | 60.56% | — | — |
| Dual target 9# | 95.44% | 0.00% | 0.93% |
| Dual target 10# | 92.05% | 4.03% | 2.00% |
| Dual target 11# | 94.18% | 0 | 2.20% |

The results show that the fusion proteins described in the present application can effectively avoid the problem of FGF21 degradation due to the FGF21 polypeptide containing a combination of amino acid mutations with specific sites. The complete protein percentage of the fusion proteins described herein are all above 83%, and most of them can reach above 92%.

Example 3 Preparation of Dual-Target Fusion Protein and Single-Target Fusion Protein 3.1 Construction of Expression Vector Plasmid-X2

Suzhou Hongxun Biotechnology Co., Ltd. was entrusted to synthesize the target gene of dual-target fusion protein, including dual-target RGHLQQ (its amino acid sequence is shown in SEQ ID NO: 43), dual-target RAHLQQ (its amino acid sequence is shown in SEQ ID NO: 44), single-target RGHLQQ (its amino acid sequence is shown in SEQ ID NO: 45), dual target RAHL (its sequence is shown in SEQ ID NO: 41). The sequence of the objective gene and the vector plasmid pXC17.4 were digested with the endonuclease HindIII and EcoRI (TAKARA, Japan) at 37° C., and the digested product was purified and recovered by using a Gel Extraction Kit according to the manufacturer's instructions. The purified objective gene was ligated with the vector using the DNA Ligation Kit Ver.2.1 (TAKARA, Japan) according to the manufacturer's instructions and incubated at 16° C. for 1 hour to obtain a recombinant expression plasmid.

The above recombinant expression plasmid was transformed into competent cells DH5a, and bacteria was coated into an ampicillin plate. The monoclonal on the plate was picked and cultured in 1 ml of LB medium (peptone 10 g/L, yeast extract 5 g/L, sodium chloride 10 g/L and agar 2%, the content of antibiotic 100 μg/mL) to extract the plasmid. After sequencing and validation by Guangzhou IGE Biotechnology Co., Ltd., a series of validated correct expression vectors were extracted with Invitrogen Plasmid Kit and digested with restriction enzyme PvuI (TAKARA, Japan). After linearization, the product was purified and recovered by ethanol precipitation method and stored at −20° C. for future use.

3.2 Transfection of the Vector and Expression in Cells

After CHO host cells were resuscitated with Cellvento CHO-200 medium (Merck), cells were collected for transfection when the cell density was approximately 4.76×10⁶ cells/mL. The transfected cells were about 1×10⁷ and plasmids were about 40 μg, which were transfected by electric shock (Bio-Rad, gene pulser Xcell). Cells were cultured in 20 mL Cellvento CHO-200 medium after electric shock. On the second day of culture, cells were collected by centrifugation and resuspended in 20 mL of Cellvento CHO-200 medium added with L-Methionine sulfoximine (Sigma-aldrich) to a final concentration of 50 μM. When the cell density was about 0.6×10⁶ cells/mL, the obtained mixed clones were passaged with Cellvento CHO-200 medium. The passaged cell density was about 0.2×10⁶ cells/mL. When the cell viability was about 90%, the cell culture fluid was collected.

3.3 Purification and Detection of Fusion Proteins

Figure 7A:
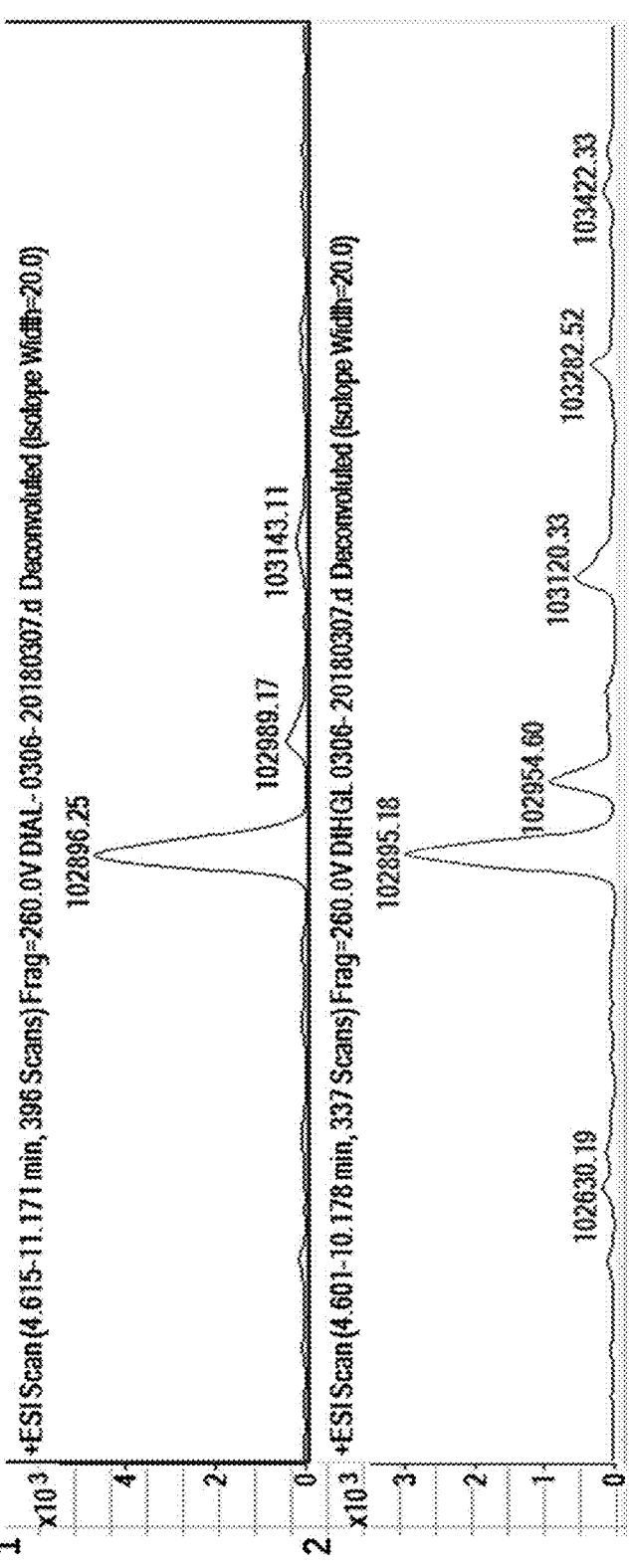
FIGS. 7A-7D show mass spectrometry detection diagrams of the fusion proteins described herein.
Figure 7B:
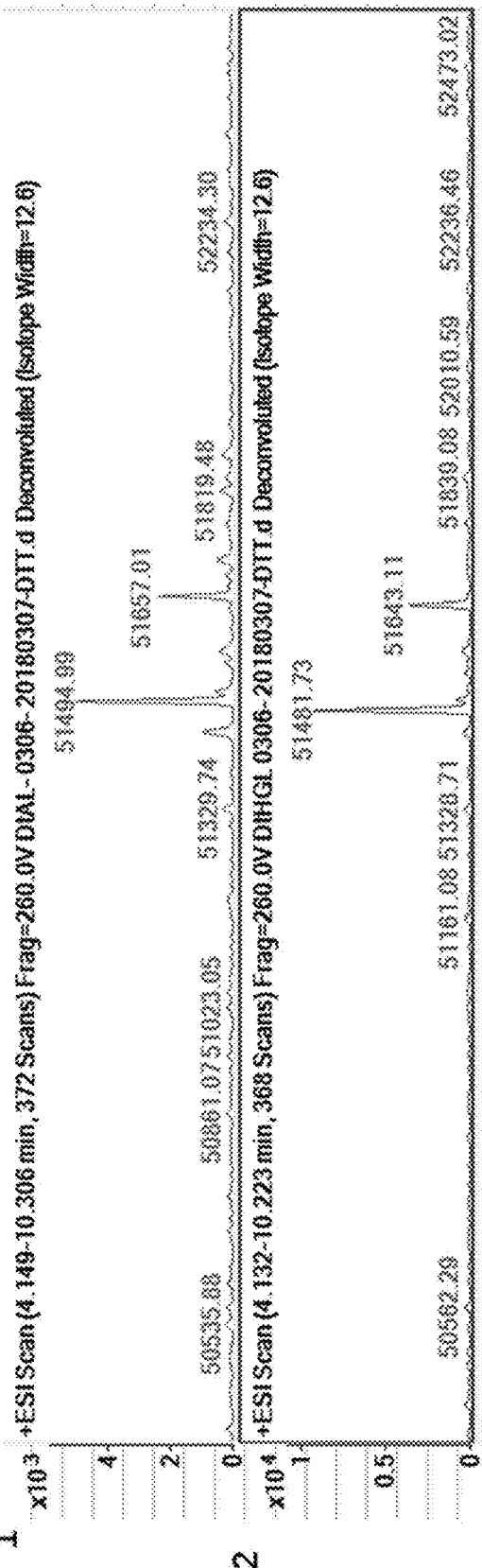
Figure 7C:
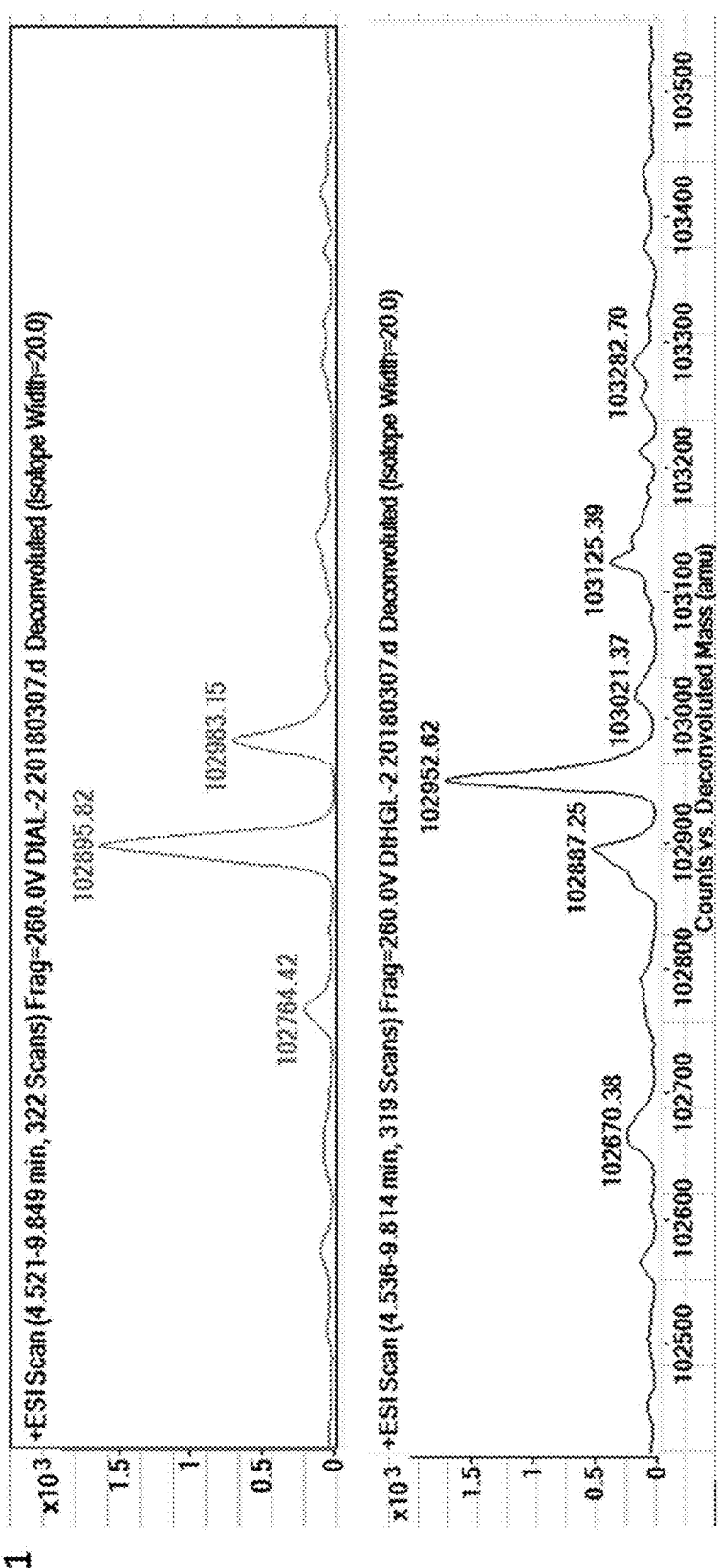
Figure 7D:
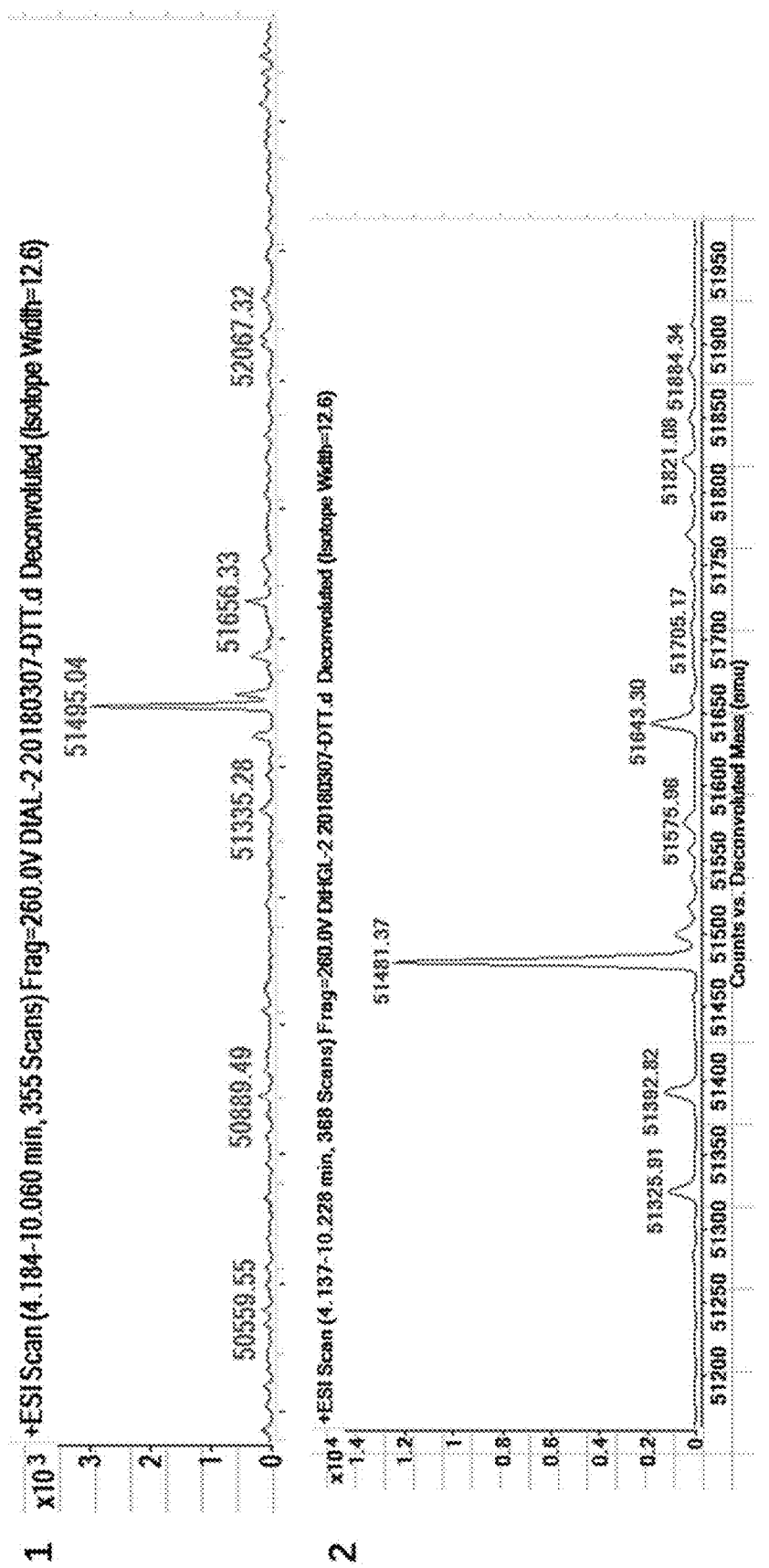

The cell culture solution prepared was centrifuged at 200 g for 10 min, and the supernatant was centrifuged at 8000 rpm for 30 min, and the supernatant was collected. The collected cell culture supernatant was subjected to affinity purification by Protein A chromatography (EzFast Protein A Diamond, Bestchrom). The equilibration solution was 20 mM PBS, 0.15 M NaCl, pH 7.4. The eluent was 0.1 M glycine of pH 3.2. The protein eluate was collected at target absorption peak and dialyzed with PBS buffer to take part of the sample for mass spectrometry. Molecular weight detected by mass spectrometry (Accurate-Mass Q-TOF LC/MS, Type G6530, Agilent Technologies) detection was consistent with theoretical molecular weight, and they were in homodimeric form. The results are shown in Table 3 and FIG. 7. Among them, FIG. 7A1 shows the detection results of non-reduction mass spectrometry after 4 days fermentation of dual target RAHLQQ; FIG. 7A2 shows the detection results of non-reduction mass spectrometry after 4 days fermentation of dual target RGHLQQ; FIG. 7B1 shows the detection results of reduction mass spectrometry after 4 days fermentation of dual target RAHLQQ; FIG. 7B2 shows the detection results of reduction mass spectrometry after 4 days fermentation of dual target RGHLQQ; FIG. 7C1 shows the detection results of non-reduction mass spectrometry after 7 days fermentation of dual target RAHLQQ; FIG. 7C2 shows the detection results of non reduction mass spectrometry after 7 days fermentation of dual target RGHLQQ; FIG. 7D1 shows the detection results of reduction mass spectrometry after 7 days fermentation of dual target RAHLQQ; FIG. 7D2 shows the detection results of reduction mass spectrometry after 7 days fermentation of dual target RGHLQQ.

TABLE 3

Analysis of mass spectrometry results of fusion proteins subjected to reduction treatment

| Mutant | Fermentation for 4 days Percentage of intact protein | Fermentation for 4 days Percentage of FGF21 degradation at the 19th position | Fermentation for 7 days Percentage of intact protein | Fermentation for 7 days Percentage of FGF21 degradation at the 19th position |
|---|---|---|---|---|
| Dual target RAHLQQ | 82.30% | 12% | 54.31% | 23.89% |
| Dual target RGHLQQ | 88.73% | 8.18% | 62.89% | 20.31% |

At the same time, the collected samples were detected by 10% SDS-PAGE electrophoresis. The results are shown in Table 4, FIGS. 5A and 5B.

Figure 5A:
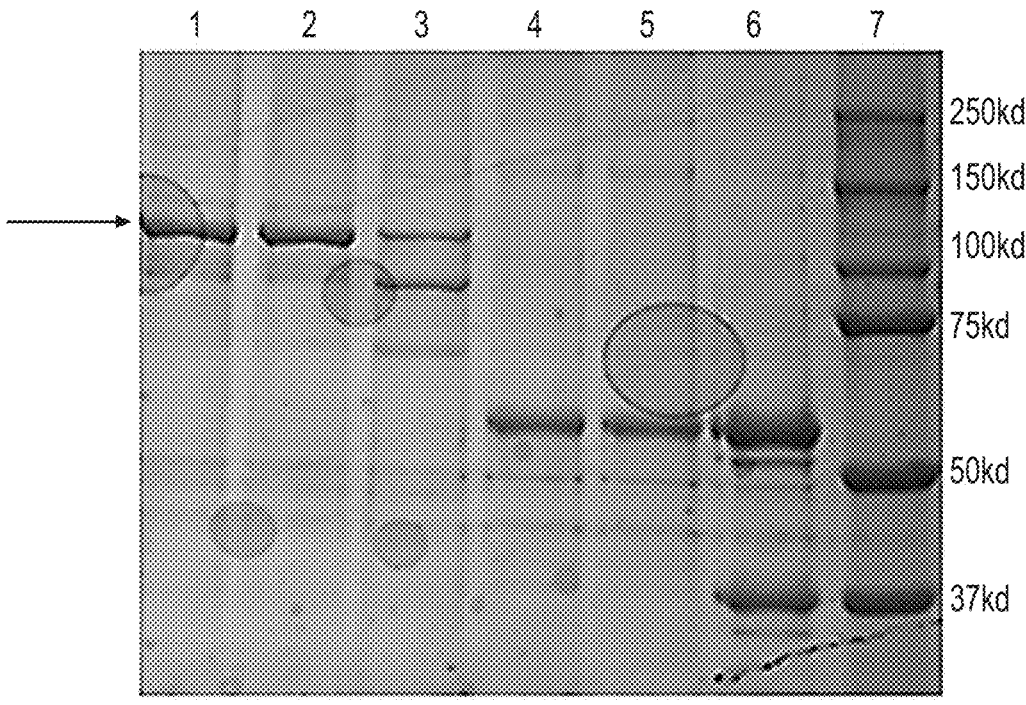
FIGS. 5A-5B show the results of SDS-PAGE electrophoresis detection of the fusion protein described herein.
Figure 5B:
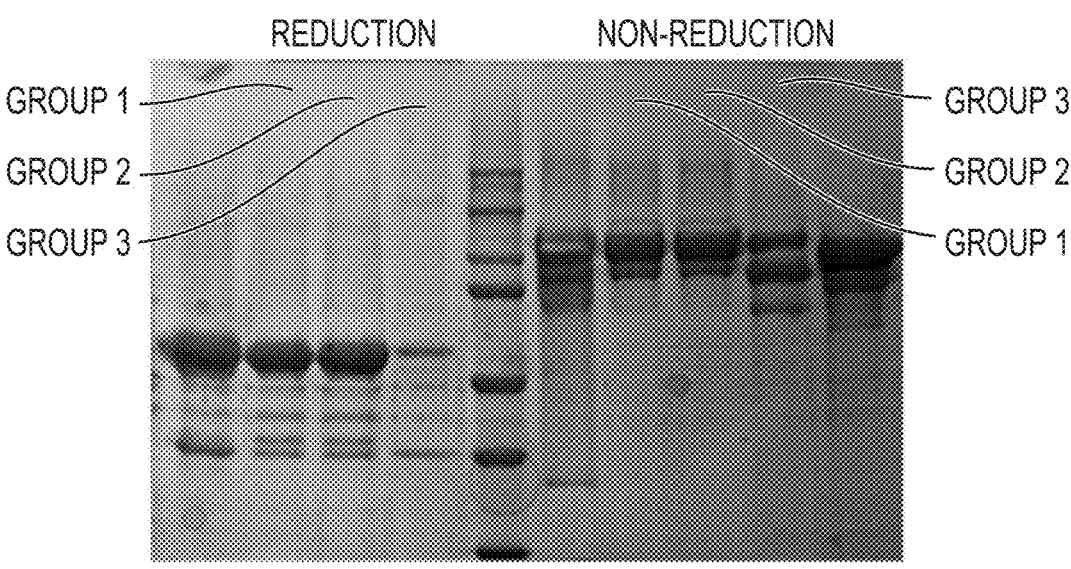

Among them, in FIG. 5A, 1: dual target RGHLQQ supernatant-non-reduction; 2: dual target RAHLQQ supernatant-non-reduction; 3: RAHL supernatant-non-reduction; 4: dual target RGHLQQ supernatant-reduction; 5: dual target RAHLQQ supernatant-reduction; 6: RAHL purified sample-reduction; 7: Marker. In FIG. 5B, reduction group 1: dual target RGHLQQ purified sample; reduction group 2: dual target RAHLQQ purified sample; reduction group 3: RAHL supernatant; non-reduction group 1: dual target RGHLQQ purified sample; non-reduction group 2: dual target RAHLQQ purified samples; non-reduced group 3: dual target RAHL purified samples.

TABLE 4

Analysis of SDS-PAGE results of fusion proteins

| Mutant | Fermentation for 4 days Percentage of purity |
|---|---|
| Dual target RAHLQQ | About 75% |
| Dual target RGHLQQ | About 75% |
| Dual target RAHL | About 40% |

The results of example 2 and example 3 show that the target bands of the dual-target fusion protein mutated at position 19 to Q account for about 75%, while the target bands of the double fusion protein mutated at position 19 to V account for more than 90%. This shows that mutation to V at position 19 of the FGF21 polypeptide is more effective than mutation to Q in preventing FGF21 and even the fusion protein containing FGF21 from degradation.

Example 4 Blood Glucose Test In Vivo in a Mouse Model

The 6-week-old SPF-grade db/db mice (purchased from Jiangsu GemPharmatech Co, Ltd) were selected as the model animals of obese typeII diabetic for detection. The mice were injected subcutaneously at the dose of 10 nmol/kg, and the first administration was conducted on day 0, and the second administration was conducted on day 6. The solvent PBS was taken as a control, and the dual target 1 #,

26 dual target 2 #, dual target 3 #, dual target 4 #, dual target 7 #, dual target 9 #prepared in example 2 and dual target RAHL prepared in example 3 were taken for detection. The test method was to take blood from the tail tip of the mouse every morning (before administration), and the Luokang Total Excellence blood glucose meter was used for detecting blood glucose. Animals were fasted overnight on the last day of the experiment, and blood was collected from the orbits of the mice the next morning to prepare serum. Roche's automatic biochemical analyzer was used to detect fasting blood glucose.

Figure 6:
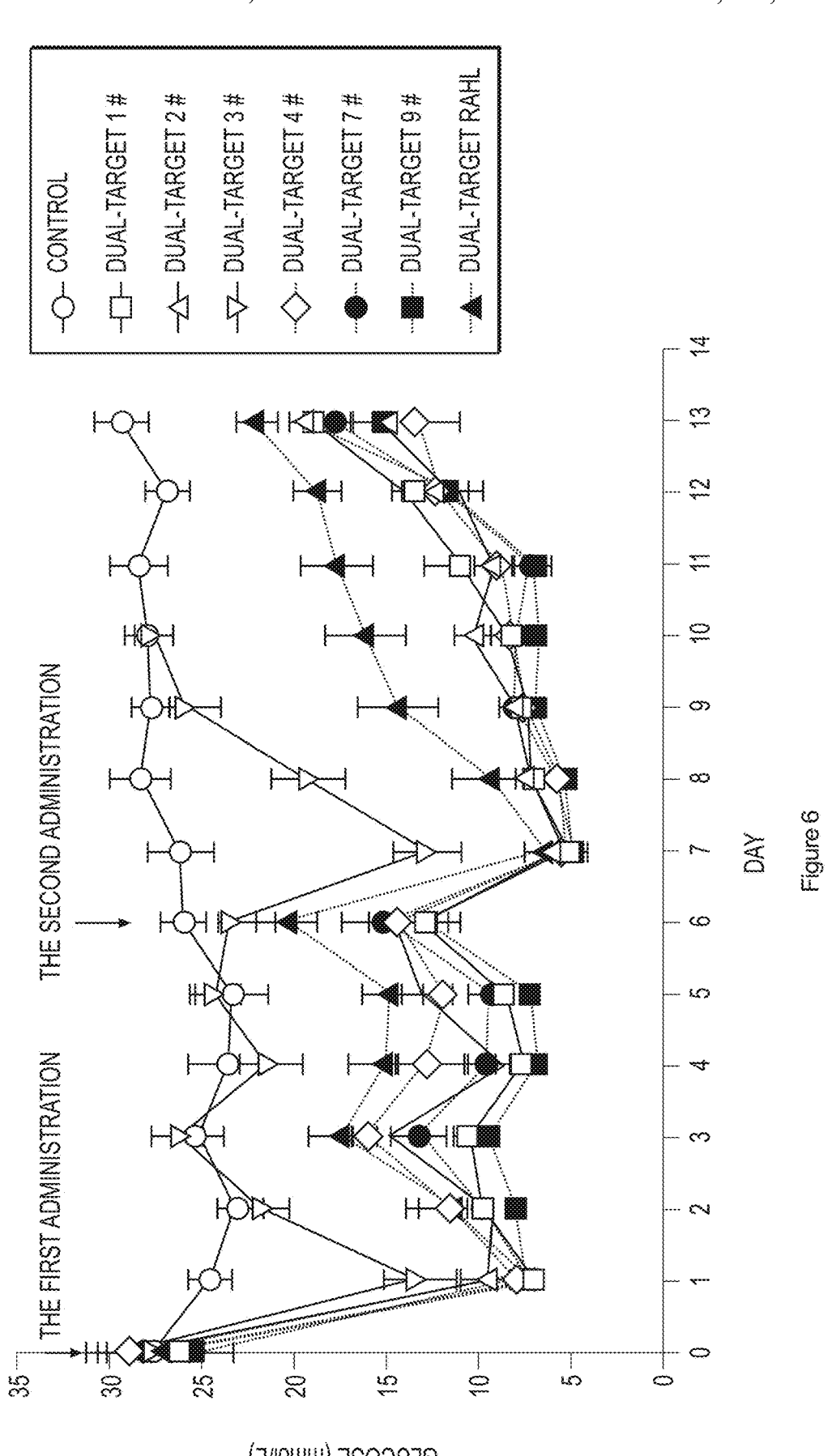
FIG. 6 shows the comparison results of the effects of the fusion protein described herein on the blood glucose of db/db mice.

FIG. 6 shows that the blood glucose in the vehicle control group was stable and at high blood glucose level (>23.0 mmol/L). Compared with the blank vehicle group, each sample can significantly reduce blood glucose. Among them, the dual-target 3 #protein is weak in reducing blood glucose, and can be maintained for only 24-48 hours in a single administration. Other samples can significantly lower blood glucose, and the glucose-lowering effects of the dual-target 9 #, dual-target 1 #, dual-target 2 #, dual-target 4 #, dual-target 7 #, dual-target 3 # are particularly significant.

The test results of fasting blood glucose show that dual-target 1 #, dual-target 4 # and the like can significantly reduce fasting blood glucose compared with the blank vehicle group. It can be seen that the fusion protein described herein can significantly reduce fasting blood glucose due to the FGF21 polypeptide containing a combination of amino acid mutations with specific sites described herein.

Example 5 Weight Detection of Mice

The mice in example 4 were taken for weight detection after administration. Administration was performed in the same manner as in Example 4, and daily weight changes were recorded. The results of the weight-time curve are shown in FIG. 8.

Figure 8:
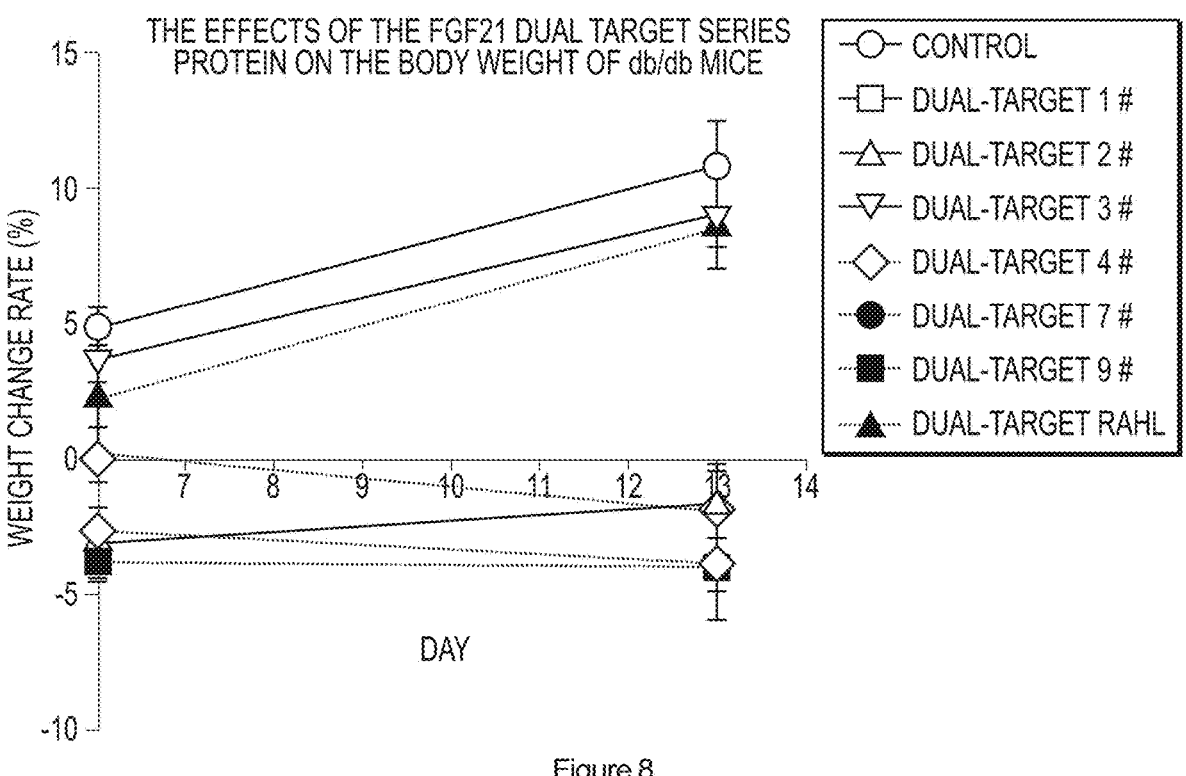
FIG. 8 shows the comparison results of the effects of the fusion protein described herein on the weight of db/db mice.

The results in FIG. 8 show that the dual-target 1 #, dual-target 2 #, dual-target 4 #, dual-target 7 #, and dual-target 9 #can continuously and significantly reduce body weight compared with the vehicle control group. Dual-target RAHL was able to reduce body weight only during the first week of administration (days 0 to 7). It can be seen that the fusion protein described herein can significantly reduce the weight of mice due to the FGF21 polypeptide containing a combination of amino acid mutations with specific sites described herein.

Example 6: A Study of the Hypoglycemic and Lipid-Improving Effects of Fusion Proteins Dual-Target RAHL, Dual-Target 1 # and Dual-Target 7 # in db/db Mouse Model The efficacy of fusion proteins in the db/db mouse model (Jiangsu GemPharmatech Co., Ltd.) was studied. The experimental process was as follows: the purified fusion proteins were diluted with 10 mM PBS, and db/db mice that meet the experimental requirements were randomly selected and divided into 4 groups: a control vehicle group (10 mM PBS dilution), a dual-target RAHL group, a dual-target 1 #group and a dual-target 7 #group. The dosage was calculated by injecting 10 nm/kg of fusion protein into each dB/db mouse. The dosage volume was 10 ml/kg. Each fusion protein was injected to eight mice which were administered once a week for two weeks.

Figure 9:
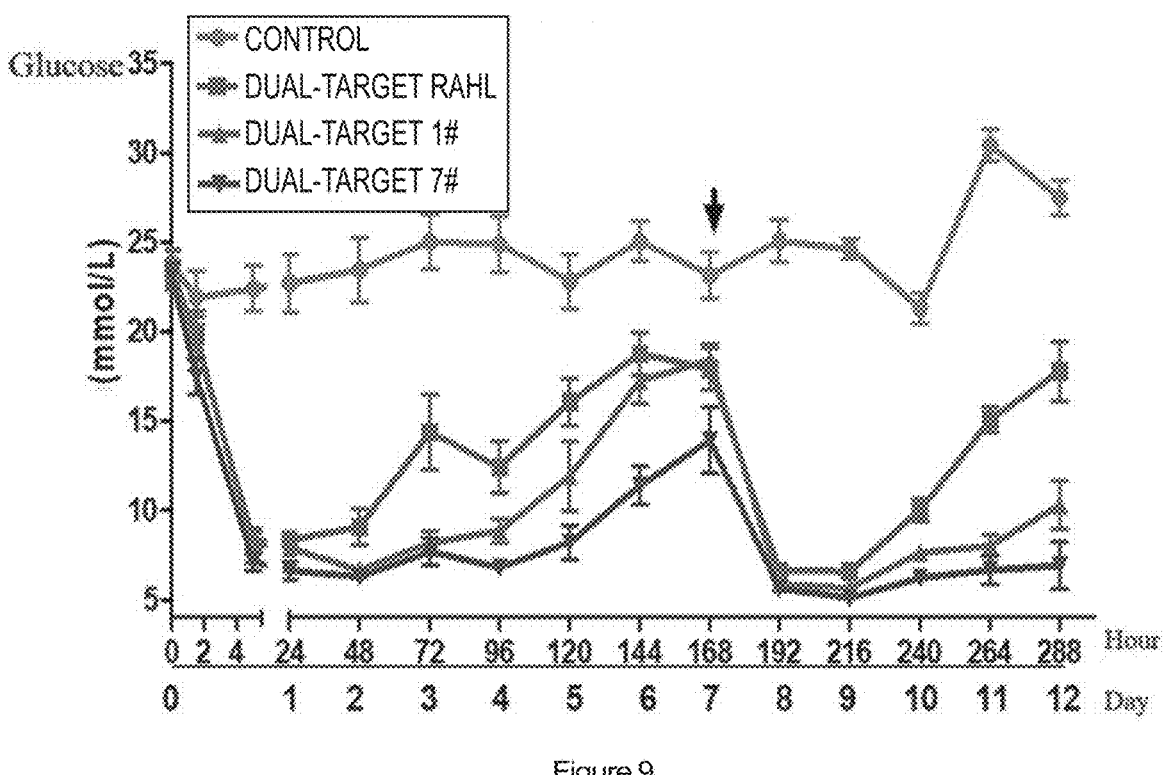
FIG. 9 shows the comparison results of the effects of the fusion protein described herein on the blood glucose of db/db mice.
Figure 10:
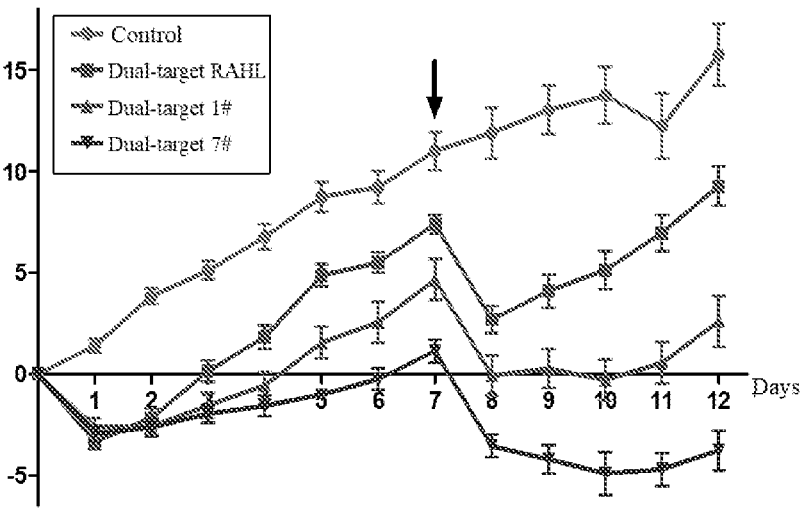
FIG. 10 shows the comparison results of the effect of the fusion protein described herein on the body weight growth rate of db/db mice.
Figure 11:
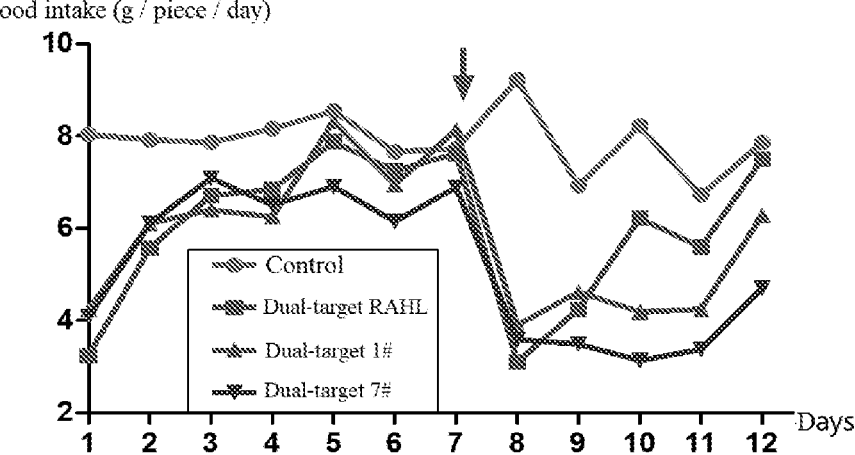
FIG. 11 shows the comparison results of the effect of the fusion protein described herein on the food intake of db/db mice.

The changes of blood glucose, body weight, and food intake were observed clinically after administration. The results are shown in FIGS. 9-11, wherein FIG. 9 shows the changes of blood glucose in mice after the injection of the fusion protein; FIG. 10 shows the changes of the growth rate of body weight in mice; FIG. 11 shows the changes of food intake in mice after injection of the fusion protein.

TABLE 5

| | Solvent group | Dual target RAHL group | Dual target 1 # group | Dual target 7# group |
|---|---|---|---|---|
| Effects of fusion protein on blood glucose, weight growth rate, and food intake in mice | | | | |
| Blood glucose on day 12 after the first injection (mmol/L) | 27.5 ± 3.0 | 17.8 ± 5.0*** | 10.3 ± 4.0*** | 6.9 ± 4.0*** |
| Body weight growth rate on day 12 after the first injection (%) | 15.8 ± 4.6 | 9.3 ± 2.9** | 2.6 ± 3.8*** | −3.8 ± 2.9*** |
| Food intake on day 12 after the first injection (g/piece) | 7.9 | 7.5 | 6.3 | 4.7 |

The results in FIGS. 9-11 and Table 5 show that compared with the vehicle control group, the dual-target RAHL, dual-target 1 #, and dual-target 7 #can significantly reduce blood glucose, body weight and food intake, wherein the therapeutic effects of the dual-target RAHL, dual-target 1 #, dual-target 7 # are more better.

Figure 12:
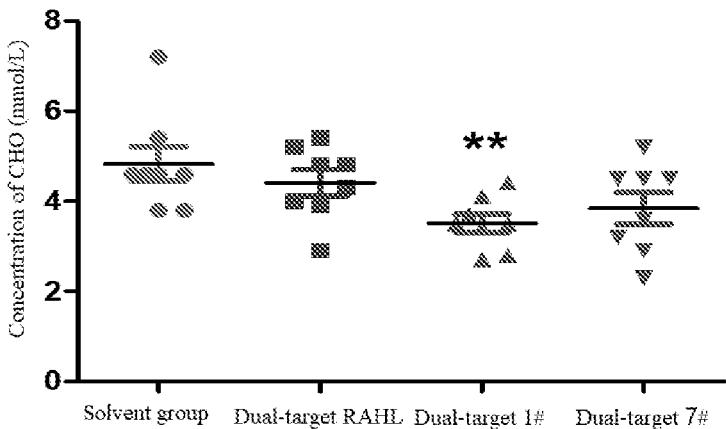
FIG. 12 shows the comparison results of the effects of the fusion protein described herein on total cholesterol of db/db mice.
Figure 13:
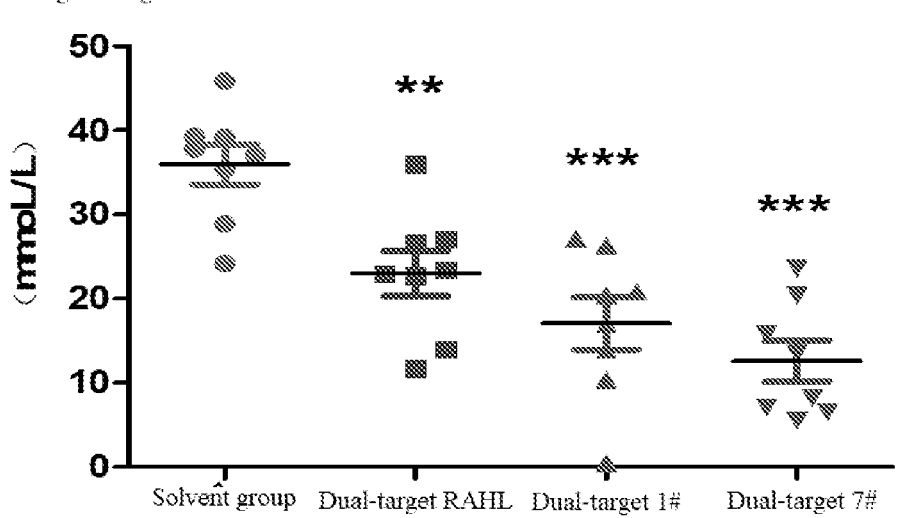
FIG. 13 shows the comparison results of the effects of the fusion protein described herein on the fasting blood-glucose of db/db mice.

After two weeks of administration, the mice were killed. Total blood cholesterol (CHO) level and fasting blood glucose were measured to evaluate the improvement of blood lipid and fasting blood glucose (results are shown in FIG. 12-13, wherein FIG. 12 shows the change of CHO level after the injection of the fusion protein; FIG. 13 shows the change of fasting blood glucose after the injection of the fusion protein).

TABLE 6

| | Solvent group | Dual target RAHL group | Dual target 1 # group | Dual target 7# group |
|---|---|---|---|---|
| Effects of fusion protein on CHO and fasting blood glucose in mice | | | | |
| Total cholesterol (CHO) level (mmol/L) | 4.8 ± 1.1 | 4.4 ± 0.8 | 3.5 ± 0.6** | 3.8 ± 1.0 |

TABLE 6-continued

| | Solvent group | Dual target RAHL group | Dual target 1 # group | Dual target 7# group |
|---|---|---|---|---|
| Effects of fusion protein on CHO and fasting blood glucose in mice | | | | |
| Fasting blood glucose (mmol/L) | 36.0 ± 6.7 | 23.0 ± 7.6 | 17.1 ± 8.8 | 12.6 ± 6.9 |

The results in FIGS. 12-13 and Table 6 show that dual target 1 #can significantly reduce total cholesterol levels (P<0.01), and dual target RAHL and dual target 7 #also show a decrease in blood lipid; double-target RAHL, dual-target 1 #, and dual-target 7 #can all reduce fasting blood glucose, as compared to the vehicle control group. Among them, the effect of double-target 1 # and 7 # are more excellent in reducing fasting blood glucose. It can be seen that the fusion protein described herein can significantly reduce glucose and improve blood lipid due to the FGF21 polypeptide containing a combination of amino acid mutations with specific sites described herein.

The foregoing detailed description is provided by way of explanation and illustration, and is not intended to limit the scope of the appended claims. Various changes in the implementation methods enumerated in the present application are obvious to those skilled in the art and are also within the scope of the appended claims and their equivalent schemes.

The invention claimed is:

1. An FGF21 polypeptide comprising the amino acid sequence of SEQ ID NO: 2, 3, 5, 7, or 8.

2. A fusion protein or immunoconjugate, which comprises the FGF21 polypeptide of claim 1.

3. The fusion protein or immunoconjugate of claim 2, which further comprises an immunoglobulin Fc domain, wherein the immunoglobulin Fc domain is an Fc of human IgG or a functional variant thereof.

4. The fusion protein or immunoconjugate of claim 3, wherein the immunoglobulin Fc domain comprises the amino acid sequence shown in SEQ ID NO: 12 or SEQ ID NO: 13.

5. The fusion protein or immunoconjugate of claim 2, wherein the fusion protein further comprises a linker, and the linker is a peptide linker, which comprises the amino acid sequence shown in SEQ ID NO: 16.

6. The fusion protein or immunoconjugate of claim 5, wherein the N-terminus of the linker is connected to the C-terminus of the immunoglobulin Fc domain, and the C-terminus of the linker is connected to the N-terminus of the FGF21 polypeptide.

7. The fusion protein or immunoconjugate of claim 2, wherein the fusion protein or immunoconjugate comprises the amino acid sequence shown in any one of SEQ ID NOs: 17, 18, 20, 22, or 23.

8. The fusion protein or immunoconjugate of claim 2, which further comprises GLP-1 or a functional variant thereof.

9. The fusion protein or immunoconjugate of claim 8, wherein the GLP-1 or the functional variant thereof comprises the amino acid sequence shown in SEQ ID NO: 14 or SEQ ID NO: 15.

10. The fusion protein or immunoconjugate of claim 8, which further comprises an immunoglobulin Fc domain, wherein the immunoglobulin Fc domain comprises the amino acid sequence shown in SEQ ID NO: 12 or SEQ ID NO: 13.

11. The fusion protein or immunoconjugate of claim 8, which further comprises a linker, wherein the linker is a peptide linker.

12. The fusion protein or immunoconjugate of claim 10, which further comprises a linker, wherein the linker is a peptide linker and comprises a first linker, the N-terminus of the first linker is connected to the C-terminus of the immunoglobulin Fc domain, and the C-terminus of the first linker is connected to the N-terminus of the FGF21 polypeptide;

and the linker also comprises a second linker, the N-terminus of the second linker is connected to the C-terminus of the GLP-1 or a variant thereof, and the C-terminus of the second linker is connected to the N-terminus of the immunoglobulin Fc domain;

each of the first linker and the second linker independently comprises an amino acid sequence shown in SEQ ID NO: 16.

13. The fusion protein or immunoconjugate of claim 8, which comprises the amino acid sequence shown in any one of SEQ ID NOs: 27, 28, 30, 32, or 33.

14. A method of treating diseases caused by FGF21 metabolic disorders comprising administrating a therapeutically effective amount of the FGF21 polypeptide of claim 1, a fusion protein comprising the FGF21 polypeptide, or an immunoconjugate comprising the FGF21 polypeptide to the patient.

* * * * *

SEQUENCE LISTING

```
<160> NUMBER OF SEQ ID NOS: 48

<210> SEQ ID NO 1
<211> LENGTH: 181
<212> TYPE: PRT
<213> ORGANISM: Homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60
```

```
Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 2
<211> LENGTH: 181
<212> TYPE: PRT
<213> ORGANISM: Artificial Sequence
<220> FEATURE:
<223> OTHER INFORMATION: FGF21-1

<400> SEQUENCE: 2

```
His Pro Ile Pro Asp Ser Ser Pro Leu Leu Gln Phe Gly Gly Gln Val
1                   5                   10                  15

Arg Gln Val Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Leu Ser
                165                 170                 175

Pro Ser Tyr Ala Ser
            180
```

<210> SEQ ID NO 3
<211> LENGTH: 181
<212> TYPE: PRT
<213> ORGANISM: Artificial Sequence
<220> FEATURE:
<223> OTHER INFORMATION: FGF21-2

<400> SEQUENCE: 3

-continued

```
His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Gly Ser Gln Gly Leu Ser
                165                 170                 175

Pro Ser Tyr Ala Ser
                180
```

<210> SEQ ID NO 4
<211> LENGTH: 181
<212> TYPE: PRT
<213> ORGANISM: Artificial Sequence
<220> FEATURE:
<223> OTHER INFORMATION: FGF21-3

<400> SEQUENCE: 4

```
His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Val Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Gly Ser Gln Gly Leu Ser
                165                 170                 175
```

```
Pro Ser Tyr Ala Ser
            180

<210> SEQ ID NO 5
<211> LENGTH: 181
<212> TYPE: PRT
<213> ORGANISM: Artificial Sequence
<220> FEATURE:
<223> OTHER INFORMATION: FGF21-4

<400> SEQUENCE: 5

His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Gly Ser Gln Gly Leu Ser
                165                 170                 175

Pro Ser Tyr Glu Ser
            180

<210> SEQ ID NO 6
<211> LENGTH: 181
<212> TYPE: PRT
<213> ORGANISM: Artificial Sequence
<220> FEATURE:
<223> OTHER INFORMATION: FGF21-6

<400> SEQUENCE: 6

His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
```

-continued

```
                  100                 105                 110

Gly Leu Pro Leu His Leu Pro Gly Asn Lys Ser Pro His Arg Asp Pro
            115                 120                 125

Ala Pro Arg Gly Pro Ala Val Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Leu Ser
                165                 170                 175

Pro Ser Tyr Ala Ser
            180

<210> SEQ ID NO 7
<211> LENGTH: 181
<212> TYPE: PRT
<213> ORGANISM: Artificial Sequence
<220> FEATURE:
<223> OTHER INFORMATION: FGF21-7

<400> SEQUENCE: 7

His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Leu Ser
                165                 170                 175

Pro Ser Tyr Ala Ser
            180

<210> SEQ ID NO 8
<211> LENGTH: 181
<212> TYPE: PRT
<213> ORGANISM: Artificial Sequence
<220> FEATURE:
<223> OTHER INFORMATION: FGF21-9

<400> SEQUENCE: 8

His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Cys His
            20                  25                  30
```

-continued

```
Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Gly Ser Gln Gly Leu Ser
                165                 170                 175

Pro Ser Tyr Ala Ser
            180

<210> SEQ ID NO 9
<211> LENGTH: 181
<212> TYPE: PRT
<213> ORGANISM: Artificial Sequence
<220> FEATURE:
<223> OTHER INFORMATION: FGF21-10

<400> SEQUENCE: 9

His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Val Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Gly Ser Gln Gly Leu Ser
                165                 170                 175

Pro Ser Tyr Ala Ser
            180

<210> SEQ ID NO 10
<211> LENGTH: 181
```

```
<212> TYPE: PRT
<213> ORGANISM: Artificial Sequence
<220> FEATURE:
<223> OTHER INFORMATION: FGF21-11

<400> SEQUENCE: 10

His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Cys His
                20                  25                  30

Leu Glu Ile Arg Glu Asp Gly Thr Val Gly Cys Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Val Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Leu Ser
                165                 170                 175

Pro Ser Tyr Ala Ser
                180

<210> SEQ ID NO 11
<211> LENGTH: 181
<212> TYPE: PRT
<213> ORGANISM: Artificial Sequence
<220> FEATURE:
<223> OTHER INFORMATION: FGF21-12

<400> SEQUENCE: 11

His Pro Ile Pro Asp Ser Ser Pro Leu Leu Gln Phe Gly Gly Gln Val
1               5                   10                  15

Arg Gln Val Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Arg Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140
```

```
Ala Leu Pro Glu Pro Pro Gly Ile Leu Ala Pro Gln Pro Pro Asp Val
145                 150                 155                 160

Gly Ser Ser Asp Pro Leu His Met Val Gly Ala Ser Gln Gly Leu Ser
                165                 170                 175

Pro Ser Tyr Glu Ser
            180
```

```
<210> SEQ ID NO 12
<211> LENGTH: 229
<212> TYPE: PRT
<213> ORGANISM: Homo sapiens

<400> SEQUENCE: 12

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Lys
225
```

```
<210> SEQ ID NO 13
<211> LENGTH: 228
<212> TYPE: PRT
<213> ORGANISM: Artificial Sequence
<220> FEATURE:
<223> OTHER INFORMATION: IgG-Fc-PAAK

<400> SEQUENCE: 13

Glu Ser Lys Tyr Gly Pro Pro Cys Pro Cys Pro Ala Pro Glu Ala
1               5                   10                  15

Ala Gly Gly Pro Ser Val Phe Leu Phe Pro Pro Lys Pro Lys Asp Thr
                20                  25                  30
```

-continued

```
Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
                180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
        210                 215                 220

Leu Ser Leu Gly
225
```

```
<210> SEQ ID NO 14
<211> LENGTH: 31
<212> TYPE: PRT
<213> ORGANISM: Homo sapiens

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30
```

```
<210> SEQ ID NO 15
<211> LENGTH: 31
<212> TYPE: PRT
<213> ORGANISM: Artificial Sequence
<220> FEATURE:
<223> OTHER INFORMATION: GLP-1-GEG

<400> SEQUENCE: 15

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
                20                  25                  30
```

```
<210> SEQ ID NO 16
<211> LENGTH: 15
<212> TYPE: PRT
<213> ORGANISM: Artificial Sequence
<220> FEATURE:
<223> OTHER INFORMATION: Linker

<400> SEQUENCE: 16
```

-continued

```
Gly Gly Gly Gly Ser Gly Gly Gly Gly Ser Gly Gly Gly Gly Ser
1               5                   10                  15

<210> SEQ ID NO 17
<211> LENGTH: 424
<212> TYPE: PRT
<213> ORGANISM: Artificial Sequence
<220> FEATURE:
<223> OTHER INFORMATION: Single target 1 #

<400> SEQUENCE: 17

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
                180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
                260                 265                 270

Glu Ala His Leu Glu Ile Arg Glu Asp Gly Thr Val Gly Gly Ala Ala
            275                 280                 285

Asp Gln Ser Pro Glu Ser Leu Leu Gln Leu Lys Ala Leu Lys Pro Gly
        290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
                340                 345                 350
```

-continued

```
Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
        370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly Leu Ser Pro Ser Tyr Ala Ser
                420
```

<210> SEQ ID NO 18
<211> LENGTH: 424
<212> TYPE: PRT
<213> ORGANISM: Artificial Sequence
<220> FEATURE:
<223> OTHER INFORMATION: Single target 2 #

<400> SEQUENCE: 18

```
Glu Ser Lys Tyr Gly Pro Pro Cys Pro Pro Cys Pro Ala Pro Glu Ala
1                 5                 10                 15

Ala Gly Gly Pro Ser Val Phe Leu Phe Pro Pro Lys Pro Lys Asp Thr
                20                 25                 30

Leu Met Ile Ser Arg Thr Pro Glu Val Thr Cys Val Val Val Asp Val
        35                 40                 45

Ser Gln Glu Asp Pro Glu Val Gln Phe Asn Trp Tyr Val Asp Gly Val
        50                 55                 60

Glu Val His Asn Ala Lys Thr Lys Pro Arg Glu Glu Gln Phe Asn Ser
65                 70                 75                 80

Thr Tyr Arg Val Val Ser Val Leu Thr Val Leu His Gln Asp Trp Leu
                85                 90                 95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
        210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
                260                 265                 270

Glu Ala His Leu Glu Ile Arg Glu Asp Gly Thr Val Gly Gly Ala Ala
        275                 280                 285
```

```
Asp Gln Ser Pro Glu Ser Leu Leu Gln Leu Lys Ala Leu Lys Pro Gly
    290             295             300

Val Ile Gln Ile Leu Gly Val Lys Thr Ser Arg Phe Leu Cys Gln Arg
305             310             315             320

Pro Asp Gly Ala Leu Tyr Gly Ser Leu His Phe Asp Pro Glu Ala Cys
            325             330             335

Ser Phe Arg Glu Arg Leu Leu Glu Asp Gly Tyr Asn Val Tyr Gln Ser
            340             345             350

Glu Ala His Gly Leu Pro Leu His Leu Pro Gly Asn Lys Ser Pro His
            355             360             365

Arg Asp Pro Ala Pro Arg Gly Pro Ala Arg Phe Leu Pro Leu Pro Gly
    370             375             380

Leu Pro Pro Ala Leu Pro Glu Pro Pro Gly Ile Leu Ala Pro Gln Pro
385             390             395             400

Pro Asp Val Gly Ser Ser Asp Pro Leu His Met Val Gly Gly Ser Gln
            405             410             415

Gly Leu Ser Pro Ser Tyr Ala Ser
            420
```

```
<210> SEQ ID NO 19
<211> LENGTH: 424
<212> TYPE: PRT
<213> ORGANISM: Artificial Sequence
<220> FEATURE:
<223> OTHER INFORMATION: Single target 3 #

<400> SEQUENCE: 19

Glu Ser Lys Tyr Gly Pro Pro Cys Pro Pro Cys Pro Ala Pro Glu Ala
1               5               10              15

Ala Gly Gly Pro Ser Val Phe Leu Phe Pro Pro Lys Pro Lys Asp Thr
            20              25              30

Leu Met Ile Ser Arg Thr Pro Glu Val Thr Cys Val Val Val Asp Val
            35              40              45

Ser Gln Glu Asp Pro Glu Val Gln Phe Asn Trp Tyr Val Asp Gly Val
    50              55              60

Glu Val His Asn Ala Lys Thr Lys Pro Arg Glu Glu Gln Phe Asn Ser
65              70              75              80

Thr Tyr Arg Val Val Ser Val Leu Thr Val Leu His Gln Asp Trp Leu
            85              90              95

Asn Gly Lys Glu Tyr Lys Cys Lys Val Ser Asn Lys Gly Leu Pro Ser
            100             105             110

Ser Ile Glu Lys Thr Ile Ser Lys Ala Lys Gly Gln Pro Arg Glu Pro
            115             120             125

Gln Val Tyr Thr Leu Pro Pro Ser Gln Glu Glu Met Thr Lys Asn Gln
    130             135             140

Val Ser Leu Thr Cys Leu Val Lys Gly Phe Tyr Pro Ser Asp Ile Ala
145             150             155             160

Val Glu Trp Glu Ser Asn Gly Gln Pro Glu Asn Asn Tyr Lys Thr Thr
            165             170             175

Pro Pro Val Leu Asp Ser Asp Gly Ser Phe Phe Leu Tyr Ser Lys Leu
            180             185             190

Thr Val Asp Lys Ser Arg Trp Gln Glu Gly Asn Val Phe Ser Cys Ser
            195             200             205

Val Met His Glu Ala Leu His Asn His Tyr Thr Gln Lys Ser Leu Ser
    210             215             220
```

-continued

```
Leu Ser Leu Gly Gly Gly Gly Gly Ser Gly Gly Gly Gly Ser Gly Gly
225             230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
            325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Val Phe Leu Pro Leu Pro Gly
    370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Gly Ser Gln
            405                 410                 415

Gly Leu Ser Pro Ser Tyr Ala Ser
            420
```

```
<210> SEQ ID NO 20
<211> LENGTH: 424
<212> TYPE: PRT
<213> ORGANISM: Artificial Sequence
<220> FEATURE:
<223> OTHER INFORMATION: Single target 4 #

<400> SEQUENCE: 20
```

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160
```

-continued

```
Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
                260                 265                 270

Glu Ala His Leu Glu Ile Arg Glu Asp Gly Thr Val Gly Gly Ala Ala
            275                 280                 285

Asp Gln Ser Pro Glu Ser Leu Leu Gln Leu Lys Ala Leu Lys Pro Gly
            290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
                340                 345                 350

Glu Ala His Gly Leu Pro Leu His Leu Pro Gly Asn Lys Ser Pro His
            355                 360                 365

Arg Asp Pro Ala Pro Arg Gly Pro Ala Arg Phe Leu Pro Leu Pro Gly
            370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Gly Ser Gln
                405                 410                 415

Gly Leu Ser Pro Ser Tyr Glu Ser
            420
```

<210> SEQ ID NO 21
<211> LENGTH: 424
<212> TYPE: PRT
<213> ORGANISM: Artificial Sequence
<220> FEATURE:
<223> OTHER INFORMATION: Single target 6 #

<400> SEQUENCE: 21

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
            50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95
```

-continued

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Gly Gly Gly Ser Gly Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
            260                 265                 270

Glu Ala His Leu Glu Ile Arg Glu Asp Gly Thr Val Gly Gly Ala Ala
            275                 280                 285

Asp Gln Ser Pro Glu Ser Leu Leu Gln Leu Lys Ala Leu Lys Pro Gly
            290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
            355                 360                 365

Arg Asp Pro Ala Pro Arg Gly Pro Ala Val Phe Leu Pro Leu Pro Gly
            370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly Leu Ser Pro Ser Tyr Ala Ser
            420
```

```
<210> SEQ ID NO 22
<211> LENGTH: 424
<212> TYPE: PRT
<213> ORGANISM: Artificial Sequence
<220> FEATURE:
<223> OTHER INFORMATION: Single target 7 #

<400> SEQUENCE: 22

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30
```

-continued

```
Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
            245                 250                 255

Gly Gln Val Arg Gln Val Tyr Leu Tyr Thr Asp Asp Ala Gln Gln Thr
            260                 265                 270

Glu Cys His Leu Glu Ile Arg Glu Asp Gly Thr Val Gly Cys Ala Ala
            275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
            355                 360                 365

Arg Asp Pro Ala Pro Arg Gly Pro Ala Arg Phe Leu Pro Leu Pro Gly
    370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly Leu Ser Pro Ser Tyr Ala Ser
            420
```

<210> SEQ ID NO 23
<211> LENGTH: 424
<212> TYPE: PRT

<213> ORGANISM: Artificial Sequence
<220> FEATURE:
<223> OTHER INFORMATION: Single target 9 #

<400> SEQUENCE: 23

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
            260                 265                 270

Glu Cys His Leu Glu Ile Arg Glu Asp Gly Thr Val Gly Cys Ala Ala
        275                 280                 285

Asp Gln Ser Pro Glu Ser Leu Leu Gln Leu Lys Ala Leu Lys Pro Gly
        290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
            355                 360                 365

Arg Asp Pro Ala Pro Arg Gly Pro Ala Arg Phe Leu Pro Leu Pro Gly
        370                 375                 380

Leu Pro Pro Ala Leu Pro Glu Pro Pro Gly Ile Leu Ala Pro Gln Pro
```

-continued

```
385                 390                 395                 400

Pro Asp Val Gly Ser Ser Asp Pro Leu His Met Val Gly Gly Ser Gln
                405                 410                 415

Gly Leu Ser Pro Ser Tyr Ala Ser
            420

<210> SEQ ID NO 24
<211> LENGTH: 424
<212> TYPE: PRT
<213> ORGANISM: Artificial Sequence
<220> FEATURE:
<223> OTHER INFORMATION: Single target 10 #

<400> SEQUENCE: 24

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
            260                 265                 270

Glu Cys His Leu Glu Ile Arg Glu Asp Gly Thr Val Gly Cys Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
```

-continued

```
                    325                 330                 335
Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Val Phe Leu Pro Leu Pro Gly
    370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Gly Ser Gln
                405                 410                 415

Gly Leu Ser Pro Ser Tyr Ala Ser
                420

<210> SEQ ID NO 25
<211> LENGTH: 424
<212> TYPE: PRT
<213> ORGANISM: Artificial Sequence
<220> FEATURE:
<223> OTHER INFORMATION: Single target 11 #

<400> SEQUENCE: 25

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
```

-continued

```
                260              265               270

Glu Cys His Leu Glu Ile Arg Glu Asp Gly Thr Val Gly Cys Ala Ala
        275              280               285

Asp Gln Ser Pro Glu Ser Leu Leu Gln Leu Lys Ala Leu Lys Pro Gly
    290              295               300

Val Ile Gln Ile Leu Gly Val Lys Thr Ser Arg Phe Leu Cys Gln Arg
305              310               315               320

Pro Asp Gly Ala Leu Tyr Gly Ser Leu His Phe Asp Pro Glu Ala Cys
            325              330               335

Ser Phe Arg Glu Arg Leu Leu Glu Asp Gly Tyr Asn Val Tyr Gln Ser
        340              345               350

Glu Ala His Gly Leu Pro Leu His Leu Pro Gly Asn Lys Ser Pro His
        355              360               365

Arg Asp Pro Ala Pro Arg Gly Pro Ala Val Phe Leu Pro Leu Pro Gly
    370              375               380

Leu Pro Pro Ala Leu Pro Glu Pro Pro Gly Ile Leu Ala Pro Gln Pro
385              390               395               400

Pro Asp Val Gly Ser Ser Asp Pro Leu His Met Val Gly Ala Ser Gln
            405              410               415

Gly Leu Ser Pro Ser Tyr Ala Ser
            420

<210> SEQ ID NO 26
<211> LENGTH: 424
<212> TYPE: PRT
<213> ORGANISM: Artificial Sequence
<220> FEATURE:
<223> OTHER INFORMATION: Single target 12 #

<400> SEQUENCE: 26

Glu Ser Lys Tyr Gly Pro Pro Cys Pro Pro Cys Pro Ala Pro Glu Ala
1                5               10               15

Ala Gly Gly Pro Ser Val Phe Leu Phe Pro Pro Lys Pro Lys Asp Thr
            20              25               30

Leu Met Ile Ser Arg Thr Pro Glu Val Thr Cys Val Val Val Asp Val
        35              40               45

Ser Gln Glu Asp Pro Glu Val Gln Phe Asn Trp Tyr Val Asp Gly Val
    50              55               60

Glu Val His Asn Ala Lys Thr Lys Pro Arg Glu Glu Gln Phe Asn Ser
65              70               75               80

Thr Tyr Arg Val Val Ser Val Leu Thr Val Leu His Gln Asp Trp Leu
            85              90               95

Asn Gly Lys Glu Tyr Lys Cys Lys Val Ser Asn Lys Gly Leu Pro Ser
            100             105               110

Ser Ile Glu Lys Thr Ile Ser Lys Ala Lys Gly Gln Pro Arg Glu Pro
        115             120               125

Gln Val Tyr Thr Leu Pro Pro Ser Gln Glu Glu Met Thr Lys Asn Gln
    130             135               140

Val Ser Leu Thr Cys Leu Val Lys Gly Phe Tyr Pro Ser Asp Ile Ala
145             150               155               160

Val Glu Trp Glu Ser Asn Gly Gln Pro Glu Asn Asn Tyr Lys Thr Thr
            165             170               175

Pro Pro Val Leu Asp Ser Asp Gly Ser Phe Phe Leu Tyr Ser Lys Leu
            180             185               190

Thr Val Asp Lys Ser Arg Trp Gln Glu Gly Asn Val Phe Ser Cys Ser
```

-continued

```
              195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Val Tyr Leu Tyr Thr Asp Asp Ala Gln Gln Thr
            260                 265                 270

Glu Ala His Leu Glu Ile Arg Glu Asp Gly Thr Val Gly Gly Ala Ala
            275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
            355                 360                 365

Arg Asp Pro Ala Pro Arg Gly Pro Ala Arg Phe Leu Pro Leu Pro Gly
    370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly Leu Ser Pro Ser Tyr Glu Ser
                420

<210> SEQ ID NO 27
<211> LENGTH: 470
<212> TYPE: PRT
<213> ORGANISM: Artificial Sequence
<220> FEATURE:
<223> OTHER INFORMATION: Dual target 1 #

<400> SEQUENCE: 27

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Glu Ser
            35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
```

-continued

```
                130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
                195                 200                 205

Trp Glu Ser Asn Gly Gln Pro Glu Asn Asn Tyr Lys Thr Thr Pro Pro
                210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Gly Gly Gly Ser Gly Gly Gly Gly Ser Gly Gly Gly Gly
                275                 280                 285

Ser His Pro Ile Pro Asp Ser Ser Pro Leu Leu Gln Phe Gly Gly Gln
        290                 295                 300

Val Arg Gln Val Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
                340                 345                 350

Gln Ile Leu Gly Val Lys Thr Ser Arg Phe Leu Cys Gln Arg Pro Asp
                355                 360                 365

Gly Ala Leu Tyr Gly Ser Leu His Phe Asp Pro Glu Ala Cys Ser Phe
        370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
                420                 425                 430

Pro Ala Leu Pro Glu Pro Pro Gly Ile Leu Ala Pro Gln Pro Pro Asp
                435                 440                 445

Val Gly Ser Ser Asp Pro Leu His Met Val Gly Ala Ser Gln Gly Leu
        450                 455                 460

Ser Pro Ser Tyr Ala Ser
465                 470
```

<210> SEQ ID NO 28
<211> LENGTH: 470
<212> TYPE: PRT
<213> ORGANISM: Artificial Sequence
<220> FEATURE:
<223> OTHER INFORMATION: Dual target 2 #

<400> SEQUENCE: 28

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
```

-continued

```
              20                25                30
Gly Gly Gly Ser Gly Gly Gly Gly Ser Gly Gly Gly Gly Ser Glu Ser
          35                40                45
Lys Tyr Gly Pro Pro Cys Pro Pro Cys Pro Ala Pro Glu Ala Ala Gly
      50                55                60
Gly Pro Ser Val Phe Leu Phe Pro Pro Lys Pro Lys Asp Thr Leu Met
65                70                75                80
Ile Ser Arg Thr Pro Glu Val Thr Cys Val Val Val Asp Val Ser Gln
              85                90                95
Glu Asp Pro Glu Val Gln Phe Asn Trp Tyr Val Asp Gly Val Glu Val
          100               105               110
His Asn Ala Lys Thr Lys Pro Arg Glu Glu Gln Phe Asn Ser Thr Tyr
      115               120               125
Arg Val Val Ser Val Leu Thr Val Leu His Gln Asp Trp Leu Asn Gly
      130               135               140
Lys Glu Tyr Lys Cys Lys Val Ser Asn Lys Gly Leu Pro Ser Ser Ile
145               150               155               160
Glu Lys Thr Ile Ser Lys Ala Lys Gly Gln Pro Arg Glu Pro Gln Val
              165               170               175
Tyr Thr Leu Pro Pro Ser Gln Glu Glu Met Thr Lys Asn Gln Val Ser
          180               185               190
Leu Thr Cys Leu Val Lys Gly Phe Tyr Pro Ser Asp Ile Ala Val Glu
          195               200               205
Trp Glu Ser Asn Gly Gln Pro Glu Asn Asn Tyr Lys Thr Thr Pro Pro
      210               215               220
Val Leu Asp Ser Asp Gly Ser Phe Phe Leu Tyr Ser Lys Leu Thr Val
225               230               235               240
Asp Lys Ser Arg Trp Gln Glu Gly Asn Val Phe Ser Cys Ser Val Met
              245               250               255
His Glu Ala Leu His Asn His Tyr Thr Gln Lys Ser Leu Ser Leu Ser
          260               265               270
Leu Gly Gly Gly Gly Gly Ser Gly Gly Gly Gly Ser Gly Gly Gly Gly
          275               280               285
Ser His Pro Ile Pro Asp Ser Ser Pro Leu Leu Gln Phe Gly Gly Gln
      290               295               300
Val Arg Gln Val Tyr Leu Tyr Thr Asp Asp Ala Gln Gln Thr Glu Ala
305               310               315               320
His Leu Glu Ile Arg Glu Asp Gly Thr Val Gly Gly Ala Ala Asp Gln
              325               330               335
Ser Pro Glu Ser Leu Leu Gln Leu Lys Ala Leu Lys Pro Gly Val Ile
          340               345               350
Gln Ile Leu Gly Val Lys Thr Ser Arg Phe Leu Cys Gln Arg Pro Asp
          355               360               365
Gly Ala Leu Tyr Gly Ser Leu His Phe Asp Pro Glu Ala Cys Ser Phe
      370               375               380
Arg Glu Arg Leu Leu Glu Asp Gly Tyr Asn Val Tyr Gln Ser Glu Ala
385               390               395               400
His Gly Leu Pro Leu His Leu Pro Gly Asn Lys Ser Pro His Arg Asp
              405               410               415
Pro Ala Pro Arg Gly Pro Ala Arg Phe Leu Pro Leu Pro Gly Leu Pro
          420               425               430
Pro Ala Leu Pro Glu Pro Pro Gly Ile Leu Ala Pro Gln Pro Pro Asp
          435               440               445
```

```
Val Gly Ser Ser Asp Pro Leu His Met Val Gly Gly Ser Gln Gly Leu
    450                 455                 460

Ser Pro Ser Tyr Ala Ser
465                 470

<210> SEQ ID NO 29
<211> LENGTH: 470
<212> TYPE: PRT
<213> ORGANISM: Artificial Sequence
<220> FEATURE:
<223> OTHER INFORMATION: Dual target 3 #

<400> SEQUENCE: 29

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Ser Glu Ser
        35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Gly Ser Gly Gly Gly Gly Ser Gly Gly Gly Gly
        275                 280                 285

Ser His Pro Ile Pro Asp Ser Ser Pro Leu Leu Gln Phe Gly Gly Gln
        290                 295                 300

Val Arg Gln Val Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335
```

```
Ser Pro Glu Ser Leu Leu Gln Leu Lys Ala Leu Lys Pro Gly Val Ile
        340                 345                 350

Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
        370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Val Phe Leu Pro Leu Pro Gly Leu Pro
                420                 425                 430

Pro Ala Leu Pro Glu Pro Pro Gly Ile Leu Ala Pro Gln Pro Pro Asp
        435                 440                 445

Val Gly Ser Ser Asp Pro Leu His Met Val Gly Gly Ser Gln Gly Leu
    450                 455                 460

Ser Pro Ser Tyr Ala Ser
465                 470

<210> SEQ ID NO 30
<211> LENGTH: 470
<212> TYPE: PRT
<213> ORGANISM: Artificial Sequence
<220> FEATURE:
<223> OTHER INFORMATION: Dual target 4 #

<400> SEQUENCE: 30

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
        20                  25                  30

Gly Gly Gly Ser Gly Gly Gly Gly Ser Gly Gly Gly Gly Ser Glu Ser
        35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
        130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
        210                 215                 220
```

-continued

```
Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Gly Gly Gly Ser Gly Gly Gly Gly Ser Gly Gly Gly Gly
                275                 280                 285

Ser His Pro Ile Pro Asp Ser Ser Pro Leu Leu Gln Phe Gly Gly Gln
            290                 295                 300

Val Arg Gln Val Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
                340                 345                 350

Gln Ile Leu Gly Val Lys Thr Ser Arg Phe Leu Cys Gln Arg Pro Asp
            355                 360                 365

Gly Ala Leu Tyr Gly Ser Leu His Phe Asp Pro Glu Ala Cys Ser Phe
            370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
                420                 425                 430

Pro Ala Leu Pro Glu Pro Pro Gly Ile Leu Ala Pro Gln Pro Pro Asp
            435                 440                 445

Val Gly Ser Ser Asp Pro Leu His Met Val Gly Gly Ser Gln Gly Leu
    450                 455                 460

Ser Pro Ser Tyr Glu Ser
465                 470

<210> SEQ ID NO 31
<211> LENGTH: 470
<212> TYPE: PRT
<213> ORGANISM: Artificial Sequence
<220> FEATURE:
<223> OTHER INFORMATION: Dual target 6 #

<400> SEQUENCE: 31

His Gly Glu Gly Thr Phe Thr Ser Asp Val Ser Ser Tyr Leu Glu Glu
1                   5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Glu Ser
            35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110
```

```
His Asn Ala Lys Thr Lys Pro Arg Glu Glu Gln Phe Asn Ser Thr Tyr
        115             120             125

Arg Val Val Ser Val Leu Thr Val Leu His Gln Asp Trp Leu Asn Gly
        130             135             140

Lys Glu Tyr Lys Cys Lys Val Ser Asn Lys Gly Leu Pro Ser Ser Ile
145             150             155             160

Glu Lys Thr Ile Ser Lys Ala Lys Gly Gln Pro Arg Glu Pro Gln Val
                165             170             175

Tyr Thr Leu Pro Pro Ser Gln Glu Glu Met Thr Lys Asn Gln Val Ser
            180             185             190

Leu Thr Cys Leu Val Lys Gly Phe Tyr Pro Ser Asp Ile Ala Val Glu
            195             200             205

Trp Glu Ser Asn Gly Gln Pro Glu Asn Asn Tyr Lys Thr Thr Pro Pro
        210             215             220

Val Leu Asp Ser Asp Gly Ser Phe Phe Leu Tyr Ser Lys Leu Thr Val
225             230             235             240

Asp Lys Ser Arg Trp Gln Glu Gly Asn Val Phe Ser Cys Ser Val Met
            245             250             255

His Glu Ala Leu His Asn His Tyr Thr Gln Lys Ser Leu Ser Leu Ser
            260             265             270

Leu Gly Gly Gly Gly Ser Gly Gly Gly Gly Ser Gly Gly Gly Gly
        275             280             285

Ser His Pro Ile Pro Asp Ser Ser Pro Leu Leu Gln Phe Gly Gly Gln
        290             295             300

Val Arg Gln Val Tyr Leu Tyr Thr Asp Asp Ala Gln Gln Thr Glu Ala
305             310             315             320

His Leu Glu Ile Arg Glu Asp Gly Thr Val Gly Gly Ala Ala Asp Gln
                325             330             335

Ser Pro Glu Ser Leu Leu Gln Leu Lys Ala Leu Lys Pro Gly Val Ile
            340             345             350

Gln Ile Leu Gly Val Lys Thr Ser Arg Phe Leu Cys Gln Arg Pro Asp
            355             360             365

Gly Ala Leu Tyr Gly Ser Leu His Phe Asp Pro Glu Ala Cys Ser Phe
        370             375             380

Arg Glu Arg Leu Leu Glu Asp Gly Tyr Asn Val Tyr Gln Ser Glu Ala
385             390             395             400

His Gly Leu Pro Leu His Leu Pro Gly Asn Lys Ser Pro His Arg Asp
                405             410             415

Pro Ala Pro Arg Gly Pro Ala Val Phe Leu Pro Leu Pro Gly Leu Pro
            420             425             430

Pro Ala Leu Pro Glu Pro Pro Gly Ile Leu Ala Pro Gln Pro Pro Asp
            435             440             445

Val Gly Ser Ser Asp Pro Leu His Met Val Gly Ala Ser Gln Gly Leu
    450             455             460

Ser Pro Ser Tyr Ala Ser
465             470
```

```
<210> SEQ ID NO 32
<211> LENGTH: 470
<212> TYPE: PRT
<213> ORGANISM: Artificial Sequence
<220> FEATURE:
<223> OTHER INFORMATION: Dual target 7 #

<400> SEQUENCE: 32
```

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Glu Ser
            35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
                115                 120                 125

Arg Val Val Ser Val Leu Thr Val Leu His Gln Asp Trp Leu Asn Gly
                130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
                195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Gly Gly Gly Gly Ser Gly Gly Gly Gly Ser Gly Gly Gly Gly
                275                 280                 285

Ser His Pro Ile Pro Asp Ser Ser Pro Leu Leu Gln Phe Gly Gly Gln
                290                 295                 300

Val Arg Gln Val Tyr Leu Tyr Thr Asp Asp Ala Gln Gln Thr Glu Cys
305                 310                 315                 320

His Leu Glu Ile Arg Glu Asp Gly Thr Val Gly Cys Ala Ala Asp Gln
                325                 330                 335

Ser Pro Glu Ser Leu Leu Gln Leu Lys Ala Leu Lys Pro Gly Val Ile
                340                 345                 350

Gln Ile Leu Gly Val Lys Thr Ser Arg Phe Leu Cys Gln Arg Pro Asp
                355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415
```

-continued

```
Pro Ala Pro Arg Gly Pro Ala Arg Phe Leu Pro Leu Pro Gly Leu Pro
            420                 425                 430

Pro Ala Leu Pro Glu Pro Gly Ile Leu Ala Pro Gln Pro Pro Asp
            435                 440                 445

Val Gly Ser Ser Asp Pro Leu His Met Val Gly Ala Ser Gln Gly Leu
    450                 455                 460

Ser Pro Ser Tyr Ala Ser
465                 470

<210> SEQ ID NO 33
<211> LENGTH: 470
<212> TYPE: PRT
<213> ORGANISM: Artificial Sequence
<220> FEATURE:
<223> OTHER INFORMATION: Dual target 9 #

<400> SEQUENCE: 33

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Ser Glu Ser
        35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Ser Gly Gly Gly Gly Ser Gly Gly Gly Gly
        275                 280                 285

Ser His Pro Ile Pro Asp Ser Ser Pro Leu Leu Gln Phe Gly Gly Gln
    290                 295                 300
```

-continued

```
Val Arg Gln Val Tyr Leu Tyr Thr Asp Asp Ala Gln Gln Thr Glu Cys
305                 310                 315                 320

His Leu Glu Ile Arg Glu Asp Gly Thr Val Gly Cys Ala Ala Asp Gln
                325                 330                 335

Ser Pro Glu Ser Leu Leu Gln Leu Lys Ala Leu Lys Pro Gly Val Ile
                340                 345                 350

Gln Ile Leu Gly Val Lys Thr Ser Arg Phe Leu Cys Gln Arg Pro Asp
                355                 360                 365

Gly Ala Leu Tyr Gly Ser Leu His Phe Asp Pro Glu Ala Cys Ser Phe
                370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
                420                 425                 430

Pro Ala Leu Pro Glu Pro Pro Gly Ile Leu Ala Pro Gln Pro Pro Asp
                435                 440                 445

Val Gly Ser Ser Asp Pro Leu His Met Val Gly Gly Ser Gln Gly Leu
    450                 455                 460

Ser Pro Ser Tyr Ala Ser
465                 470

<210> SEQ ID NO 34
<211> LENGTH: 470
<212> TYPE: PRT
<213> ORGANISM: Artificial Sequence
<220> FEATURE:
<223> OTHER INFORMATION: Dual target 10 #

<400> SEQUENCE: 34

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Ser Glu Ser
            35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
                115                 120                 125

Arg Val Val Ser Val Leu Thr Val Leu His Gln Asp Trp Leu Asn Gly
                130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190
```

```
Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Gly Gly Gly Gly Ser Gly Gly Gly Gly Ser Gly Gly Gly Gly
        275                 280                 285

Ser His Pro Ile Pro Asp Ser Ser Pro Leu Leu Gln Phe Gly Gly Gln
    290                 295                 300

Val Arg Gln Val Tyr Leu Tyr Thr Asp Asp Ala Gln Gln Thr Glu Cys
305                 310                 315                 320

His Leu Glu Ile Arg Glu Asp Gly Thr Val Gly Cys Ala Ala Asp Gln
                325                 330                 335

Ser Pro Glu Ser Leu Leu Gln Leu Lys Ala Leu Lys Pro Gly Val Ile
            340                 345                 350

Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Val Phe Leu Pro Leu Pro Gly Leu Pro
                420                 425                 430

Pro Ala Leu Pro Glu Pro Pro Gly Ile Leu Ala Pro Gln Pro Pro Asp
            435                 440                 445

Val Gly Ser Ser Asp Pro Leu His Met Val Gly Gly Ser Gln Gly Leu
    450                 455                 460

Ser Pro Ser Tyr Ala Ser
465                 470

<210> SEQ ID NO 35
<211> LENGTH: 470
<212> TYPE: PRT
<213> ORGANISM: Artificial Sequence
<220> FEATURE:
<223> OTHER INFORMATION: Dual target 11 #

<400> SEQUENCE: 35

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Gly Ser Gly Gly Gly Gly Ser Glu Ser
        35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80
```

```
Ile Ser Arg Thr Pro Glu Val Thr Cys Val Val Asp Val Ser Gln
            85              90              95

Glu Asp Pro Glu Val Gln Phe Asn Trp Tyr Val Asp Gly Val Glu Val
            100             105             110

His Asn Ala Lys Thr Lys Pro Arg Glu Glu Gln Phe Asn Ser Thr Tyr
            115             120             125

Arg Val Val Ser Val Leu Thr Val Leu His Gln Asp Trp Leu Asn Gly
    130             135             140

Lys Glu Tyr Lys Cys Lys Val Ser Asn Lys Gly Leu Pro Ser Ser Ile
145             150             155             160

Glu Lys Thr Ile Ser Lys Ala Lys Gly Gln Pro Arg Glu Pro Gln Val
                165             170             175

Tyr Thr Leu Pro Pro Ser Gln Glu Glu Met Thr Lys Asn Gln Val Ser
            180             185             190

Leu Thr Cys Leu Val Lys Gly Phe Tyr Pro Ser Asp Ile Ala Val Glu
            195             200             205

Trp Glu Ser Asn Gly Gln Pro Glu Asn Asn Tyr Lys Thr Thr Pro Pro
    210             215             220

Val Leu Asp Ser Asp Gly Ser Phe Phe Leu Tyr Ser Lys Leu Thr Val
225             230             235             240

Asp Lys Ser Arg Trp Gln Glu Gly Asn Val Phe Ser Cys Ser Val Met
            245             250             255

His Glu Ala Leu His Asn His Tyr Thr Gln Lys Ser Leu Ser Leu Ser
            260             265             270

Leu Gly Gly Gly Gly Gly Ser Gly Gly Gly Gly Ser Gly Gly Gly Gly
            275             280             285

Ser His Pro Ile Pro Asp Ser Ser Pro Leu Leu Gln Phe Gly Gly Gln
    290             295             300

Val Arg Gln Val Tyr Leu Tyr Thr Asp Asp Ala Gln Gln Thr Glu Cys
305             310             315             320

His Leu Glu Ile Arg Glu Asp Gly Thr Val Gly Cys Ala Ala Asp Gln
            325             330             335

Ser Pro Glu Ser Leu Leu Gln Leu Lys Ala Leu Lys Pro Gly Val Ile
            340             345             350

Gln Ile Leu Gly Val Lys Thr Ser Arg Phe Leu Cys Gln Arg Pro Asp
    355             360             365

Gly Ala Leu Tyr Gly Ser Leu His Phe Asp Pro Glu Ala Cys Ser Phe
    370             375             380

Arg Glu Arg Leu Leu Glu Asp Gly Tyr Asn Val Tyr Gln Ser Glu Ala
385             390             395             400

His Gly Leu Pro Leu His Leu Pro Gly Asn Lys Ser Pro His Arg Asp
            405             410             415

Pro Ala Pro Arg Gly Pro Ala Val Phe Leu Pro Leu Pro Gly Leu Pro
            420             425             430

Pro Ala Leu Pro Glu Pro Pro Gly Ile Leu Ala Pro Gln Pro Pro Asp
            435             440             445

Val Gly Ser Ser Asp Pro Leu His Met Val Gly Ala Ser Gln Gly Leu
    450             455             460

Ser Pro Ser Tyr Ala Ser
465             470
```

<210> SEQ ID NO 36
<211> LENGTH: 470
<212> TYPE: PRT

<213> ORGANISM: Artificial Sequence
<220> FEATURE:
<223> OTHER INFORMATION: Dual target 12 #

<400> SEQUENCE: 36

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Glu Ser
            35                  40                  45

Lys Tyr Gly Pro Pro Cys Pro Pro Cys Pro Ala Pro Glu Ala Ala Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
            100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190

Leu Thr Cys Leu Val Lys Gly Phe Tyr Pro Ser Asp Ile Ala Val Glu
            195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
            245                 250                 255

His Glu Ala Leu His Asn His Tyr Thr Gln Lys Ser Leu Ser Leu Ser
            260                 265                 270

Leu Gly Gly Gly Gly Gly Ser Gly Gly Gly Gly Ser Gly Gly Gly Gly
            275                 280                 285

Ser His Pro Ile Pro Asp Ser Ser Pro Leu Leu Gln Phe Gly Gly Gln
    290                 295                 300

Val Arg Gln Val Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
            340                 345                 350

Gln Ile Leu Gly Val Lys Thr Ser Arg Phe Leu Cys Gln Arg Pro Asp
            355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
```

-continued

```
385                390                395                400
His Gly Leu Pro Leu His Leu Pro Gly Asn Lys Ser Pro His Arg Asp
                405                410                415

Pro Ala Pro Arg Gly Pro Ala Arg Phe Leu Pro Leu Pro Gly Leu Pro
            420                425                430

Pro Ala Leu Pro Glu Pro Pro Gly Ile Leu Ala Pro Gln Pro Pro Asp
            435                440                445

Val Gly Ser Ser Asp Pro Leu His Met Val Gly Ala Ser Gln Gly Leu
    450                455                460

Ser Pro Ser Tyr Glu Ser
465                470

<210> SEQ ID NO 37
<211> LENGTH: 37
<212> TYPE: DNA
<213> ORGANISM: Artificial Sequence
<220> FEATURE:
<223> OTHER INFORMATION: Primer AUZ-F

<400> SEQUENCE: 37
cccaagcttg ccgccaccat gaccagactg accgtgc                              37

<210> SEQ ID NO 38
<211> LENGTH: 35
<212> TYPE: DNA
<213> ORGANISM: Artificial Sequence
<220> FEATURE:
<223> OTHER INFORMATION: Primer lfc1-R

<400> SEQUENCE: 38
gccgtacttg ctctcagatc caccgcctcc gcttc                                35

<210> SEQ ID NO 39
<211> LENGTH: 34
<212> TYPE: DNA
<213> ORGANISM: Artificial Sequence
<220> FEATURE:
<223> OTHER INFORMATION: Primer lfc1-F

<400> SEQUENCE: 39
gcggaggcgg tggatctgag agcaagtacg gccc                                 34

<210> SEQ ID NO 40
<211> LENGTH: 33
<212> TYPE: DNA
<213> ORGANISM: Artificial Sequence
<220> FEATURE:
<223> OTHER INFORMATION: Primer fgf21-R

<400> SEQUENCE: 40
ccggaattct catcagctgg cgtagctagg gct                                  33

<210> SEQ ID NO 41
<211> LENGTH: 470
<212> TYPE: PRT
<213> ORGANISM: Artificial Sequence
<220> FEATURE:
<223> OTHER INFORMATION: Dual target RAHL

<400> SEQUENCE: 41

His Gly Glu Gly Thr Phe Thr Ser Asp Val Ser Ser Tyr Leu Glu Glu
1               5                  10                 15

Gln Ala Ala Lys Glu Phe Ile Ala Trp Leu Val Lys Gly Gly Gly Gly
```

-continued

```
              20                25                30
Gly Gly Gly Ser Gly Gly Gly Gly Ser Gly Gly Gly Gly Ser Glu Ser
              35                40                45
Lys Tyr Gly Pro Pro Cys Pro Pro Cys Pro Ala Pro Glu Ala Ala Gly
              50                55                60
Gly Pro Ser Val Phe Leu Phe Pro Pro Lys Pro Lys Asp Thr Leu Met
65                70                75                80
Ile Ser Arg Thr Pro Glu Val Thr Cys Val Val Val Asp Val Ser Gln
              85                90                95
Glu Asp Pro Glu Val Gln Phe Asn Trp Tyr Val Asp Gly Val Glu Val
              100               105               110
His Asn Ala Lys Thr Lys Pro Arg Glu Glu Gln Phe Asn Ser Thr Tyr
              115               120               125
Arg Val Val Ser Val Leu Thr Val Leu His Gln Asp Trp Leu Asn Gly
              130               135               140
Lys Glu Tyr Lys Cys Lys Val Ser Asn Lys Gly Leu Pro Ser Ser Ile
145               150               155               160
Glu Lys Thr Ile Ser Lys Ala Lys Gly Gln Pro Arg Glu Pro Gln Val
              165               170               175
Tyr Thr Leu Pro Pro Ser Gln Glu Glu Met Thr Lys Asn Gln Val Ser
              180               185               190
Leu Thr Cys Leu Val Lys Gly Phe Tyr Pro Ser Asp Ile Ala Val Glu
              195               200               205
Trp Glu Ser Asn Gly Gln Pro Glu Asn Asn Tyr Lys Thr Thr Pro Pro
              210               215               220
Val Leu Asp Ser Asp Gly Ser Phe Phe Leu Tyr Ser Lys Leu Thr Val
225               230               235               240
Asp Lys Ser Arg Trp Gln Glu Gly Asn Val Phe Ser Cys Ser Val Met
              245               250               255
His Glu Ala Leu His Asn His Tyr Thr Gln Lys Ser Leu Ser Leu Ser
              260               265               270
Leu Gly Gly Gly Gly Ser Gly Gly Gly Gly Ser Gly Gly Gly Gly
              275               280               285
Ser His Pro Ile Pro Asp Ser Ser Pro Leu Leu Gln Phe Gly Gly Gln
              290               295               300
Val Arg Gln Arg Tyr Leu Tyr Thr Asp Asp Ala Gln Gln Thr Glu Ala
305               310               315               320
His Leu Glu Ile Arg Glu Asp Gly Thr Val Gly Gly Ala Ala Asp Gln
              325               330               335
Ser Pro Glu Ser Leu Leu Gln Leu Lys Ala Leu Lys Pro Gly Val Ile
              340               345               350
Gln Ile Leu Gly Val Lys Thr Ser Arg Phe Leu Cys Gln Arg Pro Asp
              355               360               365
Gly Ala Leu Tyr Gly Ser Leu His Phe Asp Pro Glu Ala Cys Ser Phe
              370               375               380
Arg Glu Arg Leu Leu Glu Asp Gly Tyr Asn Val Tyr Gln Ser Glu Ala
385               390               395               400
His Gly Leu Pro Leu His Leu Pro Gly Asn Lys Ser Pro His Arg Asp
              405               410               415
Pro Ala Pro Arg Gly Pro Ala Arg Phe Leu Pro Leu Pro Gly Leu Pro
              420               425               430
Pro Ala Leu Pro Glu Pro Pro Gly Ile Leu Ala Pro Gln Pro Pro Asp
              435               440               445
```

-continued

```
Val Gly Ser Ser Asp Pro Leu His Met Val Gly Ala Ser Gln Gly Leu
    450             455             460

Ser Pro Ser Tyr Ala Ser
465             470

<210> SEQ ID NO 42
<211> LENGTH: 470
<212> TYPE: PRT
<213> ORGANISM: Artificial Sequence
<220> FEATURE:
<223> OTHER INFORMATION: Dual target RGHL

<400> SEQUENCE: 42

His Gly Glu Gly Thr Phe Thr Ser Asp Val Ser Ser Tyr Leu Glu Glu
1               5               10              15

Gln Ala Ala Lys Glu Phe Ile Ala Trp Leu Val Lys Gly Gly Gly Gly
            20              25              30

Gly Gly Gly Ser Gly Gly Gly Gly Ser Gly Gly Gly Gly Ser Glu Ser
        35              40              45

Lys Tyr Gly Pro Pro Cys Pro Pro Cys Pro Ala Pro Glu Ala Ala Gly
    50              55              60

Gly Pro Ser Val Phe Leu Phe Pro Pro Lys Pro Lys Asp Thr Leu Met
65              70              75              80

Ile Ser Arg Thr Pro Glu Val Thr Cys Val Val Val Asp Val Ser Gln
            85              90              95

Glu Asp Pro Glu Val Gln Phe Asn Trp Tyr Val Asp Gly Val Glu Val
            100             105             110

His Asn Ala Lys Thr Lys Pro Arg Glu Glu Gln Phe Asn Ser Thr Tyr
        115             120             125

Arg Val Val Ser Val Leu Thr Val Leu His Gln Asp Trp Leu Asn Gly
    130             135             140

Lys Glu Tyr Lys Cys Lys Val Ser Asn Lys Gly Leu Pro Ser Ser Ile
145             150             155             160

Glu Lys Thr Ile Ser Lys Ala Lys Gly Gln Pro Arg Glu Pro Gln Val
            165             170             175

Tyr Thr Leu Pro Pro Ser Gln Glu Glu Met Thr Lys Asn Gln Val Ser
            180             185             190

Leu Thr Cys Leu Val Lys Gly Phe Tyr Pro Ser Asp Ile Ala Val Glu
        195             200             205

Trp Glu Ser Asn Gly Gln Pro Glu Asn Asn Tyr Lys Thr Thr Pro Pro
    210             215             220

Val Leu Asp Ser Asp Gly Ser Phe Phe Leu Tyr Ser Lys Leu Thr Val
225             230             235             240

Asp Lys Ser Arg Trp Gln Glu Gly Asn Val Phe Ser Cys Ser Val Met
            245             250             255

His Glu Ala Leu His Asn His Tyr Thr Gln Lys Ser Leu Ser Leu Ser
        260             265             270

Leu Gly Gly Gly Gly Gly Ser Gly Gly Gly Gly Ser Gly Gly Gly Gly
        275             280             285

Ser His Pro Ile Pro Asp Ser Ser Pro Leu Leu Gln Phe Gly Gly Gln
        290             295             300

Val Arg Gln Arg Tyr Leu Tyr Thr Asp Asp Ala Gln Gln Thr Glu Ala
305             310             315             320

His Leu Glu Ile Arg Glu Asp Gly Thr Val Gly Gly Ala Ala Asp Gln
            325             330             335
```

-continued

```
Ser Pro Glu Ser Leu Leu Gln Leu Lys Ala Leu Lys Pro Gly Val Ile
        340                 345                 350

Gln Ile Leu Gly Val Lys Thr Ser Arg Phe Leu Cys Gln Arg Pro Asp
        355                 360                 365

Gly Ala Leu Tyr Gly Ser Leu His Phe Asp Pro Glu Ala Cys Ser Phe
        370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Arg Phe Leu Pro Leu Pro Gly Leu Pro
                420                 425                 430

Pro Ala Leu Pro Glu Pro Pro Gly Ile Leu Ala Pro Gln Pro Pro Asp
        435                 440                 445

Val Gly Ser Ser Asp Pro Leu His Met Val Gly Gly Ser Gln Gly Leu
        450                 455                 460

Ser Pro Ser Tyr Ala Ser
465                 470

<210> SEQ ID NO 43
<211> LENGTH: 470
<212> TYPE: PRT
<213> ORGANISM: Artificial Sequence
<220> FEATURE:
<223> OTHER INFORMATION: Dual target RGHLQQ

<400> SEQUENCE: 43

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
        20                  25                  30

Gly Gly Gly Ser Gly Gly Gly Gly Ser Gly Gly Gly Gly Ser Glu Ser
        35                  40                  45

Lys Tyr Gly Pro Pro Cys Pro Pro Cys Pro Ala Pro Glu Ala Ala Gly
        50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser Gln
                85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
        130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
        210                 215                 220
```

-continued

```
Val Leu Asp Ser Asp Gly Ser Phe Phe Leu Tyr Ser Lys Leu Thr Val
225             230             235             240

Asp Lys Ser Arg Trp Gln Glu Gly Asn Val Phe Ser Cys Ser Val Met
            245             250             255

His Glu Ala Leu His Asn His Tyr Thr Gln Lys Ser Leu Ser Leu Ser
            260             265             270

Leu Gly Gly Gly Gly Ser Gly Gly Gly Gly Ser Gly Gly Gly Gly
        275             280             285

Ser His Pro Ile Pro Asp Ser Ser Pro Leu Leu Gln Phe Gly Gly Gln
    290             295             300

Val Arg Gln Gln Tyr Leu Tyr Thr Asp Asp Ala Gln Gln Thr Glu Ala
305             310             315             320

His Leu Glu Ile Arg Glu Asp Gly Thr Val Gly Gly Ala Ala Asp Gln
            325             330             335

Ser Pro Glu Ser Leu Leu Gln Leu Lys Ala Leu Lys Pro Gly Val Ile
            340             345             350

Gln Ile Leu Gly Val Lys Thr Ser Arg Phe Leu Cys Gln Arg Pro Asp
        355             360             365

Gly Ala Leu Tyr Gly Ser Leu His Phe Asp Pro Glu Ala Cys Ser Phe
    370             375             380

Arg Glu Arg Leu Leu Glu Asp Gly Tyr Asn Val Tyr Gln Ser Glu Ala
385             390             395             400

His Gly Leu Pro Leu His Leu Pro Gly Asn Lys Ser Pro His Arg Asp
            405             410             415

Pro Ala Pro Arg Gly Pro Ala Gln Phe Leu Pro Leu Pro Gly Leu Pro
            420             425             430

Pro Ala Leu Pro Glu Pro Pro Gly Ile Leu Ala Pro Gln Pro Pro Asp
        435             440             445

Val Gly Ser Ser Asp Pro Leu His Met Val Gly Gly Ser Gln Gly Leu
    450             455             460

Ser Pro Ser Tyr Ala Ser
465             470
```

```
<210> SEQ ID NO 44
<211> LENGTH: 470
<212> TYPE: PRT
<213> ORGANISM: Artificial Sequence
<220> FEATURE:
<223> OTHER INFORMATION: Dual target RAHLQQ

<400> SEQUENCE: 44
```

```
His Gly Glu Gly Thr Phe Thr Ser Asp Val Ser Ser Tyr Leu Glu Glu
1               5               10              15

Gln Ala Ala Lys Glu Phe Ile Ala Trp Leu Val Lys Gly Gly Gly Gly
            20              25              30

Gly Gly Gly Ser Gly Gly Gly Gly Ser Gly Gly Gly Gly Ser Glu Ser
        35              40              45

Lys Tyr Gly Pro Pro Cys Pro Pro Cys Pro Ala Pro Glu Ala Ala Gly
    50              55              60

Gly Pro Ser Val Phe Leu Phe Pro Pro Lys Pro Lys Asp Thr Leu Met
65              70              75              80

Ile Ser Arg Thr Pro Glu Val Thr Cys Val Val Val Asp Val Ser Gln
            85              90              95

Glu Asp Pro Glu Val Gln Phe Asn Trp Tyr Val Asp Gly Val Glu Val
            100             105             110
```

```
His Asn Ala Lys Thr Lys Pro Arg Glu Glu Gln Phe Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
                180                 185                 190

Leu Thr Cys Leu Val Lys Gly Phe Tyr Pro Ser Asp Ile Ala Val Glu
                195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
                260                 265                 270

Leu Gly Gly Gly Gly Ser Gly Gly Gly Gly Ser Gly Gly Gly Gly
                275                 280                 285

Ser His Pro Ile Pro Asp Ser Ser Pro Leu Leu Gln Phe Gly Gly Gln
    290                 295                 300

Val Arg Gln Gln Tyr Leu Tyr Thr Asp Asp Ala Gln Gln Thr Glu Ala
305                 310                 315                 320

His Leu Glu Ile Arg Glu Asp Gly Thr Val Gly Gly Ala Ala Asp Gln
                325                 330                 335

Ser Pro Glu Ser Leu Leu Gln Leu Lys Ala Leu Lys Pro Gly Val Ile
                340                 345                 350

Gln Ile Leu Gly Val Lys Thr Ser Arg Phe Leu Cys Gln Arg Pro Asp
    355                 360                 365

Gly Ala Leu Tyr Gly Ser Leu His Phe Asp Pro Glu Ala Cys Ser Phe
    370                 375                 380

Arg Glu Arg Leu Leu Glu Asp Gly Tyr Asn Val Tyr Gln Ser Glu Ala
385                 390                 395                 400

His Gly Leu Pro Leu His Leu Pro Gly Asn Lys Ser Pro His Arg Asp
                405                 410                 415

Pro Ala Pro Arg Gly Pro Ala Gln Phe Leu Pro Leu Pro Gly Leu Pro
                420                 425                 430

Pro Ala Leu Pro Glu Pro Pro Gly Ile Leu Ala Pro Gln Pro Pro Asp
                435                 440                 445

Val Gly Ser Ser Asp Pro Leu His Met Val Gly Ala Ser Gln Gly Leu
    450                 455                 460

Ser Pro Ser Tyr Ala Ser
465                 470
```

```
<210> SEQ ID NO 45
<211> LENGTH: 424
<212> TYPE: PRT
<213> ORGANISM: Artificial Sequence
<220> FEATURE:
<223> OTHER INFORMATION: Single target RGHLQQ

<400> SEQUENCE: 45
```

-continued

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Gln Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
            325                 330                 335

Ser Phe Arg Glu Arg Leu Leu Glu Asp Gly Tyr Asn Val Tyr Gln Ser
            340                 345                 350

Glu Ala His Gly Leu Pro Leu His Leu Pro Gly Asn Lys Ser Pro His
        355                 360                 365

Arg Asp Pro Ala Pro Arg Gly Pro Ala Gln Phe Leu Pro Leu Pro Gly
    370                 375                 380

Leu Pro Pro Ala Leu Pro Glu Pro Gly Ile Leu Ala Pro Gln Pro
385                 390                 395                 400

Pro Asp Val Gly Ser Ser Asp Pro Leu His Met Val Gly Gly Ser Gln
            405                 410                 415
```

```
Gly Leu Ser Pro Ser Tyr Ala Ser
            420

<210> SEQ ID NO 46
<211> LENGTH: 424
<212> TYPE: PRT
<213> ORGANISM: Artificial Sequence
<220> FEATURE:
<223> OTHER INFORMATION: Single target RAHL

<400> SEQUENCE: 46

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Gly Gly Gly Ser Gly Gly Gly Ser Gly Gly
225                 230                 235                 240

Gly Gly Ser His Pro Ile Pro Asp Ser Ser Pro Leu Leu Gln Phe Gly
            245                 250                 255

Gly Gln Val Arg Gln Arg Tyr Leu Tyr Thr Asp Asp Ala Gln Gln Thr
            260                 265                 270

Glu Ala His Leu Glu Ile Arg Glu Asp Gly Thr Val Gly Gly Ala Ala
        275                 280                 285

Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
            325                 330                 335

Ser Phe Arg Glu Arg Leu Leu Glu Asp Gly Tyr Asn Val Tyr Gln Ser
            340                 345                 350
```

-continued

```
Glu Ala His Gly Leu Pro Leu His Leu Pro Gly Asn Lys Ser Pro His
        355                 360                 365

Arg Asp Pro Ala Pro Arg Gly Pro Ala Arg Phe Leu Pro Leu Pro Gly
        370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Ala Ser Gln
                405                 410                 415

Gly Leu Ser Pro Ser Tyr Ala Ser
                420

<210> SEQ ID NO 47
<211> LENGTH: 424
<212> TYPE: PRT
<213> ORGANISM: Artificial Sequence
<220> FEATURE:
<223> OTHER INFORMATION: Single target RGHL

<400> SEQUENCE: 47

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
                180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
        210                 215                 220

Leu Ser Leu Gly Gly Gly Gly Ser Gly Gly Gly Gly Ser Gly Gly
225                 230                 235                 240

Gly Gly Ser His Pro Ile Pro Asp Ser Ser Pro Leu Leu Gln Phe Gly
                245                 250                 255

Gly Gln Val Arg Gln Arg Tyr Leu Tyr Thr Asp Asp Ala Gln Gln Thr
                260                 265                 270

Glu Ala His Leu Glu Ile Arg Glu Asp Gly Thr Val Gly Gly Ala Ala
        275                 280                 285
```

```
Asp Gln Ser Pro Glu Ser Leu Leu Gln Leu Lys Ala Leu Lys Pro Gly
    290                 295                 300

Val Ile Gln Ile Leu Gly Val Lys Thr Ser Arg Phe Leu Cys Gln Arg
305                 310                 315                 320

Pro Asp Gly Ala Leu Tyr Gly Ser Leu His Phe Asp Pro Glu Ala Cys
                325                 330                 335

Ser Phe Arg Glu Arg Leu Leu Glu Asp Gly Tyr Asn Val Tyr Gln Ser
                340                 345                 350

Glu Ala His Gly Leu Pro Leu His Leu Pro Gly Asn Lys Ser Pro His
                355                 360                 365

Arg Asp Pro Ala Pro Arg Gly Pro Ala Arg Phe Leu Pro Leu Pro Gly
    370                 375                 380

Leu Pro Pro Ala Leu Pro Glu Pro Pro Gly Ile Leu Ala Pro Gln Pro
385                 390                 395                 400

Pro Asp Val Gly Ser Ser Asp Pro Leu His Met Val Gly Gly Ser Gln
                405                 410                 415

Gly Leu Ser Pro Ser Tyr Ala Ser
                420

<210> SEQ ID NO 48
<211> LENGTH: 424
<212> TYPE: PRT
<213> ORGANISM: Artificial Sequence
<220> FEATURE:
<223> OTHER INFORMATION: Single target RGE

<400> SEQUENCE: 48

Glu Ser Lys Tyr Gly Pro Pro Cys Pro Pro Cys Pro Ala Pro Glu Ala
1                   5                   10                  15

Ala Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
                115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
                180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
    210                 215                 220
```

-continued

```
Leu Ser Leu Gly Gly Gly Gly Gly Ser Gly Gly Gly Gly Ser Gly Gly
225             230             235             240

Gly Gly Ser His Pro Ile Pro Asp Ser Ser Pro Leu Leu Gln Phe Gly
            245             250             255

Gly Gln Val Arg Gln Arg Tyr Leu Tyr Thr Asp Asp Ala Gln Gln Thr
            260             265             270

Glu Ala His Leu Glu Ile Arg Glu Asp Gly Thr Val Gly Gly Ala Ala
            275             280             285

Asp Gln Ser Pro Glu Ser Leu Leu Gln Leu Lys Ala Leu Lys Pro Gly
            290             295             300

Val Ile Gln Ile Leu Gly Val Lys Thr Ser Arg Phe Leu Cys Gln Arg
305             310             315             320

Pro Asp Gly Ala Leu Tyr Gly Ser Leu His Phe Asp Pro Glu Ala Cys
            325             330             335

Ser Phe Arg Glu Arg Leu Leu Glu Asp Gly Tyr Asn Val Tyr Gln Ser
            340             345             350

Glu Ala His Gly Leu Pro Leu His Leu Pro Gly Asn Lys Ser Pro His
            355             360             365

Arg Asp Pro Ala Pro Arg Gly Pro Ala Arg Phe Leu Pro Leu Pro Gly
            370             375             380

Leu Pro Pro Ala Leu Pro Glu Pro Pro Gly Ile Leu Ala Pro Gln Pro
385             390             395             400

Pro Asp Val Gly Ser Ser Asp Pro Leu Ser Met Val Gly Gly Ser Gln
            405             410             415

Gly Arg Ser Pro Ser Tyr Glu Ser
            420
```